US007985564B2

(12) United States Patent
Retallack et al.

(10) Patent No.: US 7,985,564 B2
(45) Date of Patent: Jul. 26, 2011

(54) EXPRESSION SYSTEMS WITH SEC-SYSTEM SECRETION

(75) Inventors: Diane M. Retallack, Poway, CA (US); Jane C. Schneider, San Diego, CA (US); Thomas Martin Ramseier, Poway, CA (US)

(73) Assignee: Pfenex, Inc., San Diego, CA (US)

( * ) Notice: Subject to any disclaimer, the term of this patent is extended or adjusted under 35 U.S.C. 154(b) by 1372 days.

(21) Appl. No.: 10/996,007

(22) Filed: Nov. 22, 2004

(65) Prior Publication Data

US 2006/0008877 A1     Jan. 12, 2006

Related U.S. Application Data

(60) Provisional application No. 60/524,124, filed on Nov. 21, 2003.

(51) Int. Cl.
*C12P 21/02* (2006.01)

(52) U.S. Cl. ............... 435/69.1; 435/320.1; 435/252.33; 435/252.34; 536/23.4

(58) Field of Classification Search .................. None
See application file for complete search history.

(56) References Cited

U.S. PATENT DOCUMENTS

| | | | |
|---|---|---|---|
| 4,963,495 A | 10/1990 | Chang et al. | |
| 5,082,783 A | 1/1992 | Ernst et al. | |
| 5,232,840 A | 8/1993 | Olins | |
| 5,288,852 A | 2/1994 | Yamada et al. | |
| 5,348,867 A | 9/1994 | Georgiou | |
| 5,378,806 A | 1/1995 | Willis | |
| 5,595,898 A | 1/1997 | Robinson et al. | |
| 5,629,172 A | 5/1997 | Mascarenhas et al. | |
| 5,641,671 A | 6/1997 | Bos et al. | |
| 5,698,435 A | 12/1997 | Robinson et al. | |
| 5,801,018 A | 9/1998 | Potter | |
| 5,914,254 A | 6/1999 | Mascarenhas et al. | |
| 5,958,754 A * | 9/1999 | Wong et al. | 435/252.8 |
| 6,156,552 A | 12/2000 | Okkels et al. | |
| 6,204,023 B1 | 3/2001 | Robinson et al. | |
| 6,225,106 B1 | 5/2001 | Gerritse et al. | |
| 6,258,560 B1 | 7/2001 | Leung et al. | |
| 6,329,172 B1 | 12/2001 | Rhee et al. | |
| 6,495,357 B1 | 12/2002 | Fuglsang et al. | |
| 6,509,181 B1 | 1/2003 | Danielsen et al. | |
| 6,524,827 B2 | 2/2003 | Moller et al. | |
| 6,528,298 B1 | 3/2003 | Svendsen et al. | |
| 6,558,939 B1 | 5/2003 | Nørregaard-Madsen et al. | |
| 6,608,018 B1 | 8/2003 | Shinohara | |
| 6,617,143 B1 | 9/2003 | Fukuyama | |
| 7,618,799 B2 | 11/2009 | Coleman | |
| 2003/0013150 A1 | 1/2003 | Manosroi et al. | |
| 2003/0044906 A1 | 3/2003 | Habermann et al. | |
| 2003/0064435 A1 | 4/2003 | Weiner et al. | |
| 2003/0180937 A1 | 9/2003 | Georgiou | |

FOREIGN PATENT DOCUMENTS

| | | |
|---|---|---|
| EP | 0117343 | 3/1987 |
| EP | 0121352 | 7/1988 |
| SG | 200603356-7 | 5/2008 |
| WO | WO 89/10971 | 11/1989 |
| WO | WO 93/02198 | 2/1993 |
| WO | WO 96/17943 | 6/1996 |
| WO | WO 00/59537 | 10/2000 |
| WO | WO 01/21662 | 3/2001 |
| WO | WO 02/40696 | 5/2002 |
| WO | WO 02/68660 | 6/2002 |
| WO | WO 03/068926 | 8/2003 |
| WO | WO 03/079007 | 9/2003 |
| WO | WO 03/089455 | 10/2003 |
| WO | WO 2005/069913 A2 | 8/2005 |
| WO | WO 2005/069913 A3 | 8/2005 |
| WO | WO-2005-89093 A2 | 9/2005 |

OTHER PUBLICATIONS

Arvidsson et al., Eur. J. Biochem., 1989, vol. 170, pp. 195-200.*
Bode et al., EST Database Accession No. CO372298/c, available Jun. 29, 2004.*
Wu et al., Journal of Bioscience and Bioengineering, 1999, vol. 87, No. 3, pp. 273-279.*
Whitelaw et al., EST Database Accession No. BX685867/c, available Feb. 5, 2003.*
Cross et al., Mammalian Genome, 2000, vol. 11, pp. 373-383.*
AJ236686/c, EMBL Accession Number, available May 2, 2000.*
Bardwell et al., "Pathways of Disulfide Bond Formation in Protiens in Vivo," 1994, Phosphate Microorg. 270-275.
De, 1995, FEMS Micr. Let. 127:263-272.
Derman et al., "Mutations that Allow Disulfide Bond Formation in the Cytoplasm of *Escherichia coli*," 1993, Science 262:1744-7.
Hockney, "Recent Developments in Heterologous Protein Production in *Escherichia coli*," 1994, Trends Biotechnol. 12:456-463.
International Search Report, Application No. PCT/US04/39316, Aug. 7, 2005, pp. 1-5.
Manoil, "Tagging Exported Proteins Using *Escherichia coli* Alkaline Phosphatase Gene Fusions," 2000, Methods in Enz. 326:35-47.
Muller et al., "Protein Traffic in Bacteria: Multiple Routes From the Ribosome to and Across the Membrane," 2001, Prog Nucleic Acid Res Mol Biol. 66:107-157.
Schein, "Production of Soluble Recombinant Proteins in Bacteria," 1989, Bio/Technology 7:1141-1149.
Yamano et al., "Cloning and nucleotide sequence of anaerobically induced porin protein E1 (OprE) of *Pseudomanas aeruginosa* PAO1," 1993, Molecular Microbiology vol. 8 No. 5: 993-1004.
Cross, S.H., et al., "CpG Island Libraries from Human Chromosomes 18 and 22: Landmarks for Novel Genes,"*Mammalian Genome*, 2000, pp. 373-383, vol. 11 (XP002381699).
Toyama, H., et al., Azurin Involved in Alcohol Oxidation System in *Pseudomonas putida* HK5: Expression Analysis and Gene Cloning, *Biosci. Biotechnol. Biochem.*, 2001, pp. 1617-1626, vol. 65, No. 7 (XP-002441554).

(Continued)

*Primary Examiner* — James S Ketter

(74) *Attorney, Agent, or Firm* — Wilson Sonsini Goodrich & Rosati

(57) ABSTRACT

Improved methods and prokaryotic expression systems for producing recombinant proteins using Sec-system secretion signal peptides are described using *Pseudomonas fluorescens* Sec secretion systems. Specific novel Sec-system secretion signal peptides are described, as are fusion proteins and coding sequences for improved secretion of recombinant proteins and peptides.

93 Claims, 16 Drawing Sheets

OTHER PUBLICATIONS

EBI Accession No.Q88C54, published Jun. 1, 2003.
EMBL Database Accession No. AF057031 submitted Apr. 2, 1998 (XP-002483318).
Huber, D., "Use of Thioredoxin as a Reporter to Identify a Subset of *Escherichia coli* Signal Sequences That Promote Signal Recognition Particle-Dependent Translocation," J. Bacteriology 187(9):2983-2991 (2005).
Ma, Q. et al., "Protein Secretion Systems of *Pseudomonas aeruginosa* and *P. fluorescens*," Biochim. Biophys. Acta 1611(No. 1-2):223-233 (2003).
Miot, M. and Betton, J., "Protein Quality Control in the Bacterial Periplasm," Microbial Cell Factories, 2004, pp. 1-13.
NCBI Database Accession No. Q3KH17, Direct Submission Aug. 2005 (SP-002483317).
NCBI Report for Accession No. YP_346180, Direct Submission on Aug. 8, 2005.
Paulson et al., "Complete genome sequence of the plant commensal *Pseudomonas fluorescens* Pf-5," Nature Biotech. 23:873-878 (2005).
Retallack, D.M. et al., "Transport of Heterologous Proteins to the Periplasmic Space of *Pseudomonas fluorescens* Using a Variety of Native Signal Sequences," Biotechnol. Lett. 29(10):1483-1491 (2007).
Urban, A. et al., "DsbA and DsbC Affect Extracellular Enzyme Formation in *Pseudomonas aeruginosa*," J. Bacteriol. 183(2):587-596 (2001).
Wang, H. et al., "High-level Expression of Human TFF3 in *Escherichia coli*," Peptides 26(7):1213-1218 (2005).
PCT/US08/52434 Search Report dated Sep. 25, 2008.

* cited by examiner

Figure 2

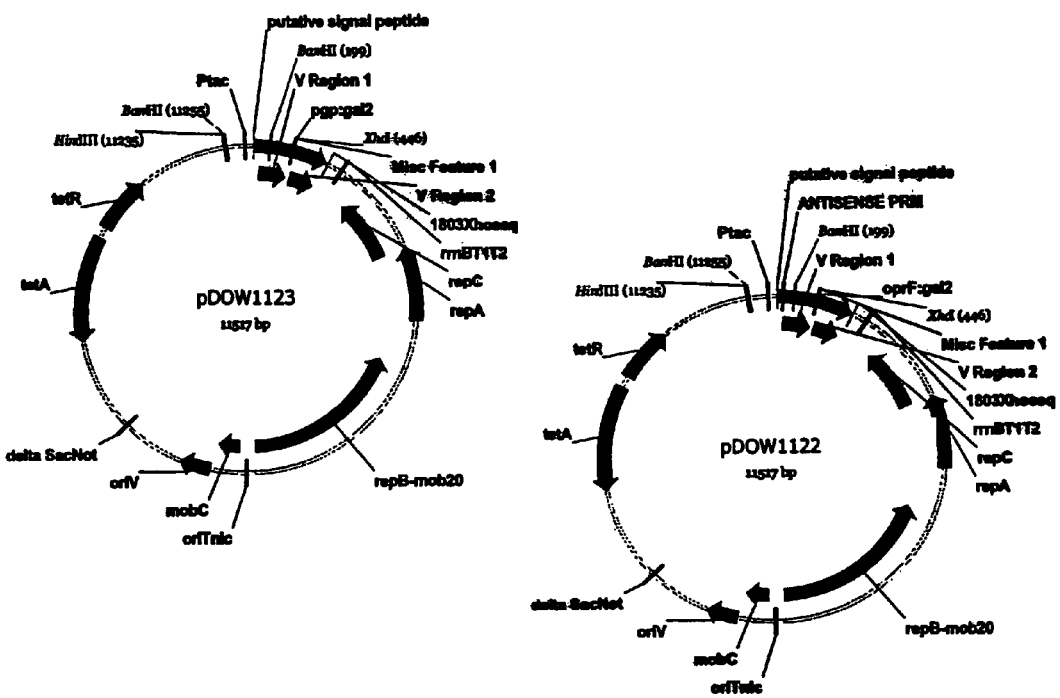

B.
MKLKNTLGLAIGSLIAATSFGVLA*AQVQLQESGPGLVKPSETLSLTCTVSGGSISSYHWSWI
RQPPGKGLEWIGYIYYSGSTNYNPSLKNRVTISVDTSKNQFSLNLRSVTAADTAVYYCARG
TYGPAGDAFDIWGQGTTVTVSSGGGGSGGGGSGGGGSDIQMTQSPSTLSASIGDRVTITC
RASEGIYHWLAWYQQKPGKAPKLLIYKASSLASGAPSRFSGSGSGTDFTLTISSLQPDDFAT
YYCQQYSNYPLTFGGGTKLEIKRAAAHHHHHH (SEQ ID NO: 13)

C.
MKLKRLMAAMTFVAAGVATANAVA*AQVQLQESGPGLVKPSETLSLTCTVSGGSISSYHWS
WI
RQPPGKGLEWIGYIYYSGSTNYNPSLKNRVTISVDTSKNQFSLNLRSVTAADTAVYYCARG
TYGPAGDAFDIWGQGTTVTVSSGGGGSGGGGSGGGGSDIQMTQSPSTLSASIGDRVTITC
RASEGIYHWLAWYQQKPGKAPKLLIYKASSLASGAPSRFSGSGSGTDFTLTISSLQPDDFAT
YYCQQYSNYPLTFGGGTKLEIKRAAAHHHHHH
(SEQ ID NO 14)

Figure 3
A.
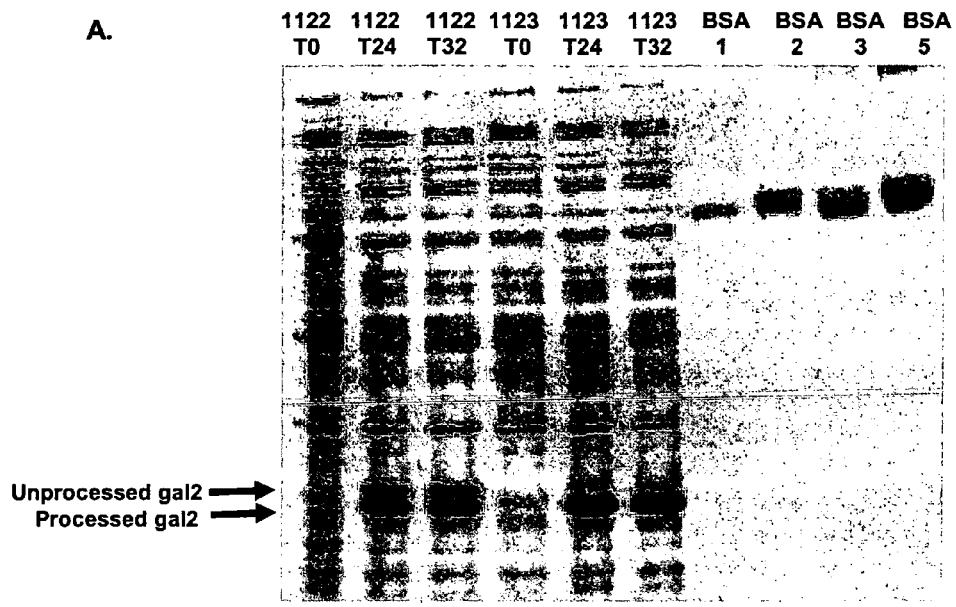
B.
Western Analysis of pbp:gal2 (pDOW1123) and oprF:gal2 (pDOW1122)
Expression at the 20L Scale (32 hour induction)
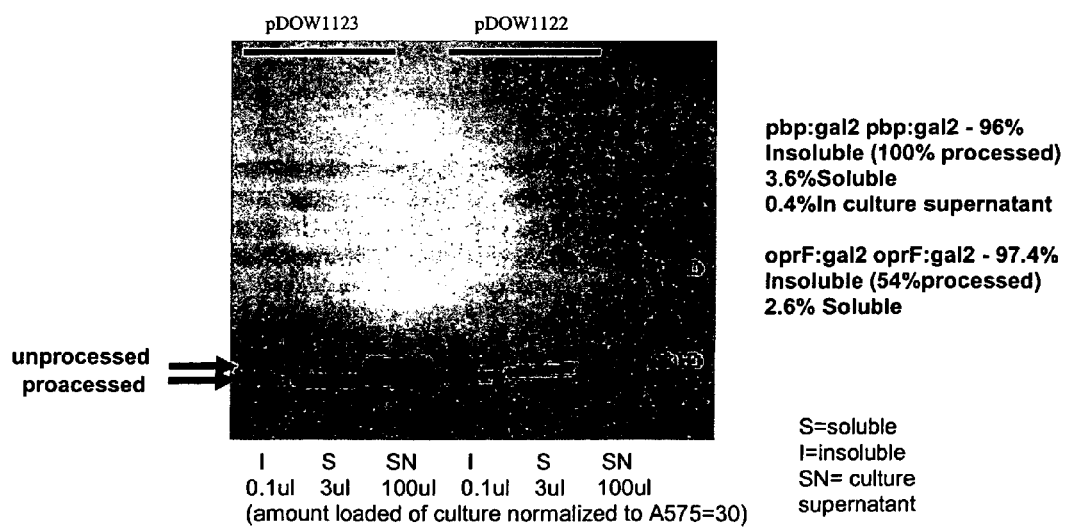
pbp:gal2 pbp:gal2 - 96%
Insoluble (100% processed)
3.6%Soluble
0.4%In culture supernatant
oprF:gal2 oprF:gal2 - 97.4%
Insoluble (54%processed)
2.6% Soluble
S=soluble
I=insoluble
SN= culture supernatant Figure 5
A
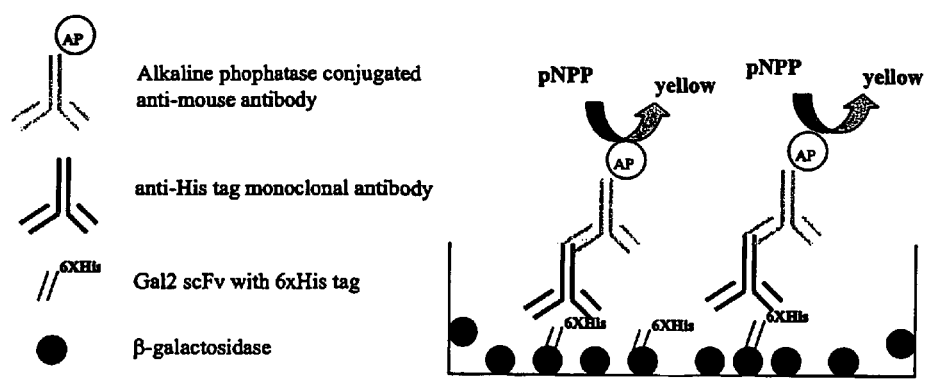
B
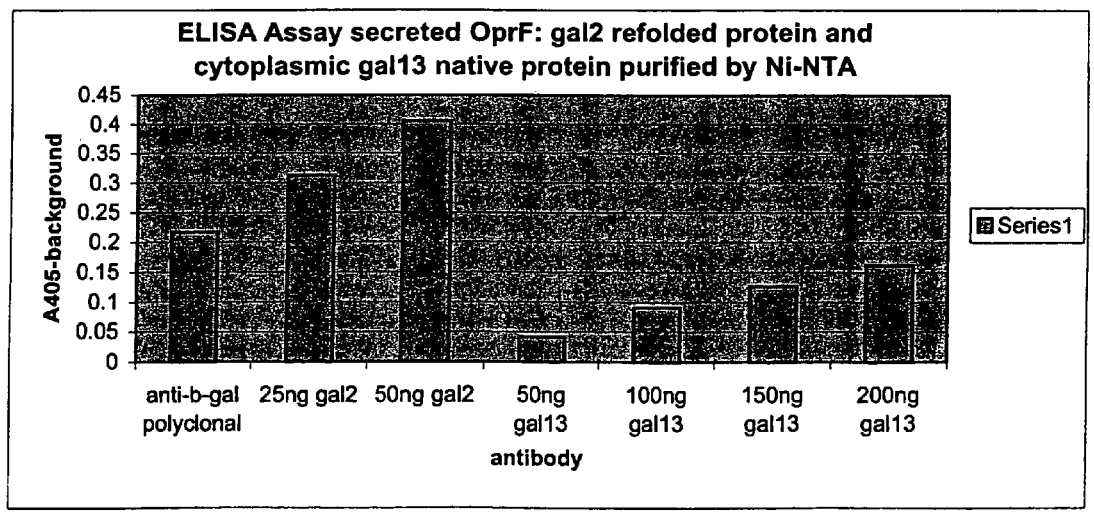

Figure 6
A.
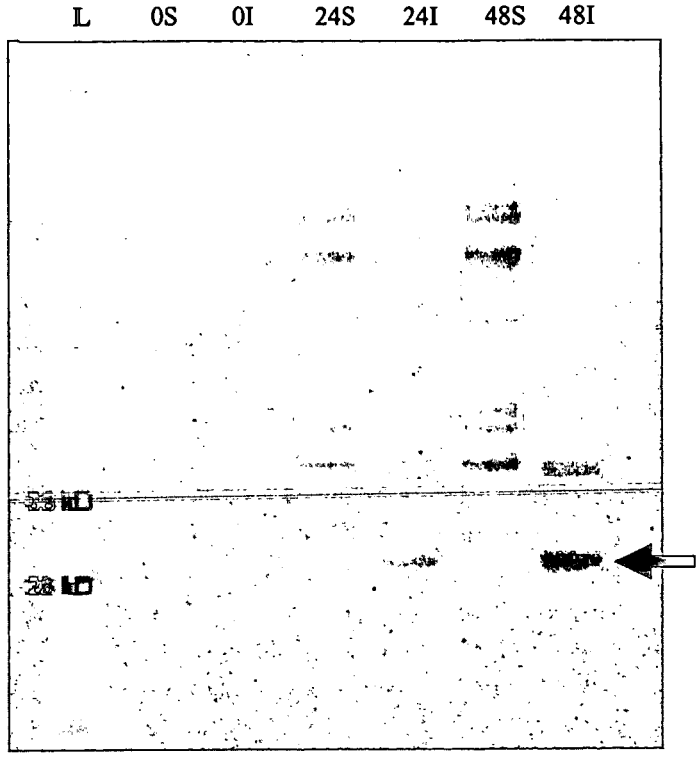
B.
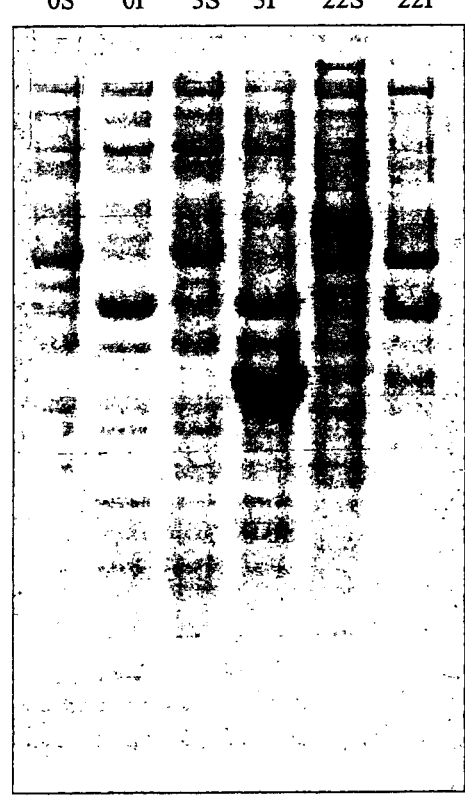

Figure 7
A.
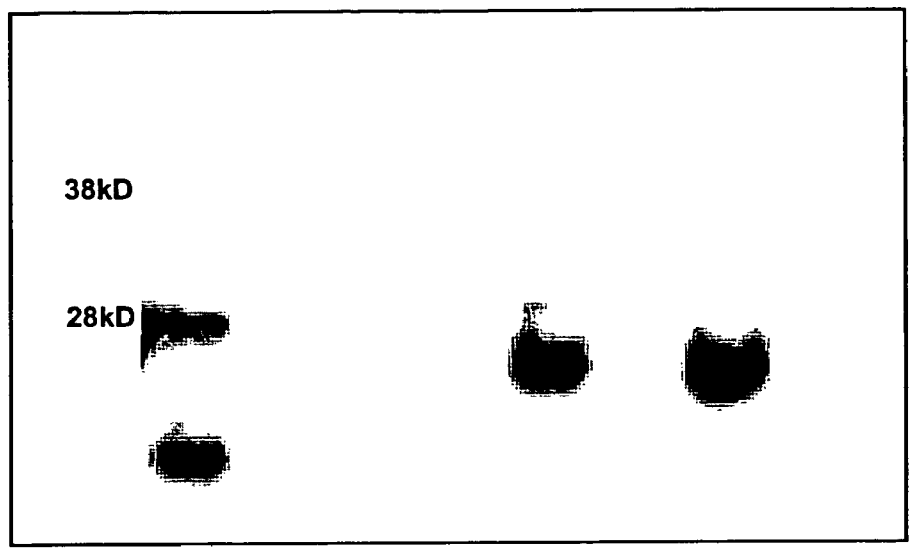
B.
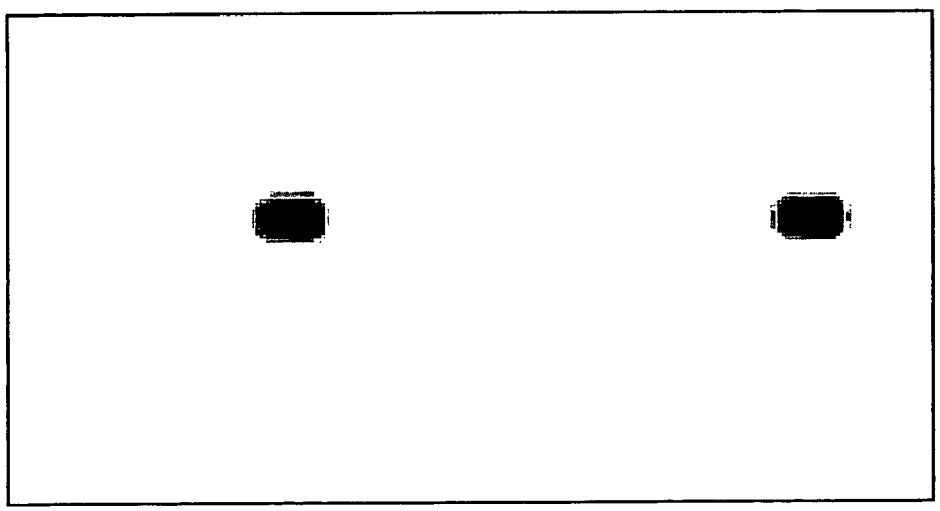

Figure 11

Amino acid sequence of the unprocessed Skp protein. The underlined sequence corresponds to the signal sequence.

<u>MKKWLLAAGLGLALATSAQA</u>ADKIAIVNMGSLFQQVAQKTGVSNTLENEFKGRAS
ELQRMETDLQAKMKKLQSMKAGSDRTKLEKDVMAQRQTFAQKAQAFEQDRARRS
NEERGKLVTRIQTAVKSVANSQDIDLVVDANAVAYNSSDVKDITADVLKQVK <u>(SEQ
ID NO: 30)</u>

Amino acid sequence of the processed Skp protein. The underlined sequence corresponds to the sequence that was identified by MALDI-PSD.

<u>ADKIAIVNMGSLFQQVAQKTGVSNTLENEFKGRASELQRMETDLQAKMKKLQSMK
AGSDRTKLEKDVMAQRQTFAQKAQAFEQDRARRSNEERGKLVTRIQTAVKSVANS
QDIDLVVDANAVAYNSSDVKDITADVLKQV</u> (SEQ ID NO: 31)

EXPRESSION SYSTEMS WITH SEC-SYSTEM SECRETION

CROSS REFERENCE TO RELATED APPLICATIONS

This application claims priority to U.S. Provisional Application No. 60/524,124, filed Nov. 21, 2003, entitled "Improved Expression Systems With Sec-System Secretion."

FIELD OF THE INVENTION

This invention is in the field of protein production and is an improved method to produce properly processed heterologous proteins by utilizing Sec targeting peptides and the *Pseudomonas fluorescens* Sec secretion system.

BACKGROUND

More than 150 recombinantly produced proteins and peptides have been approved by the U.S. Food and Drug Administration (FDA) for use as biotechnology drugs and vaccines, with another 370 in clinical trials. Unlike small molecule therapeutics that are produced through chemical synthesis, proteins and peptides are most efficiently produced in living cells. However, current methods of production of recombinant proteins in bacteria often produce improperly folded, aggregated or inactive proteins, and many types of proteins require secondary modifications that are inefficiently achieved using known methods.

One primary problem with known methods lies in the formation of inclusion bodies made of aggregated proteins in the cytoplasm, which occur when an excess amount of protein accumulates in the cell. Another problem in recombinant protein production is establishing the proper secondary and tertiary conformation for the expressed proteins. One barrier is that bacterial cytoplasm actively resists disulfide bonds formation, which often underlies proper protein folding (Derman et al. (1993) *Science* 262:1744-7). As a result, many recombinant proteins, particularly those of eukaryotic origin, are improperly folded and inactive when produced in bacteria.

Numerous attempts have been developed to increase production of properly folded proteins in recombinant systems. For example, investigators have changed fermentation conditions (Schein (1989) *Bio/Technology*, 7:1141-1149), varied promoter strength, or used overexpressed chaperone proteins (Hockney (1994) *Trends Biotechnol.* 12:456-463), which can help prevent the formation of inclusion bodies.

Secretion

An alternative approach to increase the harvest of properly folded proteins is to secrete the protein from the intracellular environment. In Gram-negative bacteria, a protein secreted from the cytoplasm can end up in the periplasmic space, attached to the outer membrane, or in the extracellular broth. Inclusion bodies, made of aggregated proteins are usually not formed if proteins are secreted out of the cytoplasm of the cell. Secretion into the periplasmic space also has the well known effect of facilitating proper disulfide bond formation (Bardwell et al. (1994) *Phosphate Microorg.* 270-5; Manoil (2000) *Methods in Enz.* 326: 35-47). Secretion of recombinant protein is appealing because it can result in more efficient isolation of the protein; can promote proper folding and disulfide bond formation of the transgenic protein, leading to an increase in the percentage of the protein in active form; can result in reduced formation of inclusion bodies and reduced toxicity to the host cell; and can provide an increased percentage of the recombinant protein in soluble form. The potential for excretion of the protein of interest into the culture medium can also potentially promote continuous, rather than batch culture for protein production.

Gram-negative bacteria have evolved numerous systems for the active export of proteins across their dual membranes (see FIG. 1). These routes of secretion include, e.g.: the ABC (Type I) pathway, the Path/Fla (Type III) pathway, and the Path/Vir (Type IV) pathway for one-step translocation across both the plasma and outer membrane; the Sec (Type II), Tat, MscL, and Holins pathways for translocation across the plasma membrane; and the Sec-plus-fimbrial usher porin (FUP), Sec-plus-autotransporter (AT), Sec-plus-two partner secretion (TPS), Sec-plus-main terminal branch (MTB), and Tat-plus-MTB pathways for two-step translocation across the plasma and outer membranes. Not all bacteria have all of these secretion pathways.

Three protein systems (types I, III and IV) secrete proteins across both membranes in a single energy-coupled step. Four systems (Sec, Tat, MscL and Holins) secrete only across the inner membrane, and four other systems (MTB, FUP, AT and TPS) secrete only across the outer membrane.

The most common form of secretion of peptides with a signal sequence involves the Sec system. The Sec system is responsible for export of proteins with the N-terminal signal peptides across the cytoplasmic membranes (see Agarraberes and Dice (2001) *Biochim Biophys Acta*. 1513:1-24; Müller et al. (2001) *Prog Nucleic Acid Res Mol Biol.* 66:107-157). Protein complexes of the Sec family are found universally in prokaryotes and eukaryotes. The bacterial Sec system consists of transport proteins, a chaperone protein (SecB) or signal recognition particle (SRP) and signal peptidases (SPase I and SPase II). The Sec transport complex in *E. coli* consists of three integral inner membrane proteins, SecY, SecE and SecG, and the cytoplasmic ATPase, SecA. SecA recruits SecY/E/G complexes to form the active translocation channel. The chaperone protein SecB binds to the nascent polypeptide chain to prevent it from folding and targets it to SecA. The linear polypeptide chain is subsequently transported through the SecYEG channel and, following cleavage of the signal peptide, the protein is folded in the periplasm. Three auxiliary proteins (SecD, SecF and YajC) form a complex that is not essential for secretion but stimulates secretion up to ten-fold under many conditions, particularly at low temperatures.

Proteins that are transported into the periplasm, i.e. through a type II secretion system, can also be exported into the extracellular media in a further step. The mechanisms are generally through an autotransporter, a two partner secretion system, a main terminal branch system or a fimbrial usher porin.

Of the twelve known secretion systems in Gram-negative bacteria, eight are known to utilize targeting signal peptides found as part of the expressed protein. These signal peptides interact with the proteins of the secretion systems so that the cell properly directs the protein to its appropriate destination. Five of these eight signal-peptide-based secretion systems are those that involve the Sec-system. These five are referred to as involved in Sec-dependent cytoplasmic membrane translocation and their signal peptides operative therein can be referred to as Sec dependent secretion signals. One of the issues in developing an appropriate secretion signal is to ensure that the signal is appropriately expressed and cleaved from the expressed protein.

A signature of Sec-dependent protein export is the presence of a short (about 30 amino acids), mainly hydrophobic amino-terminal signal sequence in the exported protein. The signal sequence aids protein export and is cleaved off by a periplasmic signal peptidase when the exported protein reaches the periplasm. A typical N-terminal Sec-signal peptide contains an N-domain with at least one arginine or lysine residue, followed by a domain that contains a stretch of hydrophobic residues, and a C-domain containing the cleavage site for signal peptidases.

Bacterial protein production systems have been developed in which transgenic protein constructs are engineered as fusion proteins containing both a protein of interest and a secretion signal in an attempt to target the protein out of the cytoplasm.

Strategies have been developed to excrete proteins from the cell into the supernatant. For example, U.S. Pat. No. 5,348,867 by Georgiou focuses on expression of peptides on the surface of the cell. U.S. Pat. No. 6,329,172 to the Korea Advanced Institute of Science and Technology describes an ABC transporter in *Pseudomonas fluorescens* and a method of excreting proteins extracellularly through the use of this transporter co-expressed with a protein of interest. PCT Publication No. WO 96/17943 to Novo Nordisk focuses on extracellular expression of proteins from the cell by leakage from the periplasm, using portions of the sequence of *A. lyticus* protease I or certain *Bacillus* proteases linked to proteins of interest to target them to the periplasm. PCT Publication No. WO 02/40696 and U.S. Application Publication 2003/0013150, to Boehringer Ingelheim, Int., describe the extracellular expression of proteins using the bacterial signal peptide OmpA. These publications teach that OmpA interacts with SecE alone or in combination with proteins or peptides including the amino acid sequence SEGN.

Other strategies for increased expression are directed to targeting the protein to the periplasm. Some investigations focus on non-Sec type secretion (see for e.g. PCT Publication No. WO 03/079007 to the Trustees of the University of Pennsylvania; U.S. Publication No. 2003/0180937 Georgiou, U.S. Publication No. 2003/0064435 to Weiner and Turner; and PCT Publication No. WO 00/59537 to the Research Foundation of the State University of New York). However, the majority of research has focused on the secretion of exogenous proteins with a Sec-type secretion system.

A number of secretion signals have been described for use in expressing recombinant peptides or proteins. For example, U.S. Pat. No. 5,914,254 to Celtrix Pharmaceuticals, Inc. describes increased solubility and activity of proteins using fusion partners and leader sequences that are derived from interleukin-1-like proteins.

U.S. Pat. No. 4,963,495 to Genentech describes the expression of eukaryotic proteins, particularly human growth hormone, with prokaryotic signal sequences like the sequence for *E. coli* enterotoxin. European Patent No. 0 177 343 to Genentech describes the expression of periplasmic HGH, which can be accomplished through the use of a *P. aeruginosa* enterotoxin A signal sequence.

U.S. Pat. No. 5,082,783 to Biogen describes the expression of a protein such as somatomedin C, tissue plasminogen activator or tumor necrosis factor from a promoter of at most intermediate strength, such as an actin or iso-1-cytochrome c promoter operatively linked to a DNA signal sequence, such as the Mfα1 signal sequence from yeast.

PCT Publication No. WO 89/10971 by Pastan, et al., describes the expression of *Pseudomonas* exotoxin in *E. coli* using an OmpA signal sequence, and shows the differential expression of the portions of the protein in the periplasm and the medium.

U.S. Pat. No. 6,156,552 to Novo Nordisk and describes the expression in *E. coli* or a lipase deficient *P. mendocina* of a modified *Pseudomonas lipase* using a signal sequence. The signal sequence can be an *E. coli* phoA signal sequence. U.S. Pat. Nos. 6,495,357; 6,509,181; 6,524,827; 6,528,298; 6,558,939; 6,608,018; and 6,617,143 to Novozyme also describe the production of lipases, cellulases, amylases, and other enzymes, including enzymes of Pseudomonad origin, expressed with signal sequences that are preferably native to a the expressed enzyme but can also be, for example, from a *Rhizomucor* species, the gene for the α-factor from *Saccharomyces cerevisiae* or an amylase or a protease gene from a *Bacillus* species.

U.S. Pat. Nos. 5,595,898; 5,698,435; and 6,204,023 to Xoma describe the production of chimeric antibody fragments using a pectate lyase signal peptide. The patents disclose that pectate lyase enzymes are known in various organisms, including *P. fluorescens*, however no exemplification of these sequences is provided.

U.S. Pat. No. 6,258,560 to Genentech describes the expression of a DNA-digesting protein in *E. coli* with a bacterial signal sequence which is described as preferably native to the protein but can also be selected from the group consisting of the alkaline phosphatase, penicillinase, 1pp, or heat-stable enterotoxin leader sequences. The patent also states that the protein can also be expressed in Pseuomonads, however no exemplification is given.

PCT Publication Nos. WO 01/21662, WO 02/068660 and U.S. Application Publication 2003/0044906 to Habermann and Ertl and Aventis describe secretion of hirudin derivatives from *E. coli*. One of the described signal sequences is the sequence from the OprF protein of *Pseudomonas fluorescens*. The application identified in the '662 publication is the sequence NTLGLAIGSLIAATSFGVLA, (SEQ ID NO: 1) which was described in De (1995) *FEMS Micr. Let.* 127:263-272. There is no description in the publication of using the expression plasmids in Pseudomonads, and the increase in expression of the hirudin using this strategy is only marginal when compared to control expression in *E. coli*.

U.S. Pat. No. 5,641,671 to Unilever Patent Holdings B.V. is directed to the expression of a *Pseudomonas lipase* from *P. glumae* with a stabilizing protein and preferably a signal sequence endogenous to the lipase gene.

European Patent No. EP 0 121 352 to Atkinson et al. describes a cysteine free leader sequence from *Pseudomonas* species RS-16 carboxypeptidase to be used in a vector to enhance periplasmic expression of a protein. The patent discloses cysteine residues in the signal sequence can foster interaction with the cell membrane and retard secretion. The disclosed signal sequence is MRPSIHRTAIAAV-LATAFVAGT (SEQ ID NO: 2).

Strategies that rely on signal sequences for targeting proteins out of the cytoplasm often produce improperly processed protein. This is particularly true for amino-terminal secretion signals such as those that lead to secretion through the Sec system. Proteins that are processed through this system often either retain a portion of the secretion signal, require a linking element which is often improperly cleaved, or are truncated at the terminus.

As is apparent from the above-described art, many strategies have been developed to target proteins to the periplasm of a host cell. However, known strategies have not resulted in consistently high yield of properly processed, active recombinant protein, which can be purified for therapeutic use. One major limitation in previous strategies has been the expression of proteins with poor secretion signal sequences in inadequate cell systems.

As a result, there is still a need in the art for improved large-scale expression systems capable of secreting and properly processing recombinant polypeptides to produce transgenic proteins in properly processed form. An ideal system produces high levels of soluble protein and allows targeting of that protein to the periplasm and potentially to the extracellular media.

An object of the invention is to provide a system and method of increasing expression of properly processed recombinant protein in a host cell.

Another object of the invention is to provide a system and method for increasing expression of active recombinant protein in a host cell.

Another object of the invention is to provide a commercial scale system with high levels of expression of recombinant, properly processed protein.

SUMMARY

The present invention provides improved compositions and processes for producing high levels of properly processed recombinant protein in a cell expression system. The invention is founded on the surprising discovery that *Pseudomonas fluorescens* is an improved platform for production of secreted proteins. In particular, *P. fluorescens* surprisingly produces exogenous proteins targeted to its Sec secretion system to a higher level than typically seen in other bacterial expression systems, and transports these proteins at a higher level in the periplasm of the cell, leading to increased recovery of fully processed recombinant protein. The invention includes newly identified secretion signals, derived from a *Pseudomonas fluorescens* organism, and includes peptides, vectors and expression systems incorporating these sequences, which can promote targeting of an expressed protein or peptide of interest to the periplasm of Gram-negative bacteria or into the extracellular environment. The invention also includes a *P. fluorescens* host cell which provides improved production of exogenous protein in properly processed form in the periplasm when the exogenous protein is expressed in conjunction with a signal peptide leader sequence.

In one embodiment, an isolated peptide with a sequence that is, or is substantially homologous to, a *P. fluorescens* Sec-system secretion peptide selected from a phosphate binding protein (pbp) secretion signal, an Outer Membrane Porin E (OprE) secretion signal, a Lys-Arg-Orn binding protein secretion signal, an azurin secretion signal, an iron (III) binding protein secretion signal and a lipoprotein B secretion signal.

In another embodiment, an isolated nucleic acid is provided with a sequence that encodes a peptide including a sequence that is, or is substantially homologous to, a *P. fluorescens* Sec-system secretion peptide selected from a pbp, OprE, Lys-Arg-Orn binding protein, azurin, iron (III) binding protein or a lipoprotein B secretion signal. In another embodiment, a nucleic acid is provided that hybridizes to a nucleic acid with a sequence that encodes a peptide including a sequence that is, or is substantially homologous to, a *P. fluorescens* Sec-system secretion peptide selected from a pbp, OprE, Lys-Arg-Orn binding protein, azurin, iron (III) binding protein or a lipoprotein B secretion signal. In one embodiment, the nucleic acids hybridize under strict conditions.

In one embodiment, the peptide sequence is, or is substantially homologous to, the sequence of a phosphate binding protein (pbp) secretion signal peptide of at least amino acids 2-24 (SEQ ID NO: 15) of amino acid sequence: Met Lys Leu Lys Arg Leu Met Ala Ala Met Thr Phe Val Ala Ala Gly Val Ala Thr Ala Asn Ala Val Ala. (SEQ ID NO: 4) In a separate embodiment, the nucleic acid sequence encoding the peptide is at least 80%, 85%, 90%, 95% or 98% identical to the nucleic acid sequence: atg aaa ctg aaa cgt ttg atg gcg gca atg act ttt gtc gct gct ggc gtt gcg acc gcc aac gcg gtg gcc (SEQ ID NO: 3). In another embodiment, the nucleic acid sequence of (SEQ ID NO: 3) is adjusted based on the codon usage of a host organism.

In another embodiment, the peptide sequence is, or is substantially homologous to, the sequence of an Outer Membrane Porin E (OprE) secretion signal peptide having the sequence of at least amino acids 2-21 (SEQ ID NO: 26) of amino acid sequence: Met Lys Lys Ser Thr Leu Ala Val Ala Val Thr Leu Gly Ala Ile Ala Gln Gln Ala Gly Ala (SEQ ID NO: 6). In a separate embodiment, the nucleic acid sequence encoding the peptide is at least 80%, 85%, 90%, 95% or 98% identical to the nucleic acid sequence: atg aag aag tcc acc ttg gct gtg gct gta acg ttg ggc gca atc gcc cag caa gca ggc gct (SEQ ID NO: 5). In another embodiment, the nucleic acid sequence of (SEQ ID NO: 5) is adjusted based on the codon usage of a host organism.

In another embodiment, the peptide sequence is, or is substantially homologous to, the sequence of an azurin secretion signal peptide having the sequence of at least amino acids 2-20 (SEQ ID NO: 43) of amino acid sequence: Met Phe Ala Lys Leu Val Ala Val Ser Leu Leu Thr Leu Ala Ser Gly Gln Leu Leu Ala (SEQ ID NO: 8). In a separate embodiment, the nucleic acid sequence encoding the peptide is at least 60%, 70%, 80%, 85%, 90%, 95% or 98% identical to the nucleic acid sequence: atg ttt gcc aaa ctc gtt gct gtt tcc ctg ctg act ctg gcg agc ggc cag ttg ctt gct SEQ ID NO: 7. In another embodiment, the nucleic acid sequence of SEQ ID NO: 7 is adjusted based on the codon usage of a host organism.

In another embodiment, the peptide sequence is, or is substantially homologous to, the sequence of a Lys-Arg-Orn binding protein (LAObp or KRObp) secretion signal peptide having the sequence of at least amino acids 2-23 (SEQ ID NO: 68) of amino acid sequence: Met Gln Asn Tyr Lys Lys Phe Leu Leu Ala Ala Ala Val Ser Met Ala Phe Ser Ala Thr Ala Met Ala (SEQ ID NO: 10). In a separate embodiment, the nucleic acid sequence encoding the peptide is at least 60%, 70%, 80%, 85%, 90%, 95% or 98% identical to the nucleic acid sequence: atg cag aac tat aaa aaa ttc ctt ctg gcc gcg gcc gtc tcg atg gcg ttc agc gcc acg gcc atg gca (SEQ ID NO: 9). In another embodiment, the nucleic acid sequence of SEQ ID NO; 9 is adjusted based on the codon usage of a host organism.

In yet another embodiment, the peptide sequence is, or is substantially homologous to, the sequence of an iron (III) binding protein [Fe(III)bp] secretion signal peptide having the sequence of at least amino acids 2-32 (SEQ ID NO: 79) of amino acid sequence: Met Met Ile Arg Asp Asn Arg Leu Lys Thr Ser Leu Leu Arg Gly Leu Thr Leu Thr Leu Leu Ser Leu Thr Leu Ser Pro Ala Ala His Ser (SEQ ID NO: 12). In a separate embodiment, the nucleic acid sequence encoding the peptide is at least 60%, 70%, 80%, 85%, 90%, 95% or 98% identical to the nucleic acid sequence: atg atg atc cgt gac aac cga ctc aag aca tcc ctt ctg cgc ggc ctg acc ctc acc cta ctc agc ctg acc ctg ctc tcg ccc gcg gcc cat tct (SEQ ID NO: 11). In another embodiment, the nucleic acid sequence of SEQ ID NO: 11 is adjusted based on the codon usage of a host organism.

In another embodiment, the peptide sequence is, or is substantially homologous to the sequence of a lipoprotein B (LprB) secretion signal peptide having the sequence of at least amino acids 2-17 (SEQ ID NO: 90) of amino acid sequence: Met Ile Lys Arg Asn Leu Leu Val Met Gly Leu Ala Val Leu Leu Ser Ala (SEQ ID NO: 14). In a separate embodiment, the nucleic acid sequence encoding the peptide is at least 60%, 70%, 80%, 85%, 90%, 95% or 98% identical to the nucleic acid sequence: atg atc aaa cgc aat ctg ctg gtt atg ggc ctt gcc gtg ctg ttg agc gct (SEQ ID NO: 13). In another embodiment, the nucleic acid sequence of SEQ ID NO: 13 is adjusted based on the codon usage of a host organism.

Another embodiment is an expression vector which includes a nucleic acid of a *P. fluorescens* Sec-system secretion peptide with a sequence that is, or is substantially homologous to, a pbp, OprE, Lys-Arg-Orn binding protein, azurin, iron (III) binding protein or a lipoprotein B secretion signal, operably linked to a promoter. In another embodiment, the vector further comprises a coding sequence for expression of a recombinant protein or peptide of interest. In one embodiment, the expression vector further comprises a tag sequence adjacent to the coding sequence for the secretion signal or to the coding sequence for the recombinant protein or peptide.

Cells are also provided which includes the expression vector. In one embodiment, the cell expresses a recombinant protein linked to a *P. fluorescens* Sec-system secretion signal as described herein. The cell may express the protein in a periplasm compartment. In certain embodiments, the cell may also produce recombinant protein extracellularly through an outer cell wall. In one embodiment, the cell is a bacterial cell, and in certain sub-embodiments, the cell is a *P. fluorescens* cell or an *E. coli* cell. In other embodiments, the cell is a eukaryotic cell, and can be a yeast cell, an insect cell, a mammalian cell or a plant cell.

In one embodiment, the host cell is a bacterial cell. In another embodiment, the cell is a Pseudomonad and in a specific embodiment, the cell is a *Pseudomonas fluorescens* cell.

In another embodiment, an improved process and system for preparing a recombinant protein in a host cell is provided. The improvement includes the expression of a *P. fluorescens* Sec-system secretion peptide that is, or is substantially homologous to, a peptide selected from a pbp, OprE, Lys-Arg-Orn binding protein, azurin, iron (III) binding protein or a lipoprotein B secretion signal, operably linked to a recombinant protein or peptide of interest in a host cell. In one embodiment, the expression occurs at high density cell culture. The Sec-secretion signal may be cleaved from the mature protein in the cell. In another embodiment, the secretion signal is not cleaved and the cell expresses a recombinant protein linked to the secretion signal. In one embodiment, a tag sequence is operably linked to the protein of interest.

In a separate embodiment, a process is provided for preparing recombinant exogenous secreted proteins by expressing a protein linked to a Sec-system secretion signal in *P. fluorescens*. This embodiment is based on the recognition of *P. fluorescens* as an improved expression platform for expression of secreted proteins. In one embodiment, the Sec-secretion signal is derived from a *P. fluorescens* genome, however in another embodiment, the Sec-secretion signal is derived from an *E. coli* genome. In other embodiments, the secretion signal may be native to the protein being expressed.

In one embodiment, the host cell has a periplasm and expression of the Sec-system peptide can target the recombinant protein to the periplasm of the cell. In a subembodiment, the expression leads to production of extracellular protein. The process may also include the step of purifying the recombinant protein from the periplasm or from extracellular media. The Sec-signal can be expressed linked to the protein and the signal-linked protein can be purified from the cell. Therefore, in one embodiment, this isolated peptide is a fusion protein of the secretion signal and a protein or peptide of interest. However, the secretion signal can also be cleaved from the protein when the protein is targeted to the periplasm. In one embodiment, the linkage between the Sec-system secretion signal and the protein or peptide is modified to increase cleavage of the secretion signal.

In one embodiment, the process can produce properly processed recombinant protein in the cell. In another embodiment, the expression of the Sec-system peptide may produce active recombinant protein in the cell. The process of the invention may also lead to increased yield of recombinant protein as compared to when the protein is expressed without the Sec-secretion signal.

In one embodiment, the process produces at least 0.1 g/L correctly processed protein. In another embodiment, the process produces 0.1 to 1 g/L correctly processed protein in the cell. In subembodiments, the total protein produced can be at least about 2.0 to about 50.0 g/L. In some embodiments, the amount of correctly processed protein produced is at least about 5%, about 10%, about 15%, about 20%, about 25%, or more of total recombinant protein produced.

The protein or peptide of interest may be a therapeutically useful protein or peptide. In one embodiment, the protein or peptide is derived from a eukaryotic species. In another embodiment, the protein sequence is derived from a mammalian sequence. In another embodiment, the active form of the protein includes at least one disulfide bond. In yet another embodiment, the protein or peptide is a derived from a hormone, a growth factor, an extracellular receptor or ligand, a protease, a kinase, a blood protein, a chemokine or cytokine or an antibody.

BRIEF DESCRIPTION OF THE FIGURES

FIG. 2: *P. fluorescens* gal2 secretion constructs. Plamids maps for pDOW1122 and DOW1123 are shown (A) pDOW1122 contains the oprF:gal2 fusion (amino acid sequence shown in B) (SEQ ID NO: 117) and pDOW1123 contains the pbp:gal2 fusion (amino acid sequence shown in C) (SEQ ID NO: 118). The * indicates the predicted signal peptidase cleavage site.

FIG. 3: Secreted expression of Gal2. An image of an SDS-PAGE analysis of whole broth samples (A) from *P. fluorescens* expressing either oprF:gal2 (pDOW1122) or pbp:gal2 (pDOW1123). A 1/80 dilution of whole broth was loaded onto a 10% NuPAGE gel and run in 1×MOPS buffer. Western analysis of soluble (S), insoluble (I), and cell free culture supernatant (SN) fractions is shown in B. The amount of culture loaded, normalized to A575=30, is indicated below the gel.

FIG. 6: Secreted expression of anti-digoxin scFv. A: shows secretion in *P. fluorescens* at the shake flask scale. B: shows secretion in *E. coli* at the shake flask scale. All samples were normalized to 20 OD (OD575 for *P. fluorescens* and OD600 for *E. coli*). The samples were run on a 4-12% BT gel in MES Buffer. S=soluble, I=insoluble. The numbers are post induction times in hours.

FIG. 7: Western blots of secreted anti-digoxin scFv at the shake flask scale. Panel A shows *P. fluorescens* expressed protein and panel B shows *E. coli* expressed protein. Samples were normalized to 20 OD. The protein is 100% insoluble in both constructs. S=soluble, I=insoluble. 0, 3, 24, 48 represent time post induction.

FIG. 11: Amino acid sequence of the processed and unprocessed Skp protein. Underlined sequence corresponds to signal sequence (top) (SEQ ID NO: 119) and sequence identified by MALDI-PSD (lower) (SEQ ID NO: 120).

DETAILED DESCRIPTION

Figure 1:
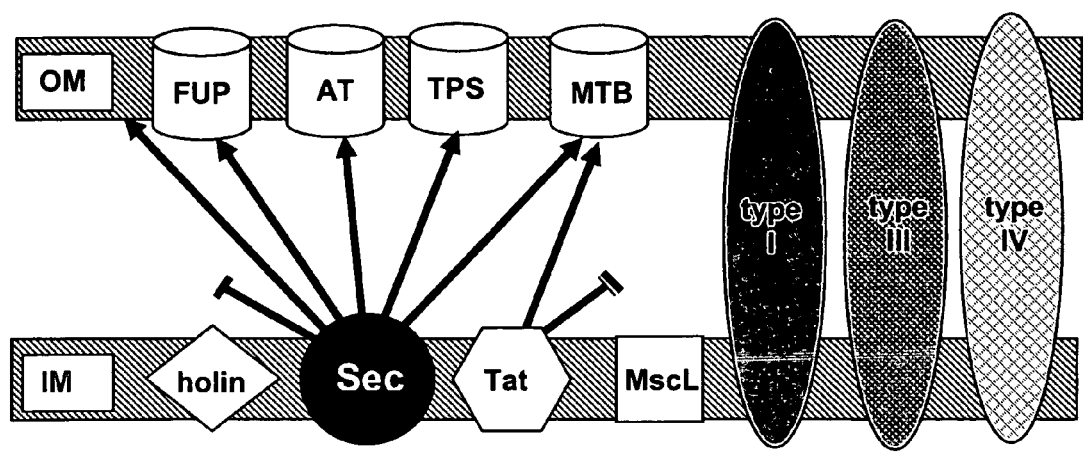
FIG. 1: Overview of protein secretion systems in Gram-negative bacteria. Four systems (Sec, Tat, MscL and holins) translocate only across the inner membrane. Proteins secreted by the Sec system are located in the periplasm, integrated into the outer membrane, or transported across the outer membrane by one of the four outer membrane secretion systems as indicated with arrows. Proteins translocated by the Tat system are mainly located in the periplasm, but a few proteins in *P. aeruginosa* have been found to be further exported by the MTB system. Holins and MscL only transport proteins into the periplasm. Types I, III and IV systems export proteins across both membranes without any periplasmic intermediates. Abbreviations: FUP, fimbrial usher porin; AT, autotransporter; TPS, two-partner secretion system; MTB, main terminal branch; IM, inner membrane; OM, outer membrane.

The invention is based on the discovery of secretion signal sequences in *P. fluorescens*. In one embodiment, the invention provides signal peptide sequences, nucleic acids encoding signal peptides, vectors and cells including nucleic acids encoding signal peptide sequences which are derived from a *P. fluorescens* organism that can enhance secretion of a protein or peptide of interest when expressed in conjunction with the protein or peptide. Improved processes for producing high levels of properly processed recombinant protein in a cell expression system using *P. fluorescens* derived Sec-secretion signals are also provided.

The invention is also the recognition that *P. fluorescens* is an improved platform for production of a variety of proteins. In particular, *P. fluorescens* produces exogenous proteins targeted to the Sec secretion system in a correctly processed form to a higher level than typically seen in other bacterial expression systems, and transports these proteins at a higher level to the periplasm of the cell, leading to increased recovery of fully processed recombinant protein. Therefore, in one embodiment, the invention provides a process for producing exogenous protein in a *P. fluorescens* cell by expressing the target protein linked to a Sec secretion signal.

It has been previously demonstrated that certain Pseudomonads offer advantages for commercial expression of peptides and enzymes, in comparison with other bacterial expression systems. In particular, *P. fluorescens* has been identified as an advantageous expression system. *P. fluorescens* encompasses a group of common, nonpathogenic saprophytes that colonize soil, water and plant surface environments. Commercial enzymes derived from *P. fluorescens* have been used to reduce environmental contamination, as detergent additives, and for stereoselective hydrolysis. *P. fluorescens* is also used agriculturally to control pathogens. Mycogen, which was acquired in its entirety by Dow Agro-Sciences in the late 1990's, began expressing recombinant bacterial proteins in *P. fluorescens* in the mid-1980's and filed its first patent application on the expression of the *Bacillus thuringiensis* toxin in *P. fluorescens* on Jan. 22, 1985 ("Cellular encapsulation of biological pesticides"). Between 1985 and 2004, Mycogen, later Dow Agro Sciences, as well as other companies, capitalized on the agricultural use of *P. fluorescens* in patent applications on the production of pesticidal, insecticidal, and nematocidal toxins, as well as on specific toxic sequences and genetic manipulation to enhance expression of these.

DowPharma currently has several pending patent applications in the area of use of *P. fluorescens* to produce recombinant proteins. PCT Application Nos. WO 03/068926 and WO 03/068948 to Dow Global Technologies describe extremoyzme over-expression systems in which Pseudomonads, specifically *P. fluorescens*, can be used as host cells. The publications generally disclose the expression of the extremozymes in conjunction with a signal peptide but specific sequences are not disclosed and there is no recognition that the cells are superior for secretion.

PCT publication No. WO 03/089455 to Dow Global Technologies, filed Apr. 22, 2003, entitled "Low-Cost Production of Peptides" describes a low cost method of producing small peptides, such as antimicrobial peptides, as contatemeric precursors in Pseudomonads, specifically *P. fluorescens*. The publication discloses the expression of concatameric peptides in conjunction with a signal peptide but specific sequences are not disclosed.

PCT Application No. WO 04/005221 to Dow Global Technologies, entitled "Benzoate and Antranilate Inducible Promoters" provides benzoate or anthranilate inducible promoters from *P. fluorescens* for commercial prokaryotic fermentation systems. The publication discloses the inclusion of a signal peptide with the promoter, but specific signal sequences are not disclosed.

Peptides

In one embodiment, an isolated peptide is provided, with an amino acid sequence that is, or is substantially homologous to, a *Pseudomonas fluorescens* Sec-system secretion peptide selected from a phosphate binding protein (pbp) secretion signal, an Outer Membrane Porin E (OprE) secretion signal, a Lys-Arg-Orn binding protein secretion signal, an azurin secretion signal, an iron (III) binding protein secretion signal and a lipoprotein B secretion signal.

In another embodiment, an isolated peptide with an amino acid sequence that is, or is substantially homologous to, a pbp, OprE, Lys-Arg-Orn binding protein, azurin, iron (III) binding protein or a lipoprotein B secretion signal is provided. In one embodiment, this isolated peptide is a fusion protein of the secretion signal and a protein or peptide of interest.

In one embodiment, the peptide sequence is that is, or is substantially homologous to, the sequence of a phosphate binding protein (pbp) secretion signal peptide of at least amino acids: Met Lys Leu Lys Arg Leu Met Ala Ala Met Thr Phe Val Ala Ala Gly Val Ala Thr Ala Asn Ala Val Ala (SEQ ID NO: 4). In another embodiment, the peptide sequence comprises at least amino acids 2-24 (SEQ ID NO: 15) of (SEQ ID NO: 4). In another embodiment, the peptide sequence comprises a truncation of (SEQ ID NO: 4), which is truncated by 1, 2, 3, 4, 5, 6, 7, 8, 9, or 10 amino acids from the amino terminal but retains secretion signal activity (SEQ ID NOs: 16-25 respectively).

In another embodiment, the peptide sequence is that is, or is substantially homologous to, the sequence of an Outer Membrane Porin E (OprE) secretion signal peptide having the sequence of at least amino acids: Met Lys Lys Ser Thr Leu Ala Val Ala Val Thr Leu Gly Ala Ile Ala Gln Gln Ala Gly Ala (SEQ ID NO: 6). In one embodiment, the peptide is, or is homologous to at least amino acids 2-21 (SEQ ID NO: 26) of (SEQ ID NO: 6). In another embodiment, the peptide sequence comprises a truncation of (SEQ ID NO: 6), which is truncated by 1, 2, 3, 4, 5, 6, 7, 8, 9, or 10 amino acids from the amino terminal but retains secretion signal activity (SEQ ID NOs: 27-36 respectively). In one embodiment, the peptide of (SEQ ID NO: 6) is modified so that Lys at position 2 is replaced with Tyr (SEQ ID NO: 37). In one embodiment, the peptide of SEQ ID NO: 6 is modified so that Thr at position 5 is replaced with Ser (SEQ ID NO: 38). In one embodiment, the peptide of SEQ ID NO: 3 (SEQ ID NO: 6) is modified so that Val at position 8 is replaced with Leu (SEQ ID NO: 39).

In one embodiment, the peptide of SEQ ID NO: 6) is modified so that Val at position 10 is replaced with Val and Arg (SEQ ID NO: 40). In one embodiment, the peptide of (SEQ ID NO: 6) is modified so that Ala at position 14 is replaced with Val (SEQ ID NO: 41). In one embodiment, the peptide of: (SEQ ID NO: 6) is modified so that Ile at position 15 is replaced with Leu (SEQ ID NO: 42).

In another embodiment, the peptide sequence is that is, or is substantially homologous to, the sequence of an azurin secretion signal peptide having the sequence of at least amino acids: Met Phe Ala Lys Leu Val Ala Val Ser Leu Leu Thr Leu Ala Ser Gly Gln Leu Leu Ala) (SEQ ID NO: 8). In one embodiment, the peptide is, or is homologous to at least amino acids 2-20 (SEQ ID NO: 43) of SEQ ID NO: 8. In another embodiment, the peptide sequence comprises a truncation of SEQ ID NO: 8, which is truncated by 1, 2, 3, 4, 5, 6, 7, 8, 9, or 10 amino acids from the amino terminal but retains secretion signal activity (SEQ ID NOs: 44-53 respectively). In one embodiment, the peptide of SEQ ID NO: 8 is modified so that Phe-Ala at position 2 and 3 are replaced with Leu-Arg (SEQ ID NO: 54) or Ile-Arg (SEQ ID NO: 55). In one embodiment, the peptide of SEQ ID NO: 8 is modified so that Leu at position 5 is replaced with Ala (SEQ ID NO: 56). In one embodiment, the peptide of SEQ ID NO: 8 is modified so that Val at position 6 is replaced with Ala (SEQ ID NO: 57). In one embodiment, the peptide of 5 SEQ ID NO: 8 is modified so that Val-Ala-Val at positions 6-8 are replaced with Ile-Ser-Ala (SEQ ID NO; 58). In one embodiment, the peptide of SEQ ID NO: 8 is modified so that Leu at position 11 is replaced with Ile (SEQ ID NO: 59). In one embodiment, the peptide of SEQ ID NO: 8 is modified so that Thr at position 12 is replaced with Ser (SEQ ID NO: 60). In one embodiment, the peptide of 5 SEQ ID NO: 8 is modified so that Ala at position 14 is replaced with Leu (SEQ ID NO: 61) or Phe (SEQ ID NO: 62). In one embodiment, the peptide of SEQ ID NO: 8 is modified so that Gly at position 16 is replaced with Ala (SEQ ID NO: 63). In one embodiment, the peptide of SEQ ID NO: 8 is modified so that Gln at position 17 is replaced with Ser (SEQ ID NO: 64) or Pro (SEQ ID NO: 65). In one embodiment, the peptide of SEQ ID NO: 8 is modified so that Leu at position 18 is replaced with Val (SEQ ID NO: 66). In one embodiment, the peptide of SEQ ID NO: 8 is modified so that Leu-Leu at positions 18-19 are replaced with Val-Phe (SEQ ID NO: 67).

In another embodiment, the peptide sequence is, or is substantially homologous to, the sequence of a Lys-Arg-Orn binding protein (LAObp or KRObp) secretion signal peptide having the sequence of at least amino acids: Met Gln Asn Tyr Lys Lys Phe Leu Leu Ala Ala Ala Val Ser Met Ala Phe Ser Ala Thr Ala Met Ala (SEQ ID NO: 10). In one embodiment, the peptide is, or is substantially homologous to, amino acids 2-23 (SEQ ID NO: 68) of SEQ ID NO: 10. In another embodiment, the peptide sequence comprises a truncation of SEQ ID NO: 7, which is truncated by 1, 2, 3, 4, 5, 6, 7, 8, 9, or 10 (SEQ ID NOs: 69-78) amino acids from the amino terminal but retains secretion signal activity.

In yet another embodiment, the peptide sequence is, or is substantially homologous to, the sequence of an iron (III) binding protein [Fe(III)bp] secretion signal peptide having the sequence of at least amino acids: Met Met Ile Arg Asp Asn Arg Leu Lys Thr Ser Leu Leu Arg Gly Leu Thr Leu Thr Leu Leu Ser Leu Thr Leu Leu Ser Pro Ala Ala His Ser (SEQ ID NO: 12). In one embodiment, the peptide is, or is substantially homologous to, amino acids 2-32 (SEQ ID NO: 79) of SEQ ID NO: 12. In another embodiment, the peptide sequence comprises a truncation of SEQ ID NO: 12, which is truncated by 1, 2, 3, 4, 5, 6, 7, 8, 9, or 10 (SEQ ID NOs: 80-89) amino acids from the amino terminal but retains secretion signal activity.

In another embodiment, the peptide sequence is, or is substantially homologous to, the sequence of a lipoprotein B (LprB) secretion signal peptide having the sequence of at least amino acids: Met Ile Lys Arg Asn Leu Leu Val Met Gly Leu Ala Val Leu Leu Ser Ala (SEQ ID NO: 14). In one embodiment, the peptide is, or is substantially homologous to, amino acids 2-17 (SEQ ID NO: 90) of SEQ ID NO: 14. In another embodiment, the peptide sequence comprises a truncation of SEQ ID NO: 14, which is truncated by 1, 2, 3, 4, 5, 6, 7, 8, 9, or 10 (SEQ ID NOs: 91-100) amino acids from the amino terminal but retains secretion signal activity In a separate embodiment, the secretion signal is a secretion signal derived from an *E. coli* protein. In one embodiment, the secretion signal is a native signal sequence for an *E. coli* derived protein. In one embodiment, the protein is a chaperone protein. The protein can be a disulfide bond forming protein. In one embodiment, the sequence is the native sequence of an *E. coli* chaperone protein such as a skp protein.

Signal peptides for the sec pathway generally consist of the following three domains: (i) a positively charged n-region, (ii) a hydrophobic h-region and (iii) an uncharged but polar c-region. The cleavage site for the signal peptidase is located in the c-region. However, the degree of signal sequence conservation and length, as well as the cleavage site position, can vary between different proteins. The secretion signal sequence can, for example, be any sequence that is identified by using a computer program designed to identify secretion signals, such as the SignalP program or as described in Hiller, et al. (2004) *Nucleic Acids Research* 32 (Web Server issue): W375-W379; available on the internet at www.predisi.de.

Sequence Homology

As used herein, the term "homologous" or means either i) a protein or peptide that has an amino acid sequence that is substantially similar (i.e., at least 70%, 75%, 80%, 85%, 90%, 95%, or 98%) to the sequence of a given original protein or peptide and that retains a desired function of the original protein or peptide or ii) a nucleic acid that has a sequence that is substantially similar (i.e., at least 60%, 65%, 70%, 75%, 80%, 85%, 90%, 95%, or 98%) to the sequence of a given nucleic acid and that retains a desired function of the original nucleic acid sequence. In all of the embodiments of this invention and disclosure, any disclosed protein, peptide or nucleic acid can be substituted with a homologous or substantially homologous protein, peptide or nucleic acid that retains a desired function. In all of the embodiments of this invention and disclosure, when any nucleic acid is disclosed, it should be assumed that the invention also includes all nucleic acids that hybridize to the disclosed nucleic acid.

In one embodiment the amino acid sequence of the homologous polypeptide is a variant of a given original polypeptide, wherein the sequence of the variant is obtainable by replacing up to or about 30% of the original polypeptide's amino acid residues with other amino acid residue(s), including 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30%, provided that the substituted variant retains a desired function of the original polypeptide. A variant amino acid with substantial homology will be at least about 70% homologous to the given polypeptide, or 70, 75, 80, 85, 90, 95, 98, 99 or 100% homologous.

In one embodiment, a variant will be similarly substituted or a similar variant of the original polypeptide. The term "similarly substituted variant" means a variant containing, relative to the original polypeptide, different residues that are "similar" amino acid residue substitutions, but in which not all differences are "similar" substitutions. As used herein, the term "similar variant" means a variant in which each of the different residues is a "similar" amino acid residue substitution. As used in this context, the term "similar" amino acid residue refers to those residues that are members of any one of the 15 conservative or semi-conservative groups shown in Table 1.

TABLE 1

Similar Amino Acid Substitution Groups

| Conservative Groups (8) | Semi-Conservative Groups (7) |
|---|---|
| Arg, Lys | Arg, Lys, His |
| Asp, Glu | Asn, Asp, Glu, Gln |
| Asn, Gln | |
| Ile, Leu, Val | Ile, Leu, Val, Met, Phe |
| Ala, Gly | Ala, Gly, Pro, Ser, Thr |
| Ser, Thr | Ser, Thr, Tyr |
| Phe, Tyr | Phe, Trp, Tyr |
| Cys (non-cystine), Ser | Cys (non-cysteine), Ser, Thr |

In one embodiment, at least 50% of the substitutions will appear as conservative amino acid substitutions, and the remainder of the substitutions will be semi-conservative substitutions. In other embodiments, at least 60%, or at least 70%, or at least 75%, or at least 80%, or at least 85%, or at least 90% of the similar substitutions will appear as conservative amino acid substitutions.

In another embodiment, at least 50% of the similar substitutions will appear as conservative amino acid substitutions, with the remainder of the similar substitutions appearing as semi-conservative substitutions. In other embodiments, at least 55%, or at least 60%, or at least 65%, or at least 70%, or at least 75%, or at least 80% of the similar substitutions will appear as conservative amino acid substitutions. In one embodiment, a substituted variant will be a similar variant of a given original polypeptide.

Nucleic Acid Sequences

The invention also includes isolated nucleic acids with a sequence that encodes a peptide including a sequence substantially homologous to a pbp, OprE, Lys-Arg-Orn binding protein, azurin, iron (III) binding protein or a lipoprotein B secretion signal is provided. In another aspect of the invention, a nucleic acids that hybridizes to an isolated nucleic acids with a sequence that encodes a peptide including a sequence substantially homologous to a pbp, OprE, Lys-Arg-Orn binding protein, azurin, iron (III) binding protein or a lipoprotein B secretion signal is provided. In certain embodiments, the hybridizing nucleic acid will bind under high stringency conditions. The high stringency conditions typically mean hybridization at 68° C. or more.

In one embodiment, a nucleic acid is provided that encodes a peptide sequence substantially homologous to the sequence of a phosphate binding protein (pbp) secretion signal peptide of at least amino acids 2-24 (SEQ ID NO: 15) of (SEQ ID NO: 4). In a separate embodiment, the nucleic acid sequence encoding the peptide is: atg aaa ctg aaa cgt ttg atg gcg gca atg act ttt gtc gct gct ggc gtt gcg acc gcc aac gcg gtg gcc (SEQ ID NO: 3). In another embodiment, the nucleic acid sequence is at least 80%, 85%, 90%, 95% or 98% identical to the sequence of SEQ ID NO: 3. In another embodiment, the nucleic acid sequence is at least 90%, 85%, 80%, 75%, 70%, 65%, 60%, 55% or 50% identical to the sequence of SEQ ID NO: 3. In another embodiment, the nucleic acid sequence of SEQ ID NO: 3 is adjusted based on the codon usage of a host organism.

In another embodiment, a nucleic acid is provided that encodes a peptide sequence substantially homologous to the sequence of an Outer Membrane Porin E (OprE) secretion signal peptide having the sequence of at least amino acids 2-21 (SEQ ID NO: 26) of (SEQ ID NO: 6). In one embodiment, the peptide sequence is, or is substantially homologous to, a peptide of SEQ ID NO: 6 wherein Lys at position 2 is replaced with Tyr (SEQ ID NO: 37); wherein Thr at position 5 is replaced with Ser (SEQ ID NO: 38); wherein Val at position 8 is replaced with Leu (SEQ ID NO: 39); wherein Val at position 10 is replaced with Val and Arg (SEQ ID NO: 40); wherein Ala at position 14 is replaced with Val (SEQ ID NO: 41); wherein Ile at position 15 is replaced with Leu (SEQ ID NO: 42). In a separate embodiment, the nucleic acid sequence encoding the peptide is: atg aag aag tcc acc ttg gct gtg gct gta acg ttg ggc gca atc gcc cag caa gca ggc gct (SEQ ID NO: 5). In another embodiment, the nucleic acid sequence is at least 90% identical to the sequence of SEQ ID NO: 5. In another embodiment, the nucleic acid sequence is at least 98%, 95%, 90%, 85%, 80%, 75%, 70%, 65%, 60%, 55% or 50% identical to the sequence of SEQ ID NO: 5. In another embodiment, the nucleic acid sequence of SEQ ID NO: 5 is adjusted based on the codon usage of a host organism.

In another embodiment, a nucleic acid is provided that encodes a peptide sequence substantially homologous to the sequence of an azurin secretion signal peptide having the sequence of at least amino acids 2-20 (SEQ ID NO: 43) of SEQ ID NO: 8. In one embodiment, the peptide sequence is, or is substantially homologous to, a peptide of SEQ ID NO: 8 wherein Phe-Ala at position 2 and 3 are replaced with Leu-Arg (SEQ ID NO: 54) or Ile-Arg (SEQ ID NO: 55); wherein Leu at position 5 is replaced with Ala (SEQ ID NO: 56); wherein Val at position 6 is replaced with Ala (SEQ ID NO: 57); wherein Val-Ala-Val at positions 6-8 are replaced with Ile-Ser-Ala (SEQ ID NO: 58); wherein Leu at position 11 is replaced with Ile (SEQ ID NO: 59); wherein Thr at position 12 is replaced with Ser (SEQ ID NO: 60); wherein Ala at position 14 is replaced with Leu (SEQ ID NO: 61) or Phe (SEQ ID NO: 62); wherein Gly at position 16 is replaced with Ala (SEQ ID NO: 63); wherein Gln at position 17 is replaced with Ser (SEQ ID NO: 64) or Pro (SEQ ID NO: 65); wherein Leu at position 18 is replaced with Val (SEQ ID NO: 66); or wherein Leu-Leu at positions 18-19 are replaced with Val-Phe (SEQ ID NO: 67). In a separate embodiment, the nucleic acid sequence encoding the peptide is: atg ttt gcc aaa ctc gtt gct gtt tcc ctg ctg act ctg gcg agc ggc cag ttg ctt gct (SEQ ID NO: 7). In another embodiment, the nucleic acid sequence is at least 90% identical to the sequence of SEQ ID NO: 7. In another embodiment, the nucleic acid sequence is at least 98%, 95%, 90%, 85%, 80%, 75%, 70%, 65%, 60%, 55% or 50% identical to the sequence of SEQ ID NO: 7. In another embodiment, the nucleic acid sequence of SEQ ID NO: 7 is adjusted based on the codon usage of a host organism.

In another embodiment, a nucleic acid is provided that encodes a peptide sequence substantially homologous to the sequence of a Lys-Arg-Orn binding protein (LAObp or KRObp) secretion signal peptide having the sequence of at least amino acids 2-23 (SEQ ID NO: 68) of (SEQ ID NO: 10). In a separate embodiment, the nucleic acid sequence encoding the peptide is: atg cag aac tat aaa aaa ttc ctt ctg gcc gcg gcc gtc tcg atg gcg ttc agc gcc acg gcc atg gca (SEQ ID NO: 9). In another embodiment, the nucleic acid sequence is at least 90% identical to the sequence of SEQ ID NO: 9. In another embodiment, the nucleic acid sequence is at least 98%, 95%, 90%, 85%, 80%, 75%, 70%, 65%, 60%, 55% or 50% identical to the sequence of SEQ ID NO: 9. In another embodiment, the nucleic acid sequence of SEQ ID NO: 9 is adjusted based on the codon usage of a host organism.

In yet another embodiment, a nucleic acid is provided that encodes a peptide sequence substantially homologous to the sequence of an iron (III) binding protein [Fe(III)bp] secretion signal peptide having the sequence of at least amino acids 2-32 (SEQ ID NO: 79) of (SEQ ID NO: 12). In a separate embodiment, the nucleic acid sequence encoding the peptide is: atg atg atc cgt gac aac cga ctc aag aca tcc ctt ctg cgc ggc ctg acc ctc acc cta ctc agc ctg acc ctg ctc tcg ccc gcg gcc cat tct (SEQ ID NO: 11). In another embodiment, the nucleic acid sequence is at least 90% identical to the sequence of SEQ ID NO: 11. In another embodiment, the nucleic acid sequence is at least 98%, 95%, 90%, 85%, 80%, 75%, 70%, 65%, 60%, 55% or 50% identical to the sequence of SEQ ID NO: 11. In another embodiment, the nucleic acid sequence of SEQ ID NO: 11 is adjusted based on the codon usage of a host organism.

In another embodiment, a nucleic acid is provided that encodes a peptide sequence substantially homologous to the sequence of a lipoprotein B (LprB) secretion signal peptide having the sequence of at least amino acids 2-17 (SEQ ID NO: 90) of SEQ ID NO: 14. In a separate embodiment, the nucleic acid sequence encoding the peptide is: atg atc aaa cgc aat ctg ctg gtt atg ggc ctt gcc gtg ctg ttg agc gct (SEQ ID NO: 13). In another embodiment, the nucleic acid sequence is at least 90% identical to the sequence of SEQ ID NO: 13. In another embodiment, the nucleic acid sequence is at least 98%, 95%, 90%, 85%, 80%, 75%, 70%, 65%, 60%, 55% or 50% identical to the sequence of SEQ ID NO: 13. In another embodiment, the nucleic acid sequence of SEQ ID NO: 13 is adjusted based on the codon usage of a host organism.

Codon usage or codon preference is well known in the art. The selected coding sequence may be modified by altering the genetic code thereof to match that employed by the bacterial host cell, and the codon sequence thereof may be enhanced to better approximate that employed by the host. Genetic code selection and codon frequency enhancement may be performed according to any of the various methods known to one of ordinary skill in the art, e.g., oligonucleotide-directed mutagenesis. Useful on-line InterNet resources to assist in this process include, e.g.: (1) the Codon Usage Database of the Kazusa DNA Research Institute (2-6-7 Kazusa-kamatari, Kisarazu, Chiba 292-0818 Japan) and available on the internet at www.kazusa.or.jp/codon/; and (2) the Genetic Codes tables available from the NCBI Taxonomy database on the internet at www.ncbi.nln.nih.gov/Taxonomy/Utils/wprintgc.cgi?mode=c. For example, *Pseudomonas* species are reported as utilizing Genetic Code Translation Table 11 of the NCBI Taxonomy site, and at the Kazusa site as exhibiting the codon usage frequency of the table shown on the internet at www.kazusa.or.ip/codon/cgibin/.

Nucleic Acid Homology

It is apparent to one of skill in the art that a variety of substantially homologous nucleic acids can be provided that encode sequences of substantially similar peptides. In the case of homology for coding sequences, a coding sequence homologous to a protein-encoding nucleic acid sequence hereof will contain no more than 30% (i.e. 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30%) mutations that cause a change in reading frame and none that create a premature stop codon, as compared to the protein-encoding nucleic acid sequence disclosed herein. However, the nucleic acid sequences can be designed based on differing codon usage in the desired expression systems.

Nucleic Sequence homology is determined according to any of various methods well known in the art. Examples of useful sequence alignment and homology determination methodologies include those described below.

Alignments and searches for homologous sequences can be performed using the U.S. National Center for Biotechnology Information (NCBI) program, MegaBLAST (currently available on the internet at www.ncbi.nlm.nih.gov/BLAST/). Use of this program with options for percent identity set at 70% for amino acid sequences, or set at 90% for nucleotide sequences, will identify those sequences with 70%, or 90%, or greater homology to the query sequence. Other software known in the art is also available for aligning and/or searching for homologous sequences, e.g., sequences at least 70% or 90% homologous to an information string containing a promoter base sequence or activator-protein-encoding base sequence according to the present invention. For example, sequence alignments for comparison to identify sequences at least 70% or 90% homologous to a query sequence can be performed by use of, e.g., the GAP, BESTFIT, BLAST, FASTA, and TFASTA programs available in the GCG Sequence Analysis Software Package (available from the Genetics Computer Group, University of Wisconsin Biotechnology Center, 1710 University Avenue, Madison, Wis. 53705), with the default parameters as specified therein, plus a parameter for the extent of homology set at 70% or 90%. Also, for example, the CLUSTAL program (available in the PC/Gene software package from Intelligenetics, Mountain View, Cal.) may be used.

These and other sequence alignment methods are well known in the art and may be conducted by manual alignment, by visual inspection, or by manual or automatic application of a sequence alignment algorithm, such as any of those embodied by the above-described programs. Various useful algorithms include, e.g.: the similarity search method described in W. R. Pearson & D. J. Lipman, *Proc. Nat'l Acad. Sci. USA* 85:2444-48 (April 1988); the local homology method described in T. F. Smith & M. S. Waterman, in *Adv. Appl. Math.* 2:482-89 (1981) and in *J. Molec. Biol.* 147:195-97 (1981); the homology alignment method described in S. B. Needleman & C. D. Wunsch, *J. Molec. Biol.* 48 (3):443-53 (March 1970); and the various methods described, e.g., by W. R. Pearson, in *Genomics* 11 (3):635-50 (November 1991); by W. R. Pearson, in *Methods Molec. Biol.* 24:307-31 and 25:365-89 (1994); and by D. G. Higgins & P. M. Sharp, in *Comp. Appl'ns in Biosci.* 5:151-53 (1989) and in *Gene* 73 (1):237-44 (15 Dec. 1988).

Nucleic acid hybridization performed under highly stringent hybridization conditions is also a useful technique for obtaining sufficiently homologous sequences for use herein. Highly stringent hybridization conditions generally means hybridization performed in aqueous conditions at least 68° C.

Vectors

Another embodiment is an expression vector which includes a nucleic acid of a *P. fluorescens* Sec-system secretion peptide with a sequence substantially homologous to a pbp, OprE, Lys-Arg-Orn binding protein, azurin, iron (III) binding protein or a lipoprotein B secretion signal, operably linked to a promoter. Expressible coding sequences will be operatively attached to a transcription promoter capable of functioning in the chosen host cell, as well as all other required transcription and translation regulatory elements.

The term "operably attached" refers to any configuration in which the transcriptional and any translational regulatory elements are covalently attached to the encoding sequence in such disposition(s), relative to the coding sequence, that in and by action of the host cell, the regulatory elements can direct the expression of the coding sequence.

The vector will typically comprise one or more phenotypic selectable markers and an origin of replication to ensure maintenance of the vector and to, if desirable, provide amplification within the host. Suitable hosts for transformation in accordance with the present disclosure include various species within the genera *Pseudomonas*, and particularly preferred is the host cell strain of *P. fluorescens*.

In one embodiment, the vector further comprises a coding sequence for expression of a recombinant protein or peptide of interest, operably attached to the Sec secretion signal. The recombinant proteins and peptides can be expressed from polynucleotides in which the target polypeptide coding sequence is operably attached to the leader sequence and transcription and translation regulatory elements to form a functional gene from which the host cell can express the protein or peptide. The coding sequence can be a native coding sequence for the target polypeptide, if available, but will more preferably be a coding sequence that has been selected, improved, or optimized for use in the selected expression host cell: for example, by synthesizing the gene to reflect the codon use bias of a host species. In one embodiment of the invention, the host species is a *P. fluorescens*, and the codon bias of *P. fluorescens* is taken into account when designing both the signal sequence and the protein or peptide sequence. The gene(s) are constructed within or inserted into one or more vector(s), which can then be transformed into the expression host cell.

Other regulatory elements may be included in a vector (also termed "expression construct"). Such elements include, but are not limited to, for example, transcriptional enhancer sequences, translational enhancer sequences, other promoters, activators, translational start and stop signals, transcription terminators, cistronic regulators, polycistronic regulators, tag sequences, such as nucleotide sequence "tags" and "tag" peptide coding sequences, which facilitates identification, separation, purification, or isolation of an expressed polypeptide.

In another embodiment, the expression vector further comprises a tag sequence adjacent to the coding sequence for the secretion signal or to the coding sequence for the recombinant protein or peptide. In one embodiment, this tag sequence allows for purification of the protein. The tag sequence can be an affinity tag, such as a hexa-histidine affinity tag. In another embodiment, the affinity tag can be a glutathione-S-transferase molecule. The tag can also be a fluorescent molecule, such as YFP or GFP, or analogs of such fluorescent proteins. The tag can also be a portion of an antibody molecule, or a known antigen or ligand for a known binding partner useful for purification.

A protein-encoding gene according to the present invention can include, in addition to the protein coding sequence, the following regulatory elements operably linked thereto: a promoter, a ribosome binding site (RBS), a transcription terminator, translational start and stop signals. Useful RBSs can be obtained from any of the species useful as host cells in expression systems according to the present invention, preferably from the selected host cell. Many specific and a variety of consensus RBSs are known, e.g., those described in and referenced by D. Frishman et al., Starts of bacterial genes:

estimating the reliability of computer predictions, Gene 234 (2):257-65 (8 Jul. 1999); and B. E. Suzek et al., A probabilistic method for identifying start codons in bacterial genomes, Bioinformatics 17 (12):1123-30 (December 2001). In addition, either native or synthetic RBSs may be used, e.g., those described in: EP 0207459 (synthetic RBSs); O. Ikehata et al., Primary structure of nitrile hydratase deduced from the nucleotide sequence of a Rhodococcus species and its expression in Escherichia coli, Eur. J. Biochem. 181 (3):563-70 (1989) (native RBS sequence of AAGGAAG). Further examples of methods, vectors, and translation and transcription elements, and other elements useful in the present invention are described in, e.g.: U.S. Pat. No. 5,055,294 to Gilroy and U.S. Pat. No. 5,128,130 to Gilroy et al.; U.S. Pat. No. 5,281,532 to Rammler et al.; U.S. Pat. Nos. 4,695,455 and 4,861,595 to Barnes et al.; U.S. Pat. No. 4,755,465 to Gray et al.; and U.S. Pat. No. 5,169,760 to Wilcox.

Transcription of the DNA encoding the proteins of the present invention by Pseudomonas is increased by inserting an enhancer sequence into the vector or plasmid. Typical enhancers are cis-acting elements of DNA, usually about from 10 to 300 bp in size that act on the promoter to increase its transcription. Examples include various Pseudomonas enhancers.

Generally, the recombinant expression vectors will include origins of replication and selectable markers permitting transformation of the Pseudomonas host cell and a promoter derived from a highly-expressed gene to direct transcription of a downstream structural sequence. Such promoters can be derived from operons encoding the enzymes such as 3-phosphoglycerate kinase (PGK), acid phosphatase, or heat shock proteins, among others. The heterologous structural sequence is assembled in appropriate phase with translation initiation and termination sequences, and preferably, a leader sequence capable of directing secretion of the translated enzyme. Optionally the heterologous sequence can encode a fusion enzyme including an N-terminal identification peptide imparting desired characteristics, e.g., stabilization or simplified purification of expressed recombinant product.

Vectors are known in the art as useful for expressing recombinant proteins in host cells, and any of these may be used for expressing the genes according to the present invention. Such vectors include, e.g., plasmids, cosmids, and phage expression vectors. Examples of useful plasmid vectors include, but are not limited to, the expression plasmids pBBR1MCS, pDSK519, pKT240, pML122, pPS10, RK2, RK6, pRO1600, and RSF1010. Other examples of such useful vectors include those described by, e.g.: N. Hayase, in Appl. Envir. Microbiol. 60 (9):3336-42 (September 1994); A. A. Lushnikov et al., in Basic Life Sci. 30:657-62 (1985); S. Graupner & W. Wackernagel, in Biomolec. Eng. 17 (1):11-16. (October 2000); H. P. Schweizer, in Curr. Opin. Biotech. 12 (5):439-45 (October 2001); M. Bagdasarian & K. N. Timmis, in Curr. Topics Microbiol. Immunol. 96:47-67 (1982); T. Ishii et al., in FEMS Microbiol. Lett. 116 (3):307-13 (Mar. 1, 1994); I. N. Olekhnovich & Y. K. Fomichev, in Gene 140 (1):63-65 (Mar. 11, 1994); M. Tsuda & T. Nakazawa, in Gene 136 (1-2):257-62 (Dec. 22, 1993); C. Nieto et al., in Gene 87 (1):145-49 (Mar. 1, 1990); J. D. Jones & N. Gutterson, in Gene 61 (3):299-306 (1987); M. Bagdasarian et al., in Gene 16 (1-3):237-47 (December 1981); H. P. Schweizer et al., in Genet. Eng. (NY) 23:69-81 (2001); P. Mukhopadhyay et al., in J. Bact. 172 (1):477-80 (January 1990); D. O. Wood et al., in J. Bact. 145 (3):1448-51 (March 1981); and R. Holtwick et al., in Microbiology 147 (Pt 2):337-44 (February 2001).

Further examples of expression vectors that can be useful in Pseudomonas host cells include those listed in Table 2 as derived from the indicated replicons.

TABLE 2

Some Examples of Useful Expression Vectors

| Replicon | Vector(s) |
| --- | --- |
| PPS10 | PCN39, PCN51 |
| RSF1010 | PKT261-3 |
|  | PMMB66EH |
|  | PEB8 |
|  | PPLGN1 |
|  | PMYC1050 |
| RK2/RP1 | PRK415 |
|  | PJB653 |
| PRO1600 | PUCP |
|  | PBSP |

The expression plasmid, RSF1010, is described, e.g., by F. Heffron et al., in Proc. Nat'l Acad. Sci. USA 72 (9):3623-27 (September 1975), and by K. Nagahari & K. Sakaguchi, in J. Bact. 133 (3):1527-29 (March 1978). Plasmid RSF1010 and derivatives thereof are particularly useful vectors in the present invention. Exemplary, useful derivatives of RSF1010, which are known in the art, include, e.g., pKT212, pKT214, pKT231 and related plasmids, and pMYC1050 and related plasmids (see, e.g., U.S. Pat. Nos. 5,527,883 and 5,840,554 to Thompson et al.), such as, e.g., pMYC1803. Plasmid pMYC1803 is derived from the RSF1010-based plasmid pTJS260 (see U.S. Pat. No. 5,169,760 to Wilcox), which carries a regulated tetracycline resistance marker and the replication and mobilization loci from the RSF1010 plasmid. Other exemplary useful vectors include those described in U.S. Pat. No. 4,680,264 to Puhler et al.

In one embodiment, an expression plasmid is used as the expression vector. In another embodiment, RSF1010 or a derivative thereof is used as the expression vector. In still another embodiment, pMYC1050 or a derivative thereof, or pMYC1803 or a derivative thereof, is used as the expression vector.

The plasmid can be maintained in the host cell by use of a selection marker gene, also present in the plasmid. This may be an antibiotic resistance gene(s), in which case the corresponding antibiotic(s) will be added to the fermentation medium, or any other type of selection marker gene known as useful in the art, e.g., a prototrophy-restoring gene in which case the plasmid will be used in a host cell that is auxotrophic for the corresponding trait, e.g., a biocatalytic trait such as an amino acid biosynthesis or a nucleotide biosynthesis trait or a carbon source utilization trait.

The promoters used in accordance with the present invention may be constitutive promoters or regulated promoters. Common examples of useful regulated promoters include those of the family derived from the lac promoter (i.e. the lacZ promoter), especially the tac and trc promoters described in U.S. Pat. No. 4,551,433 to DeBoer, as well as Ptac16, Ptac17, PtacII, PlacUV5, and the T7lac promoter. In one embodiment, the promoter is not derived from the host cell organism. In certain embodiments, the promoter is derived from an E. coli organism.

Common examples of non-lac-type promoters useful in expression systems according to the present invention include, e.g., those listed in Table 3.

TABLE 3

Examples of non-lac Promoters

| Promoter | Inducer |
| --- | --- |
| $P_R$ | High temperature |
| $P_L$ | High temperature |
| Pm | Alkyl- or halo-benzoates |
| Pu | Alkyl- or halo-toluenes |
| Psal | Salicylates |

See, e.g.: J. Sanchez-Romero & V. De Lorenzo (1999) Genetic Engineering of Nonpathogenic *Pseudomonas* strains as Biocatalysts for Industrial and Environmental Processes, in Manual of Industrial Microbiology and Biotechnology (A. Demain & J. Davies, eds.) pp. 460-74 (ASM Press, Washington, D.C.); H. Schweizer (2001) Vectors to express foreign genes and techniques to monitor gene expression for Pseudomonads, Current Opinion in Biotechnology, 12:439-445; and R. Slater & R. Williams (2000) The Expression of Foreign DNA in Bacteria, in Molecular Biology and Biotechnology (J. Walker & R. Rapley, eds.) pp. 125-54 (The Royal Society of Chemistry, Cambridge, UK)). A promoter having the nucleotide sequence of a promoter native to the selected bacterial host cell may also be used to control expression of the transgene encoding the target polypeptide, e.g, a *Pseudomonas* anthranilate or benzoate operon promoter (Pant, Pben). Tandem promoters may also be used in which more than one promoter is covalently attached to another, whether the same or different in sequence, e.g., a Pant-Pben tandem promoter (interpromoter hybrid) or a Plac-Plac tandem promoter.

Regulated promoters utilize promoter regulatory proteins in order to control transcription of the gene of which the promoter is a part. Where a regulated promoter is used herein, a corresponding promoter regulatory protein will also be part of an expression system according to the present invention. Examples of promoter regulatory proteins include: activator proteins, e.g., *E. coli* catabolite activator protein, MalT protein; AraC family transcriptional activators; repressor proteins, e.g., *E. coli* LacI proteins; and dual-function regulatory proteins, e.g., *E. coli* NagC protein. Many regulated-promoter/promoter-regulatory-protein pairs are known in the art.

Promoter regulatory proteins interact with an effector compound, i.e. a compound that reversibly or irreversibly associates with the regulatory protein so as to enable the protein to either release or bind to at least one DNA transcription regulatory region of the gene that is under the control of the promoter, thereby permitting or blocking the action of a transcriptase enzyme in initiating transcription of the gene. Effector compounds are classified as either inducers or co-repressors, and these compounds include native effector compounds and gratuitous inducer compounds. Many regulated-promoter/promoter-regulatory-protein/effector-compound trios are known in the art. Although an effector compound can be used throughout the cell culture or fermentation, in a preferred embodiment in which a regulated promoter is used, after growth of a desired quantity or density of host cell biomass, an appropriate effector compound is added to the culture in order directly or indirectly result in expression of the desired target gene(s).

By way of example, where a lac family promoter is utilized, a lacI gene can also be present in the system. The lacI gene, which is (normally) a constitutively expressed gene, encodes the Lac repressor protein (LacI protein) which binds to the lac operator of these promoters. Thus, where a lac family promoter is utilized, the lacI gene can also be included and expressed in the expression system. In the case of the lac promoter family members, e.g., the tac promoter, the effector compound is an inducer, preferably a gratuitous inducer such as IPTG (isopropyl-D-1-thiogalactopyranoside, also called "isopropylthiogalactoside").

The Champion™ pET expression system provides a high level of protein production. Expression is induced from the strong T7lac promoter. This system takes advantage of the high activity and specificity of the bacteriophage T7 RNA polymerase for high level transcription of the gene of interest. The lac operator located in the promoter region provides tighter regulation than traditional T7-based vectors, improving plasmid stability and cell viability (Studier, F. W. and B. A. Moffatt (1986) *J Molecular Biology* 189 (1): 113-30; Rosenberg, et al. (1987) *Gene* 56 (1): 125-35). The T7 expression system uses the T7 promoter and T7 RNA polymerase (T7 RNAP) for high-level transcription of the gene of interest. High-level expression is achieved in T7 expression systems because the T7 RNAP is more processive than native *E. coli* RNAP and is dedicated to the transcription of the gene of interest. Expression of the identified gene is induced by providing a source of T7 RNAP in the host cell. This is accomplished by using a BL21 *E. coli* host containing a chromosomal copy of the T7 RNAP gene. The T7 RNAP gene is under the control of the lacUV5 promoter which can be induced by IPTG. T7 RNAP is expressed upon induction and transcribes the gene of interest.

The pBAD expression system allows tightly controlled, titratable expression of recombinant protein through the presence of specific carbon sources such as glucose, glycerol and arabinose (Guzman, et al. (1995) *J Bacteriology* 177 (14): 4121-30). The pBAD vectors are uniquely designed to give precise control over expression levels. Heterologous gene expression from the pBAD vectors is initiated at the araBAD promoter. The promoter is both positively and negatively regulated by the product of the araC gene. AraC is a transcriptional regulator that forms a complex with L-arabinose. In the absence of L-arabinose, the AraC dimer blocks transcription. For maximum transcriptional activation two events are required: (i.) L-arabinose binds to AraC allowing transcription to begin. (ii.) The cAMP activator protein (CAP)-cAMP complex binds to the DNA and stimulates binding of AraC to the correct location of the promoter region.

The trc expression system allows high-level, regulated expression in *E. coli* from the trc promoter. The trc expression vectors have been optimized for expression of eukaryotic genes in *E. coli*. The trc promoter is a strong hybrid promoter derived from the tryptophane (trp) and lactose (lac) promoters. It is regulated by the lacO operator and the product of the lacIQ gene (Brosius, J. (1984) *Gene* 27 (2): 161-72).

Expression Systems

In one embodiment, an improved expression system for the production of recombinant protein is provided. In one embodiment, the system includes a host cell and a vector comprising a recombinant protein or peptide operably linked to a *Pseudomonas fluorescens* Sec-system secretion signal selected from the group consisting of a pbp secretion signal, an OprE secretion signal, a Lys-Arg-Orn binding protein secretion signal, an azurin secretion signal, an iron (III) binding protein secretion signal and a lipoprotein B secretion signal or a sequence that is substantially homologous to the signal sequence.

In a separate embodiment, an expression system is provided that includes a *P. fluorescens* host cell and at least one vector that includes a Sec secretion signal from any genome operably linked to a protein or peptide of interest. The vector can have any of the characteristics described above. In one embodiment, the Sec secretion signal is derived from a *P. fluorescens* genome. However, in another embodiment, the Sec-secretion signal is derived from any bacterial genome. In one embodiment, the secretion signal is derived from a bacterial genome that is not a *P. fluorescens* genome, and in a specific embodiment, the secretion signal is derived from an *E. coli* genome. The secretion signal may, in certain embodiments, be native to the protein. In a separate embodiment, the secretion signal is not native to the protein.

For example, the secretion system provided may include a Sec secretion signal such as the secretion signal for a skp protein. In embodiments in which the protein that is being expressed recombinantly is targeted either to a periplasmic compartment or extracellularly, the native leader sequence of that protein can be included in the vector, operably linked to the protein of interest.

In other embodiments, a secretion signal sequence derived from a different protein can be included in the vector. Surprisingly, *P. fluorescens* can properly target proteins with a variety of signal sequences to the periplasm through its Sec secretion pathway. In some embodiments, no further modifications are provided between the signal sequence and the protein or peptide of interest. However, in certain embodiments, additional cleavage signals are incorporated to promote proper processing of the amino terminal of the peptide.

The secretion system can also include a fermentation media, such as described below. In one embodiment, the system includes a mineral salts media. In another embodiment, the system includes a chemical inducer in the media.

The system can also include a promoter, which can be a selectable promoter, and an inducer. In some cases, this promoter is a promoter not native to *P. fluorescens*, such as an *E. coli* promoter. In certain embodiments, this promoter is, for example, an inducible promoter such as a lac promoter. The promoter can also be a hybrid of several different promoters, at least one of which is not native to a *P. fluorescens* organism. For example, the promoter can be a trc promoter. The promoter can also, for example, be a tac promoter.

Process

In one embodiment, an improved process for the production of recombinant protein is provided which includes a *P. fluorescens* host cell expressing a fusion protein of interest linked to a Sec secretion signal. The process can include providing a *P. fluorescens* cell comprising a vector encoding a recombinant protein or peptide operably linked to a recombinant Sec system secretion signal sequence, and growing the cell under conditions that produce expression of the protein or peptide. The vector can have any of the characteristics described above. In one embodiment, the Sec secretion signal is derived from a *P. fluorescens* genome. In another embodiment, the Sec-secretion signal is derived from any bacterial genome. In one embodiment, the secretion signal is derived from a bacterial genome and in a specific embodiment, the secretion signal is derived from an *E. coli* genome. The secretion signal may, in certain embodiments, be native to the protein. In a separate embodiment, the secretion signal is not native to the protein.

In a separate embodiment, an improved process for preparing a recombinant protein in any host cell is provided including expression of a *P. fluorescens* Sec-system secretion peptide selected from a pbp, OprE, Lys-Arg-Orn binding protein, azurin, iron (III) binding protein or a lipoprotein B secretion signal, operably linked to a recombinant protein or peptide of interest in a host cell.

In one embodiment, the host cell has a periplasm and expression of the Sec-system peptide targets the recombinant protein to the periplasm of the cell. In a subembodiment, the expression leads to production of extracellular protein. The process may also include the step of purifying the recombinant protein from the periplasm or from extracellular media. The Sec-signal can be expressed linked to the protein and the signal-linked protein can be purified from the cell. Therefore, in one embodiment, this isolated peptide is a fusion protein of the secretion signal and a protein or peptide of interest. However, the secretion signal can also be cleaved from the protein when the protein is targeted to the periplasm. In one embodiment, the linkage between the Sec-system secretion signal and the protein or peptide is modified to increase cleavage of the secretion signal.

In one embodiment, the process can produce protein localized to the periplasm of the host cell. In one embodiment, the process produces properly processed recombinant protein in the cell. In another embodiment, the expression of the Sec-system peptide may produce active recombinant protein in the cell. The process of the invention may also lead to increased yield of recombinant protein as compared to when the protein is expressed without the Sec-secretion signal.

In one embodiment, the process produces at least 0.1 g/L protein in the periplasmic compartment. In another embodiment, the process produces 0.1 to 10 g/L periplasmic protein in the cell. In subembodiments, the process produces at least about 0.2, 0.3, 0.4, 0.5, 0.6, 0.7, 0.8, 0.9 or 1.0 g/L periplasmic protein. In one embodiment, the total recombinant protein produced is at least 1.0 g/L. In some embodiments, the amount of periplasmic protein produced is at least about 5%, about 10%, about 15%, about 20%, about 25%, about 30%, about 40%, about 50%, about 60%, about 70%, about 80%, about 90%, about 95% or more of total recombinant protein produced.

In one embodiment, the process produces at least 0.1 g/L correctly processed protein. A correctly processed protein has an amino terminus of the native protein. In another embodiment, the process produces 0.1 to 10 g/L correctly processed protein in the cell. In subembodiments, the process produces at least about 0.2, 0.3, 0.4, 0.5, 0.6, 0.7, 0.8, 0.9 or 1.0 g/L correctly processed protein. In one embodiment, the total correctly processed recombinant protein produced is at least 1.0 g/L. In subembodiments, the total correctly processed protein produced can be at least about 2.0, 3.0, 4.0, 5.0, 6.0, 7.0, 8.0, 9.0, 10.0, 15.0, 20.0 or 50.0 g/L. In some embodiments, the amount of correctly processed protein produced is at least about 5%, about 10%, about 15%, about 20%, about 25%, about 30%, about 40%, about 50%, about 60%, about 70%, about 80%, about 90%, about 95% or more of total recombinant protein in a correctly processed form.

In some embodiments, the protein can also be produced in an active form. The term "active" means the presence of biological function or biological effect, wherein the biological function or effect is comparative or substantially corresponds to the biological function or effect of a corresponding native protein or peptide. In the context of proteins this typically means that a polynucleotide or polypeptide comprises a biological function or effect that has at least about 20%, about 50%, preferably at least about 60-80%, and most preferably at least about 90-95% activity compared to the corresponding native protein or peptide using standard parameters. The determination of protein or peptide activity can be performed utilizing corresponding standard, targeted comparative biological assays for particular proteins or peptides. One indication that a recombinant protein or peptide biological function or effect is that the recombinant polypeptide is immunologically cross reactive with the native polypeptide.

In another embodiment, more than 50% of the expressed, transgenic peptide, polypeptide, protein, or fragment thereof produced can be produced in a renaturable form in host cell. In another embodiment about 60%, 70%, 75%, 80%, 85%, 90%, 95% of the expressed protein is obtained in or can be renatured into active form.

The process of the invention can also lead to increased yield of recombinant protein. In one embodiment, the process produces recombinant protein as 5, 10, 15, 20, 25, 30, 40 or 50, 55, 60, 65, 70, or 75% of total cell protein (tcp). "Percent total cell protein" is the amount of protein or peptide in the host cell as a percentage of aggregate cellular protein. The determination of the percent total cell protein is well known in the art.

In a particular embodiment, the host cell can have a recombinant peptide, polypeptide, protein, or fragment thereof expression level of at least 1% tcp and a cell density of at least 40 g/L, when grown (i.e. within a temperature range of about 4° C. to about 55° C., inclusive) in a mineral salts medium. In a particularly preferred embodiment, the expression system will have a recombinant protein of peptide expression level of at least 5% tcp and a cell density of at least 40 g/L, when grown (i.e. within a temperature range of about 4° C. to about 55° C., inclusive) in a mineral salts medium at a fermentation scale of at least 10 Liters.

Host Cell

In one embodiment the invention provides a *P. fluorescens* expression system for expression of recombinant protein comprising a Sec-type secretion signal. This aspect of the invention is founded on the surprising discovery that the *P. fluorescens* Sec secretion system is capable of properly processing and targeting secretion signals from both *P. fluorescens* and non-*P. fluorescens* Sec signal systems.

In this embodiment, the host cell can be selected from "Gram-negative Proteobacteria Subgroup 18." "Gram-negative Proteobacteria Subgroup 18" is defined as the group of all subspecies, varieties, strains, and other sub-special units of the species *Pseudomonas fluorescens*, including those belonging, e.g., to the following (with the ATCC or other deposit numbers of exemplary strain(s) shown in parenthesis): *Pseudomonas fluorescens* biotype A, also called biovar 1 or biovar I (ATCC 13525); *Pseudomonas fluorescens* biotype B, also called biovar 2 or biovar II (ATCC 17816); *Pseudomonas fluorescens* biotype C, also called biovar 3 or biovar III (ATCC 17400); *Pseudomonas fluorescens* biotype F, also called biovar 4 or biovar IV (ATCC 12983); *Pseudomonas fluorescens* biotype G, also called biovar 5 or biovar V (ATCC 17518); *Pseudomonas fluorescens* biovar VI; *Pseudomonas fluorescens* Pf0-1; *Pseudomonas fluorescens* Pf-5 (ATCC BAA-477); *Pseudomonas fluorescens* SBW25; and *Pseudomonas fluorescens* subsp. *cellulosa* (NCIMB 10462).

The host cell can be selected from "Gram-negative Proteobacteria Subgroup 19." "Gram-negative Proteobacteria Subgroup 19" is defined as the group of all strains of *Pseudomonas fluorescens* biotype A. A particularly preferred strain of this biotype is *P. fluorescens* strain MB101 (see U.S. Pat. No. 5,169,760 to Wilcox), and derivatives thereof. An example of a preferred derivative thereof is *P. fluorescens* strain MB214, constructed by inserting into the MB101 chromosomal asd (aspartate dehydrogenase gene) locus, a native *E. coli* PlacI-lacI-lacZYA construct (i.e. in which PlacZ was deleted).

Additional *P. fluorescens* strains that can be used in the present invention include *Pseudomonas fluorescens* Migula and *Pseudomonas fluorescens* Loitokitok, having the following ATCC designations: [NCIB 8286]; NRRL B-1244; NCIB 8865 strain CO1; NCIB 8866 strain CO2; 1291 [ATCC 17458; IFO 15837; NCIB 8917; LA; NRRL B-1864; pyrrolidine; PW2 [ICMP 3966; NCPPB 967; NRRL B-899]; 13475; NCTC 10038; NRRL B-1603 [6; IFO 15840]; 52-1C; CCEB 488-A [BU 140]; CCEB 553 [IEM 15/47]; IAM 1008 [AHH-27]; IAM 1055 [AHH-23]; 1 [IFO 15842]; 12 [ATCC 25323; NIH 11; den Dooren de Jong 216]; 18 [IFO 15833; WRRL P-7]; 93 [TR-10]; 108 [52-22; IFO 15832]; 143 [IFO 15836; PL]; 149 [2-40-40; IFO 15838]; 182 [IFO 3081; PJ 73]; 184 [IFO 15830]; 185 [W2 L-1]; 186 [IFO 15829; PJ 79]; 187 [NCPPB 263]; 188 [NCPPB 316]; 189 [PJ227; 1208]; 191 [IFO 15834; PJ 236; 22/1]; 194 [Klinge R-60; PJ 253]; 196 [PJ 288]; 197 [PJ 290]; 198 [PJ 302]; 201 [PJ 368]; 202 [PJ 372]; 203 [PJ 376]; 204 [IFO 15835; PJ 682]; 205 [PJ 686]; 206 [PJ 692]; 207 [PJ 693]; 208 [PJ 722]; 212 [PJ 832]; 215 [PJ 849]; 216 [PJ 885]; 267 [B-9]; 271 [B-1612]; 401 [C71A; IFO 15831; PJ 187]; NRRL B-3178 [4; IFO 15841]; KY 8521; 3081; 30-21; [IFO 3081]; N; PYR; PW; D946-B83 [BU 2183; FERM-P 3328]; P-2563 [FERM-P 2894; IFO 13658]; IAM-1126 [43F]; M-1; A506 [A5-06]; A505 [A5-05-1]; A526 [A5-26]; B69; 72; NRRL B-4290; PMW6 [NCIB 11615]; SC 12936; Al [IFO 15839]; F 1847 [CDC-EB]; F 1848 [CDC 93]; NCIB 10586; P17; F-12; AmMS 257; PRA25; 6133D02; 6519E01; N1; SC15208; BNL-WVC; NCTC 2583 [NCIB 8194]; H13; 1013 [ATCC 11251; CCEB 295]; IFO 3903; 1062; or Pf-5.

In another embodiment, the process provides the expression of fusion proteins with a *P. fluorescens* Sec-system secretion peptide selected from a phosphate binding protein (pbp) secretion signal, an Outer Membrane Porin E (OprE) secretion signal, a Lys-Arg-Orn binding protein secretion signal, an azurin secretion signal, an iron (III) binding protein secretion signal and a lipoprotein B secretion signal. This process is founded on the idea that the capacity of the *P. fluorescens* Sec secretion signals to process secreted proteins indicates that the cells are ideally suited to produce secreted proteins. Therefore, the signaling systems derived from these cells could be ideal signaling systems for this type of secretion in multiple expression systems. Therefore, the process of expressing proteins or peptides using the identified *P. fluorescens* Sec system secretion signals can be used in any given host system, including of either eukaryotic or prokaryotic origin.

In this embodiment, the host cell can be any cell capable of producing recombinant protein or peptide, including a *P. fluorescens* cell as described above. The most commonly used systems to produce recombinant proteins or peptides include certain bacterial cells, particularly *E. coli*, because of their relatively inexpensive growth requirements and potential capacity to produce protein in large batch cultures. Yeast are also used to express biologically relevant proteins and peptides, particularly for research purposes. Systems include *Saccharomyces cerevisiae* or *Pichia pastoris*. These systems are well characterized, provide generally acceptable levels of total protein expression and are comparatively fast and inexpensive. Insect cell expression systems have also emerged as an alternative for expressing recombinant proteins in biologically active form. In some cases, correctly folded proteins that are post-translationally modified can be produced. Mammalian cell expression systems, such as Chinese hamster ovary cells, have also been used for the expression of recombinant proteins. On a small scale, these expression systems are often effective. Certain biologics can be derived from proteins, particularly in animal or human health applications. In another embodiment, the host cell is a plant cell, including, but not limited to, a tobacco cell, corn, a cell from an *Arabidopsis* species, potato or rice cell. In another embodiment, a multicellular organism is analyzed or is modified in the process, including but not limited to a transgenic organism. Techniques for analyzing and/or modifying a multicellular organism are generally based on techniques described for modifying cells described below.

In one embodiment, the host cell can be a prokaryote such as a bacterial cell including, but not limited to an *Escherichia* or a *Pseudomonas* species. Typical bacterial cells are described, for example, in "Biological Diversity: Bacteria and Archaeans", a chapter of the On-Line Biology Book, provided by Dr M J Farabee of the Estrella Mountain Community College, Arizona, USA on the internet at www.emc-.maricotpa.edu/faculty/farabee/BIOBK/BioBookDiversity.sub.—-2.html. In certain embodiments, the host cell can be a Pseudomonad cell, and can typically be a *P. fluorescens* cell. In other embodiments, the host cell can also be an *E. coli* cell. In another embodiment the host cell can be a eukaryotic cell, for example an insect cell, including but not limited to a cell from a *Spodoptera, Trichoplusia Drosophila* or an *Estigmene* species, or a mammalian cell, including but not limited to a murine cell, a hamster cell, a monkey, a primate or a human cell.

In one embodiment, the host cell can be a member of any of the bacterial taxa. The cell can, for example, be a member of any species of eubacteria. The host can be a member any one of the taxa: Acidobacteria, Actinobacteira, Aquificae, Bacteroidetes, Chlorobi, Chlamydiae, Choroflexi, Chrysiogenetes, Cyanobacteria, Deferribacteres, Deinococcus, Dictyoglomi, Fibrobacteres, Firmicutes, Fusobacteria, Gemmatimonadetes, Lentisphaerae, Nitrospirae, Planctomycetes, Proteobacteria, Spirochaetes, Thermodesulfobacteria, Thermomicrobia, Thermotogae, Thermus (Thermales), or Verrucomicrobia. In a embodiment of a eubacterial host cell, the cell can be a member of any species of eubacteria, excluding Cyanobacteria.

The bacterial host can also be a member of any species of Proteobacteria. A proteobacterial host cell can be a member of any one of the taxa Alphaproteobacteria, Betaproteobacteria, Gammaproteobacteria, Deltaproteobacteria, or Epsilonproteobacteria. In addition, the host can be a member of any one of the taxa Alphaproteobacteria, Betaproteobacteria, or Gammaproteobacteria, and a member of any species of Gammaproteobacteria.

In one embodiment of a Gamma Proteobacterial host, the host will be member of any one of the taxa Aeromonadales, Alteromonadales, Enterobacteriales, Pseudomonadales, or Xanthomonadales; or a member of any species of the Enterobacteriales or Pseudomonadales. In one embodiment, the host cell can be of the order Enterobacteriales, the host cell will be a member of the family Enterobacteriaceae, or a member of any one of the genera *Erwinia, Escherichia*, or *Serratia*; or a member of the genus *Escherichia*. In one embodiment of a host cell of the order Pseudomonadales, the host cell will be a member of the family Pseudomonadaceae, even of the genus *Pseudomonas*. Gamma Proteobacterial hosts include members of the species *Escherichia coli* and members of the species *Pseudomonas fluorescens*.

Other *Pseudomonas* organisms may also be useful. Pseudomonads and closely related species include Gram-negative Proteobacteria Subgroup 1, which include the group of Proteobacteria belonging to the families and/or genera described as "Gram-Negative Aerobic Rods and Cocci" by R. E. Buchanan and N. E. Gibbons (eds.), Bergey's Manual of Determinative Bacteriology, pp. 217-289 (8th ed., 1974) (The Williams & Wilkins Co., Baltimore, Md., USA) (hereinafter "Bergey (1974)"). Table 4 presents these families and genera of organisms.

TABLE 4

Families and Genera Listed in the Part, "Gram-Negative Aerobic Rods and Cocci" (in Bergey (1974))

| | |
|---|---|
| Family I. *Pseudomonadaceae* | *Gluconobacter* |
| | *Pseudomonas* |
| | *Xanthomonas* |
| | *Zoogloea* |
| Family II. *Azotobacteraceae* | *Azomonas* |
| | *Azotobacter* |
| | *Beijerinckia* |
| | *Derxia* |
| Family III. *Rhizobiaceae* | *Agrobacterium* |
| | *Rhizobium* |
| Family IV. *Methylomonadaceae* | *Methylococcus* |
| | *Methylomonas* |
| Family V. *Halobacteriaceae* | *Halobacterium* |
| | *Halococcus* |
| Other Genera | *Acetobacter* |
| | *Alcaligenes* |
| | *Bordetella* |
| | *Brucella* |
| | *Francisella* |
| | *Thermus* |

"Gram-negative Proteobacteria Subgroup 1" also includes Proteobacteria that would be classified in this heading according to the criteria used in the classification. The heading also includes groups that were previously classified in this section but are no longer, such as the genera *Acidovorax, Brevundimonas, Burkholderia, Hydrogenophaga, Oceanimonas, Ralstonia*, and *Stenotrophomonas*, the genus *Sphingomonas* (and the genus *Blastomonas*, derived therefrom), which was created by regrouping organisms belonging to (and previously called species of) the genus *Xanthomonas*, the genus *Acidomonas*, which was created by regrouping organisms belonging to the genus *Acetobacter* as defined in Bergey (1974). In addition hosts can include cells from the genus *Pseudomonas, Pseudomonas enalia* (ATCC 14393), *Pseudomonas nigrifaciens* (ATCC 19375), and *Pseudomonas putrefaciens* (ATCC 8071), which have been reclassified respectively as *Alteromonas haloplanktis, Alteromonas nigrifaciens*, and *Alteromonas putrefaciens*. Similarly, e.g., *Pseudomonas acidovorans* (ATCC 15668) and *Pseudomonas testosteroni* (ATCC 11996) have since been reclassified as *Comamonas acidovorans* and *Comamonas testosteroni*, respectively; and *Pseudomonas nigrifaciens* (ATCC 19375) and *Pseudomonas piscicida* (ATCC 15057) have been reclassified respectively as *Pseudoalteromonas nigrifaciens* and *Pseudoalteromonas piscicida*. "Gram-negative Proteobacteria Subgroup 1" also includes Proteobacteria classified as belonging to any of the families: Pseudomonadaceae, Azotobacteraceae (now often called by the synonym, the "*Azotobacter* group" of Pseudomonadaceae), Rhizobiaceae, and Methylomonadaceae (now often called by the synonym, "Methylococcaceae"). Consequently, in addition to those genera otherwise described herein, further Proteobacterial genera falling within "Gram-negative Proteobacteria Subgroup 1" include: 1) *Azotobacter* group bacteria of the genus *Azorhizophilus*; 2) Pseudomonadaceae family bacteria of the genera *Cellvibrio, Oligella*, and *Teredinibacter*; 3) Rhizobiaceae family bacteria of the genera *Chelatobacter, Ensifer, Liberibacter* (also called "*Candidatus Liberibacter*"), and *Sinorhizobium*; and 4) Methylococcaceae family bacteria of the genera *Methylobacter, Methylocaldum, Methylomicrobium, Methylosarcina*, and *Methylosphaera*.

In another embodiment, the host cell is selected from "Gram-negative Proteobacteria Subgroup 2." "Gram-negative Proteobacteria Subgroup 2" is defined as the group of Proteobacteria of the following genera (with the total numbers of catalog-listed, publicly-available, deposited strains thereof indicated in parenthesis, all deposited at ATCC, except as otherwise indicated): *Acidomonas* (2); *Acetobacter* (93); *Gluconobacter* (37); *Brevundimonas* (23); *Beijerinckia* (13); *Derxia* (2); *Brucella* (4); *Agrobacterium* (79); *Chelatobacter* (2); *Ensifer* (3); *Rhizobium* (144); *Sinorhizobium* (24); *Blastomonas* (1); *Sphingomonas* (27); *Alcaligenes* (88); *Bordetella* (43); *Burkholderia* (73); *Ralstonia* (33); *Acidovorax* (20); *Hydrogenophaga* (9); *Zoogloea* (9); *Methylobacter* (2); *Methylocaldum* (1 at NCIMB); *Methylococcus* (2); *Methylomicrobium* (2); *Methylomonas* (9); *Methylosarcina* (1); *Methylosphaera*; *Azomonas* (9); *Azorhizophilus* (5); *Azotobacter* (64); *Cellvibrio* (3); *Oligella* (5); *Pseudomonas* (1139); *Francisella* (4); *Xanthomonas* (229); *Stenotrophomonas* (50); and *Oceanimonas* (4).

Exemplary host cell species of "Gram-negative Proteobacteria Subgroup 2" include, but are not limited to the following bacteria (with the ATCC or other deposit numbers of exemplary strain(s) thereof shown in parenthesis): *Acidomonas methanolica* (ATCC 43581); *Acetobacter aceti* (ATCC 15973); *Gluconobacter oxydans* (ATCC 19357); *Brevundimonas diminuta* (ATCC 11568); *Beijerinckia indica* (ATCC 9039 and ATCC 19361); *Derxia gummosa* (ATCC 15994); *Brucella melitensis* (ATCC 23456), *Brucella abortus* (ATCC 23448); *Agrobacterium tumefaciens* (ATCC 23308), *Agrobacterium radiobacter* (ATCC 19358), *Agrobacterium rhizogenes* (ATCC 11325); *Chelatobacter heintzii* (ATCC 29600); *Ensifer adhaerens* (ATCC 33212); *Rhizobium leguminosarum* (ATCC 10004); *Sinorhizobium fredii* (ATCC 35423); *Blastomonas natatoria* (ATCC 35951); *Sphingomonas paucimobilis* (ATCC 29837); *Alcaligenes faecalis* (ATCC 8750); *Bordetella pertussis* (ATCC 9797); *Burkholderia cepacia* (ATCC 25416); *Ralstonia pickettii* (ATCC 27511); *Acidovorax facilis* (ATCC 11228); *Hydrogenophaga flava* (ATCC 33667); *Zoogloea ramigera* (ATCC 19544); *Methylobacter luteus* (ATCC 49878); *Methylocaldum gracile* (NCIMB 11912); *Methylococcus capsulatus* (ATCC 19069); *Methylomicrobium agile* (ATCC 35068); *Methylomonas methanica* (ATCC 35067); *Methylosarcina fibrata* (ATCC 700909); *Methylosphaera hansonii* (ACAM 549); *Azomonas agilis* (ATCC 7494); *Azorhizophilus paspali* (ATCC 23833); *Azotobacter chroococcum* (ATCC 9043); *Cellvibrio mixtus* (UQM 2601); *Oligella urethralis* (ATCC 17960); *Pseudomonas aeruginosa* (ATCC 10145), *Pseudomonas fluorescens* (ATCC 35858); *Francisella tularensis* (ATCC 6223); *Stenotrophomonas maltophilia* (ATCC 13637); *Xanthomonas campestris* (ATCC 33913); and *Oceanimonas doudoroffii* (ATCC 27123).

In another embodiment, the host cell is selected from "Gram-negative Proteobacteria Subgroup 3." "Gram-negative Proteobacteria Subgroup 3" is defined as the group of Proteobacteria of the following genera: *Brevundimonas; Agrobacterium; Rhizobium; Sinorhizobium; Blastomonas; Sphingomonas; Alcaligenes; Burkholderia; Ralstonia; Acidovorax; Hydrogenophaga; Methylobacter; Methylocaldum; Methylococcus; Methylomicrobium; Methylomonas; Methylosarcina; Methylosphaera; Azomonas; Azorhizophilus; Azotobacter; Cellvibrio; Oligella; Pseudomonas; Teredinibacter; Francisella; Stenotrophomonas; Xanthomonas*; and *Oceanimonas*.

In another embodiment, the host cell is selected from "Gram-negative Proteobacteria Subgroup 4." "Gram-negative Proteobacteria Subgroup 4" is defined as the group of Proteobacteria of the following genera: *Brevundimonas; Blastomonas; Sphingomonas; Burkholderia; Ralstonia; Acidovorax; Hydrogenophaga; Methylobacter; Methylocaldum; Methylococcus; Methylomicrobium; Methylomonas; Methylosarcina; Methylosphaera; Azomonas; Azorhizophilus; Azotobacter; Cellvibrio; Oligella; Pseudomonas; Teredinibacter; Francisella; Stenotrophomonas; Xanthomonas*; and *Oceanimonas*.

In an embodiment, the host cell is selected from "Gram-negative Proteobacteria Subgroup 5." "Gram-negative Proteobacteria Subgroup 5" is defined as the group of Proteobacteria of the following genera: *Methylobacter; Methylocaldum; Methylococcus; Methylomicrobium; Methylomonas; Methylosarcina; Methylosphaera; Azomonas; Azorhizophilus; Azotobacter; Cellvibrio; Oligella; Pseudomonas; Teredinibacter; Francisella; Stenotrophomonas; Xanthomonas*; and *Oceanimonas*.

The host cell can be selected from "Gram-negative Proteobacteria Subgroup 6." "Gram-negative Proteobacteria Subgroup 6" is defined as the group of Proteobacteria of the following genera: *Brevundimonas; Blastomonas; Sphingomonas; Burkholderia; Ralstonia; Acidovorax; Hydrogenophaga; Azomonas; Azorhizophilus; Azotobacter; Cellvibrio; Oligella; Pseudomonas; Teredinibacter; Stenotrophomonas; Xanthomonas*; and *Oceanimonas*.

The host cell can be selected from "Gram-negative Proteobacteria Subgroup 7." "Gram-negative Proteobacteria Subgroup 7" is defined as the group of Proteobacteria of the following genera: *Azomonas; Azorhizophilus; Azotobacter; Cellvibrio; Oligella; Pseudomonas; Teredinibacter; Stenotrophomonas; Xanthomonas*; and *Oceanimonas*.

The host cell can be selected from "Gram-negative Proteobacteria Subgroup 8." "Gram-negative Proteobacteria Subgroup 8" is defined as the group of Proteobacteria of the following genera: *Brevundimonas; Blastomonas; Sphingomonas; Burkholderia; Ralstonia; Acidovorax; Hydrogenophaga; Pseudomonas; Stenotrophomonas; Xanthomonas*; and *Oceanimonas*.

The host cell can be selected from "Gram-negative Proteobacteria Subgroup 9." "Gram-negative Proteobacteria Subgroup 9" is defined as the group of Proteobacteria of the following genera: *Brevundimonas; Burkholderia; Ralstonia; Acidovorax; Hydrogenophaga; Pseudomonas; Stenotrophomonas*; and *Oceanimonas*.

The host cell can be selected from "Gram-negative Proteobacteria Subgroup 10." "Gram-negative Proteobacteria Subgroup 10" is defined as the group of Proteobacteria of the following genera: *Burkholderia; Ralstonia; Pseudomonas; Stenotrophomonas*; and *Xanthomonas*.

The host cell can be selected from "Gram-negative Proteobacteria Subgroup 11." "Gram-negative Proteobacteria Subgroup 11" is defined as the group of Proteobacteria of the genera: *Pseudomonas; Stenotrophomonas*; and *Xanthomonas*. The host cell can be selected from "Gram-negative Proteobacteria Subgroup 12." "Gram-negative Proteobacteria Subgroup 12" is defined as the group of Proteobacteria of the following genera: *Burkholderia; Ralstonia; Pseudomonas*. The host cell can be selected from "Gram-negative Proteobacteria Subgroup 13." "Gram-negative Proteobacteria Subgroup 13" is defined as the group of Proteobacteria of the following genera: *Burkholderia; Ralstonia; Pseudomonas*; and *Xanthomonas*. The host cell can be selected from "Gram-negative Proteobacteria Subgroup 14." "Gram-negative Proteobacteria Subgroup 14" is defined as the group of Proteobacteria of the following genera: *Pseudomonas* and *Xanthomonas*. The host cell can be selected from "Gram-negative Proteobacteria Subgroup 15." "Gram-negative Proteobacteria Subgroup 15" is defined as the group of Proteobacteria of the genus *Pseudomonas*.

The host cell can be selected from "Gram-negative Proteobacteria Subgroup 16." "Gram-negative Proteobacteria Subgroup 16" is defined as the group of Proteobacteria of the following *Pseudomonas* species (with the ATCC or other deposit numbers of exemplary strain(s) shown in parenthesis): *Pseudomonas abietaniphila* (ATCC 700689); *Pseudomonas aeruginosa* (ATCC 10145); *Pseudomonas alcaligenes* (ATCC 14909); *Pseudomonas anguilliseptica* (ATCC 33660); *Pseudomonas citronellolis* (ATCC 13674); *Pseudomonas flavescens* (ATCC 51555); *Pseudomonas mendocina* (ATCC 25411); *Pseudomonas nitroreducens* (ATCC 33634); *Pseudomonas oleovorans* (ATCC 8062); *Pseudomonas pseudoalcaligenes* (ATCC 17440); *Pseudomonas resinovorans* (ATCC 14235); *Pseudomonas straminea* (ATCC 33636); *Pseudomonas agarici* (ATCC 25941); *Pseudomonas alcaliphila; Pseudomonas alginovora; Pseudomonas andersonii; Pseudomonas asplenii* (ATCC 23835); *Pseudomonas azelaica* (ATCC 27162); *Pseudomonas beijerinckii* (ATCC 19372); *Pseudomonas borealis; Pseudomonas boreopolis* (ATCC 33662); *Pseudomonas brassicacearum; Pseudomonas butanovora* (ATCC 43655); *Pseudomonas cellulosa* (ATCC 55703); *Pseudomonas aurantiaca* (ATCC 33663); *Pseudomonas chlororaphis* (ATCC 9446, ATCC 13985, ATCC 17418, ATCC 17461); *Pseudomonas fragi* (ATCC 4973); *Pseudomonas lundensis* (ATCC 49968); *Pseudomonas taetrolens* (ATCC 4683); *Pseudomonas cissicola* (ATCC 33616); *Pseudomonas coronafaciens; Pseudomonas diterpeniphila; Pseudomonas elongata* (ATCC 10144); *Pseudomonas flectens* (ATCC 12775); *Pseudomonas azotoformans; Pseudomonas brenneri; Pseudomonas cedrella; Pseudomonas corrugata* (ATCC 29736); *Pseudomonas extremorientalis; Pseudomonas fluorescens* (ATCC 35858); *Pseudomonas gessardii; Pseudomonas libanensis; Pseudomonas mandelii* (ATCC 700871); *Pseudomonas marginalis* (ATCC 10844); *Pseudomonas migulae; Pseudomonas mucidolens* (ATCC 4685); *Pseudomonas orientalis; Pseudomonas rhodesiae; Pseudomonas synxantha* (ATCC 9890); *Pseudomonas tolaasii* (ATCC 33618); *Pseudomonas veronii* (ATCC 700474); *Pseudomonas frederiksbergensis; Pseudomonas geniculata* (ATCC 19374); *Pseudomonas gingeri; Pseudomonas graminis; Pseudomonas grimontii; Pseudomonas halodenitrificans; Pseudomonas halophila; Pseudomonas hibiscicola* (ATCC 19867); *Pseudomonas huttiensis* (ATCC 14670); *Pseudomonas hydrogenovora; Pseudomonas jessenii* (ATCC 700870); *Pseudomonas kilonensis; Pseudomonas lanceolata* (ATCC 14669); *Pseudomonas lini; Pseudomonas marginata* (ATCC 25417); *Pseudomonas mephitica* (ATCC 33665); *Pseudomonas denitrificans* (ATCC 19244); *Pseudomonas pertucinogena* (ATCC 190); *Pseudomonas pictorum* (ATCC 23328); *Pseudomonas psychrophila; Pseudomonas fulva* (ATCC 31418); *Pseudomonas monteilii* (ATCC 700476); *Pseudomonas mosselii; Pseudomonas oryzihabitans* (ATCC 43272); *Pseudomonas plecoglossicida* (ATCC 700383); *Pseudomonas putida* (ATCC 12633); *Pseudomonas reactans; Pseudomonas spinosa* (ATCC 14606); *Pseudomonas balearica; Pseudomonas luteola* (ATCC 43273); *Pseudomonas stutzeri* (ATCC 17588); *Pseudomonas amygdali* (ATCC 33614); *Pseudomonas avellanae* (ATCC 700331); *Pseudomonas caricapapayae* (ATCC 33615); *Pseudomonas cichorii* (ATCC 10857); *Pseudomonas ficuserectae* (ATCC 35104); *Pseudomonas fuscovaginae; Pseudomonas meliae* (ATCC 33050); *Pseudomonas syringae* (ATCC 19310); *Pseudomonas viridiflava* (ATCC 13223); *Pseudomonas thermocarboxydovorans* (ATCC 35961); *Pseudomonas thermotolerans; Pseudomonas thivervalensis; Pseudomonas vancouverensis* (ATCC 700688); *Pseudomonas wisconsinensis*; and *Pseudomonas xiamenensis*.

The host cell can be selected from "Gram-negative Proteobacteria Subgroup 17." "Gram-negative Proteobacteria Subgroup 17" is defined as the group of Proteobacteria known in the art as the "fluorescent Pseudomonads" including those belonging, e.g., to the following *Pseudomonas* species: *Pseudomonas azotoformans; Pseudomonas brenneri; Pseudomonas cedrella; Pseudomonas corrugata; Pseudomonas extremorientalis; Pseudomonas fluorescens; Pseudomonas gessardii; Pseudomonas libanensis; Pseudomonas mandelii; Pseudomonas marginalis; Pseudomonas migulae; Pseudomonas mucidolens; Pseudomonas orientalis; Pseudomonas rhodesiae; Pseudomonas synxantha; Pseudomonas tolaasii*; and *Pseudomonas veronii*.

Other suitable hosts include those classified in other parts of the reference, such as Gram (+) Proteobacteria. In one embodiment, the host cell is an *E. coli*. The genome sequence for *E. coli* has been established for *E. coli* MG1655 (Blattner, et al. (1997) The complete genome sequence of *Escherichia coli* K-12 Science 277 (5331): 1453-74) and DNA microarrays are available commercially for *E. coli* K12 (MWG Inc, High Point, N.C.). *E. coli* can be cultured in either a rich medium such as Luria-Bertani (LB) (10 g/L tryptone, 5 g/L NaCl, 5 g/L yeast extract) or a defined minimal medium such as M9 (6 g/L $Na_2HPO_4$, 3 g/L $KH_2PO_4$, 1 g/L $NH_4Cl$, 0.5 g/L NaCl, pH 7.4) with an appropriate carbon source such as 1% glucose. Routinely, an over night culture of *E. coli* cells is diluted and inoculated into fresh rich or minimal medium in either a shake flask or a fermentor and grown at 37° C.

A host can also be of mammalian origin, such as a cell derived from a mammal including any human or non-human mammal. Mammals can include, but are not limited to primates, monkeys, porcine, ovine, bovine, rodents, ungulates, pigs, swine, sheep, lambs, goats, cattle, deer, mules, horses, monkeys, apes, dogs, cats, rats, and mice.

A host cell may also be of plant origin. Any plant can be selected for the identification of genes and regulatory sequences. Examples of suitable plant targets for the isolation of genes and regulatory sequences would include but are not limited to alfalfa, apple, apricot, *Arabidopsis*, artichoke, arugula, asparagus, avocado, banana, barley, beans, beet, blackberry, blueberry, broccoli, brussels sprouts, cabbage, canola, cantaloupe, carrot, cassava, castorbean, cauliflower, celery, cherry, chicory, cilantro, citrus, clementines, clover, coconut, coffee, corn, cotton, cranberry, cucumber, Douglas fir, eggplant, endive, escarole, eucalyptus, fennel, figs, garlic, gourd, grape, grapefruit, honey dew, jicama, kiwifruit, lettuce, leeks, lemon, lime, Loblolly pine, linseed, mango, melon, mushroom, nectarine, nut, oat, oil palm, oil seed rape, okra, olive, onion, orange, an ornamental plant, palm, papaya, parsley, parsnip, pea, peach, peanut, pear, pepper, persimmon, pine, pineapple, plantain, plum, pomegranate, poplar, potato, pumpkin, quince, radiata pine, radiscchio, radish, rapeseed, raspberry, rice, rye, sorghum, Southern pine, soybean, spinach, squash, strawberry, sugarbeet, sugarcane, sunflower, sweet potato, sweetgum, tangerine, tea, tobacco, tomato, triticale, turf, turnip, a vine, watermelon, wheat, yams, and zucchini. In some embodiments, plants useful in the process are *Arabidopsis*, corn, wheat, soybean, and cotton.

For expression of a recombinant protein or peptide, or for modulation of an identified compensatory gene, any plant promoter can be used. A promoter may be a plant RNA polymerase II promoter. Elements included in plant promoters can be a TATA box or Goldberg-Hogness box, typically positioned approximately 25 to 35 basepairs upstream (5') of the transcription initiation site, and the CCAAT box, located between 70 and 100 basepairs upstream. In plants, the CCAAT box may have a different consensus sequence than the functionally analogous sequence of mammalian promoters (Messing et al. (1983) In: Genetic Engineering of Plants, Kosuge et al., eds., pp. 211-227). In addition, virtually all promoters include additional upstream activating sequences or enhancers (Benoist and Chambon (1981) *Nature* 290:304-310; Gruss et al. (1981) *Proc. Nat. Acad. Sci.* 78:943-947; and Khoury and Gruss (1983) *Cell* 27:313-314) extending from around −100 bp to −1,000 bp or more upstream of the transcription initiation site.

Protein Production/Fermentation

The process of the invention optimally leads to increased production of recombinant protein or peptide in a host cell. The increased production alternatively can be an increased level of properly processed protein or peptide per gram of protein produced, or per gram of host protein. The increased production can also be an increased level of recoverable protein or peptide produced per gram of recombinant or per gram of host cell protein. The increased production can also be any combination of increased total level and increased properly processed, active or soluble level of protein.

The improved expression of recombinant protein can be an increase in the solubility of the protein. The recombinant protein or peptide can be produced and recovered from the cytoplasm, periplasm or extracellular medium of the host cell. The protein or peptide can be insoluble or soluble. The protein or peptide can include one or more targeting sequences or sequences to assist purification.

Cell Growth

Transformation of the *Pseudomonas* host cells with the vector(s) may be performed using any transformation methodology known in the art, and the bacterial host cells may be transformed as intact cells or as protoplasts (i.e. including cytoplasts). Exemplary transformation methodologies include poration methodologies, e.g., electroporation, protoplast fusion, bacterial conjugation, and divalent cation treatment, e.g., calcium chloride treatment or CaCl/Mg2+ treatment, or other well known methods in the art. See, e.g., Morrison, J. Bact., 132:349-351 (1977); Clark-Curtiss & Curtiss, Methods in Enzymology, 101:347-362 (Wu et al., eds, 1983), Sambrook et al., Molecular Cloning, A Laboratory Manual (2nd ed. 1989); Kriegler, Gene Transfer and Expression: A Laboratory Manual (1990); and Current Protocols in Molecular Biology (Ausubel et al., eds., 1994)).

As used herein, the term "fermentation" includes both embodiments in which literal fermentation is employed and embodiments in which other, non-fermentative culture modes are employed. Fermentation may be performed at any scale. In one embodiment, the fermentation medium may be selected from among rich media, minimal media, and mineral salts media; a rich medium may be used, but is preferably avoided. In another embodiment either a minimal medium or a mineral salts medium is selected. In still another embodiment, a minimal medium is selected. In yet another embodiment, a mineral salts medium is selected. Mineral salts media are particularly preferred.

Mineral salts media consists of mineral salts and a carbon source such as, e.g., glucose, sucrose, or glycerol. Examples of mineral salts media include, e.g., M9 medium, *Pseudomonas* medium (ATCC 179), Davis and Mingioli medium (see, B D Davis & E S Mingioli (1950) in J. Bact. 60:17-28). The mineral salts used to make mineral salts media include those selected from among, e.g., potassium phosphates, ammonium sulfate or chloride, magnesium sulfate or chloride, and trace minerals such as calcium chloride, borate, and sulfates of iron, copper, manganese, and zinc. No organic nitrogen source, such as peptone, tryptone, amino acids, or a yeast extract, is included in a mineral salts medium. Instead, an inorganic nitrogen source is used and this may be selected from among, e.g., ammonium salts, aqueous ammonia, and gaseous ammonia. A preferred mineral salts medium will contain glucose as the carbon source. In comparison to mineral salts media, minimal media can also contain mineral salts and a carbon source, but can be supplemented with, e.g., low levels of amino acids, vitamins, peptones, or other ingredients, though these are added at very minimal levels.

In one embodiment, media can be prepared using the components listed in Table 5 below. The components can be added in the following order: first $(NH_4)HPO_4$, $KH_2PO_4$ and citric acid can be dissolved in approximately 30 liters of distilled water; then a solution of trace elements can be added, followed by the addition of an antifoam agent, such as Ucolub N 115. Then, after heat sterilization (such as at approximately 121° C.), sterile solutions of glucose $MgSO_4$ and thiamine-HCL can be added. Control of pH at approximately 6.8 can be achieved using aqueous ammonia. Sterile distilled water can then be added to adjust the initial volume to 371 minus the glycerol stock (123 mL). The chemicals are commercially available from various suppliers, such as Merck. This media can allow for a high cell density cultivation (HCDC) for growth of *Pseudomonas* species and related bacteria. The HCDC can start as a batch process which is followed by a two-phase fed-batch cultivation. After unlimited growth in the batch part, growth can be controlled at a reduced specific growth rate over a period of 3 doubling times in which the biomass concentration can increased several fold. Further details of such cultivation procedures is described by Riesenberg, D.; Schulz, V.; Knorre, W. A.; Pohl, H. D.; Korz, D.; Sanders, E. A.; Ross, A.; Deckwer, W. D. (1991) "High cell density cultivation of *Escherichia coli* at controlled specific growth rate" J Biotechnol: 20 (1) 17-27.

TABLE 5

Medium composition

| Component | Initial concentration |
|---|---|
| $KH_2PO_4$ | 13.3 g l$^{-1}$ |
| $(NH_4)_2HPO_4$ | 4.0 g l$^{-1}$ |
| Citric acid | 1.7 g l$^{-1}$ |
| $MgSO_4\text{-}7H_2O$ | 1.2 g l$^{-1}$ |
| Trace metal solution | 10 ml l$^{-1}$ |
| Thiamin HCl | 4.5 mg l$^{-1}$ |
| Glucose-$H_2O$ | 27.3 g l$^{-1}$ |
| Antifoam Ucolub N115 | 0.1 ml l$^{-1}$ |
| Feeding solution | |
| $MgSO_4\text{-}7H_2O$ | 19.7 g l$^{-1}$ |
| Glucose-$H_2O$ | 770 g l$^{-1}$ |
| $NH_3$ | 23 g |
| Trace metal solution | |
| 6 g l$^{-1}$ Fe(111) citrate 1.5 g l$^{-1}$ $MnCl_2\text{-}4H_2O$ | |
| 0.8 g l$^{-1}$ $ZmCH_2COO1_2\text{-}2H_2O$ 0.3 g l$^{-1}$ $H_3BO_3$ | |
| 0.25 g l$^{-1}$ $Na_2MoO_4\text{-}2H_2O$ 0.25 g l$^{-1}$ $CoCl_2$ $6H_2O$ | |
| 0.15 g l$^{-1}$ $CuCl_2$ $2H_2O$ 0.84 g l$^{-1}$ ethylene dinitrilo-tetracetic acid $Na_2$ sah $2H_2O$ (Tritriplex III, Merck) | |

The expression system according to the present invention can be cultured in any fermentation format. For example, batch, fed-batch, semi-continuous, and continuous fermentation modes may be employed herein.

The expression systems according to the present invention are useful for transgene expression at any scale (i.e. volume) of fermentation. Thus, e.g., microliter-scale, centiliter scale, and deciliter scale fermentation volumes may be used; and 1 Liter scale and larger fermentation volumes can be used. In one embodiment, the fermentation volume will be at or above 1 Liter. In another embodiment, the fermentation volume will be at or above 5 Liters, 10 Liters, 15 Liters, 20 Liters, 25 Liters, 50 Liters, 75 Liters, 100 Liters, 200 Liters, 500 Liters, 1,000 Liters, 2,000 Liters, 5,000 Liters, 10,000 Liters or 50,000 Liters.

In the present invention, growth, culturing, and/or fermentation of the transformed host cells is performed within a temperature range permitting survival of the host cells, preferably a temperature within the range of about 4° C. to about 55° C., inclusive. Thus, e.g., the terms "growth" (and "grow," "growing"), "culturing" (and "culture"), and "fermentation" (and "ferment" "fermenting"), as used herein in regard to the host cells of the present invention, inherently means "growth," "culturing," and "fermentation," within a temperature range of about 4° C. to about 55° C., inclusive. In addition, "growth" is used to indicate both biological states of active cell division and/or enlargement, as well as biological states in which a non-dividing and/or non-enlarging cell is being metabolically sustained, the latter use of the term "growth" being synonymous with the term "maintenance."

Cell Density

An additional advantage in using Pseudomonas fluorescens in expressing recombinant secreted proteins includes the ability of Pseudomonas fluorescens to be grown in high cell densities compared to E. coli or other bacterial expression systems. To this end, Pseudomonas fluorescens expressions systems according to the present invention can provide a cell density of about 20 g/L or more. The Pseudomonas fluorescens expressions systems according to the present invention can likewise provide a cell density of at least about 70 g/L, as stated in terms of biomass per volume, the biomass being measured as dry cell weight.

In one embodiment, the cell density will be at least 20 g/L. In another embodiment, the cell density will be at least 25 g/L, 30 g/L, 35 g/L, 40 g/L, 45 g/L, 50 g/L, 60 g/L, 70 g/L, 80 g/L, 90 g/L., 100 g/L, 110 g/L, 120 g/L, 130 g/L, 140 g/L, or at least 150 g/L.

In another embodiments, the cell density at induction will be between 20 g/L and 150 g/L; 20 g/L and 120 g/L; 20 g/L and 80 g/L; 25 g/L and 80 g/L; 30 g/L and 80 g/L; 35 g/L and 80 g/L; 40 g/L and 80 g/L; 45 g/L and 80 g/L; 50 g/L and 80 g/L; 50 g/L and 75 g/L; 50 g/L and 70 g/L; 40 g/L and 80 g/L.

Isolation of Protein or Peptide of Interest

Generally, the process provides for an increase in the level of correctly or properly processed recombinant protein expressed, in comparison with conventional expression systems. In particular, the invention provides an increased level of properly In certain embodiments, the invention provides a process for improving the solubility of a recombinant protein or peptide in a host cell. The term "soluble" as used herein means that the protein is not precipitated by centrifugation at between approximately 5,000 and 20,000× gravity when spun for 10-30 minutes in a buffer under physiological conditions. Soluble proteins are not part of an inclusion body or other precipitated mass. Similarly, "insoluble" means that the protein or peptide that can be precipitated by centrifugation at between 5,000 and 20,000× gravity when spun for 10-30 minutes in a buffer under physiological conditions. Insoluble proteins or peptides can be part of an inclusion body or other precipitated mass. The term "inclusion body" is meant to include any intracellular body contained within a cell wherein an aggregate of proteins or peptides have been sequestered.

The invention can also improve recovery of active recombinant proteins or peptides. Levels of active protein can be measured, for example, by measuring the interaction between an identified and a parent polypeptide, polypeptide variant, segment-substituted polypeptide and/or residue-substituted polypeptide by any convenient in vitro or in vivo assay. Thus, in vitro assays can be used to determine any detectable interaction between an identified protein and a peptide of interest, e.g. between enzyme and substrate, between hormone and hormone receptor, between antibody and antigen, etc. Such detection can include the measurement of colorimetric changes, changes in radioactivity, changes in solubility, changes in molecular weight as measured by gel electrophoresis and/or gel exclusion processes, etc. In vivo assays include, but are not limited to, assays to detect physiological effects, e.g. weight gain, change in electrolyte balance, change in blood clotting time, changes in clot dissolution and the induction of antigenic response. Generally, any in vivo assay can be used so long as a variable parameter exists so as to detect a change in the interaction between the identified and the polypeptide of interest. See, for example, U.S. Pat. No. 5,834,250.

To release recombinant proteins from the periplasm, treatments involving chemicals such as chloroform (Ames et al. (1984) J. Bacteriol., 160: 1181-1183), guanidine-HCl, and Triton X-100 (Naglak and Wang (1990) Enzyme Microb. Technol., 12: 603-611) have been used. However, these chemicals are not inert and may have detrimental effects on many recombinant protein products or subsequent purification procedures. Glycine treatment of E. coli cells, causing permeabilization of the outer membrane, has also been reported to release the periplasmic contents (Ariga et al. (1989) J. Ferm. Bioeng., 68: 243-246). The most widely used methods of periplasmic release of recombinant protein are osmotic shock (Nosal and Heppel (1966) J. Biol. Chem., 241: 3055-3062; Neu and Heppel (1965) J. Biol. Chem., 240: 3685-3692), hen eggwhite (HEW)-lysozyme/ethylenediamine tetraacetic acid (EDTA) treatment (Neu and Heppel (1964) J. Biol. Chem., 239: 3893-3900; Witholt et al. (1976) Biochim. Biophys. Acta, 443: 534-544; Pierce et al. (1995) ICheme Research. Event, 2: 995-997), and combined HEW-lysozyme/osmotic shock treatment (French et al. (1996) Enzyme and Microb. Tech., 19: 332-338). The French method involves resuspension of the cells in a fractionation buffer followed by recovery of the periplasmic fraction, where osmotic shock immediately follows lysozyme treatment. The effects of overexpression of the recombinant protein, S. thermoviolaceus α-amylase, and the growth phase of the host organism on the recovery are also discussed.

Typically, these procedures include an initial disruption in osmotically-stabilizing medium followed by selective release in non-stabilizing medium. The composition of these media (pH, protective agent) and the disruption methods used (chloroform, HEW-lysozyme, EDTA, sonication) vary among specific procedures reported. A variation on the HEW-lysozyme/EDTA treatment using a dipolar ionic detergent in place of EDTA is discussed by Stabel et al. (1994) Veterinary Microbiol., 38: 307-314. For a general review of use of intracellular lytic enzyme systems to disrupt E. coli, see Dabora and Cooney (1990) in Advances in Biochemical Engineering/Biotechnology, Vol. 43, A. Fiechter, ed. (Springer-Verlag: Berlin), pp. 11-30.

Conventional methods for the recovery of recombinant protein from the cytoplasm, as soluble protein or refractile particles, involved disintegration of the bacterial cell by mechanical breakage. Mechanical disruption typically involves the generation of local cavitation in a liquid suspension, rapid agitation with rigid beads, sonication, or grinding of cell suspension (Bacterial Cell Surface Techniques, Hancock and Poxton (John Wiley & Sons Ltd, 1988), Chapter 3, p. 55).

HEW-lysozyme acts biochemically to hydrolyze the peptidoglycan backbone of the cell wall. The method was first developed by Zinder and Arndt (1956) *Proc. Natl. Acad. Sci. USA,* 42: 586-590, who treated *E. coli* with egg albumin (which contains HEW-lysozyme) to produce rounded cellular spheres later known as spheroplasts. These structures retained some cell-wall components but had large surface areas in which the cytoplasmic membrane was exposed. U.S. Pat. No. 5,169,772 discloses a method for purifying heparinase from bacteria comprising disrupting the envelope of the bacteria in an osmotically-stabilized medium, e.g., 20% sucrose solution using, e.g., EDTA, lysozyme, or an organic compound, releasing the non-heparinase-like proteins from the periplasmic space of the disrupted bacteria by exposing the bacteria to a low-ionic-strength buffer, and releasing the heparinase-like proteins by exposing the low-ionic-strength-washed bacteria to a buffered salt solution.

Many different modifications of these methods have been used on a wide range of expression systems with varying degrees of success (Joseph-Liazun et al. (1990) *Gene,* 86: 291-295; Carter et al. (1992) *Bio/Technology,* 10: 163-167). Efforts to induce recombinant cell culture to produce lysozyme have been reported. EP 0 155 189 discloses a means for inducing a recombinant cell culture to produce lysozymes, which would ordinarily be expected to kill such host cells by means of destroying or lysing the cell wall structure.

U.S. Pat. No. 4,595,658 discloses a method for facilitating externalization of proteins transported to the periplasmic space of *E. coli.* This method allows selective isolation of proteins that locate in the periplasm without the need for lysozyme treatment, mechanical grinding, or osmotic shock treatment of cells. U.S. Pat. No. 4,637,980 discloses producing a bacterial product by transforming a temperature-sensitive lysogen with a DNA molecule that codes, directly or indirectly, for the product, culturing the transformant under permissive conditions to express the gene product intracellularly, and externalizing the product by raising the temperature to induce phage-encoded functions. Asami et al. (1997) *J. Ferment. and Bioeng.,* 83: 511-516 discloses synchronized disruption of *E. coli* cells by T4 phage infection, and Tanji et al. (1998) *J. Ferment. and Bioeng.,* 85: 74-78 discloses controlled expression of lysis genes encoded in T4 phage for the gentle disruption of *E. coli* cells.

Upon cell lysis, genomic DNA leaks out of the cytoplasm into the medium and results in significant increase in fluid viscosity that can impede the sedimentation of solids in a centrifugal field. In the absence of shear forces such as those exerted during mechanical disruption to break down the DNA polymers, the slower sedimentation rate of solids through viscous fluid results in poor separation of solids and liquid during centrifugation. Other than mechanical shear force, there exist nucleolytic enzymes that degrade DNA polymer. In *E. coli,* the endogenous gene endA encodes for an endonuclease (molecular weight of the mature protein is approx. 24.5 kD) that is normally secreted to the periplasm and cleaves DNA into oligodeoxyribonucleotides in an endonucleolytic manner. It has been suggested that endA is relatively weakly expressed by *E. coli* (Wackernagel et al. (1995) *Gene* 154: 55-59).

In one embodiment, no additional disulfide-bond-promoting conditions or agents are required in order to recover disulfide-bond-containing identified polypeptide in active, soluble form from the host cell. In one embodiment, the transgenic peptide, polypeptide, protein, or fragment thereof has a folded intramolecular conformation in its active state. In one embodiment, the transgenic peptide, polypeptide, protein, or fragment contains at least one intramolecular disulfide bond in its active state; and perhaps up to 2, 4, 6, 8, 10, 12, 14, 16, 18, or 20 or more disulfide bonds.

The proteins of this invention may be isolated purified to substantial purity by standard techniques well known in the art, including, but not limited to, ammonium sulfate or ethanol precipitation, acid extraction, anion or cation exchange chromatography, phosphocellulose chromatography, hydrophobic interaction chromatography, affinity chromatography, nickel chromatography, hydroxylapatite chromatography, reverse phase chromatography, lectin chromatography, preparative electrophoresis, detergent solubilization, selective precipitation with such substances as column chromatography, immunopurification methods, and others. For example, proteins having established molecular adhesion properties can be reversibly fused a ligand. With the appropriate ligand, the protein can be selectively adsorbed to a purification column and then freed from the column in a relatively pure form. The fused protein is then removed by enzymatic activity. In addition, protein can be purified using immunoaffinity columns or Ni-NTA columns. General techniques are further described in, for example, R. Scopes, Protein Purification: Principles and Practice, Springer-Verlag: N.Y. (1982); Deutscher, Guide to Protein Purification, Academic Press (1990); U.S. Pat. No. 4,511,503; S. Roe, Protein Purification Techniques: A Practical Approach (Practical Approach Series), Oxford Press (2001); D. Bollag, et al., Protein Methods, Wiley-Lisa, Inc. (1996); A K Patra et al., Protein Expr Purif, 18 (2): p/ 182-92 (2000); and R. Mukhija, et al., Gene 165 (2): p. 303-6 (1995). See also, for example, Ausubel, et al. (1987 and periodic supplements); Deutscher (1990) "Guide to Protein Purification," Methods in Enzymology vol. 182, and other volumes in this series; Coligan, et al. (1996 and periodic Supplements) Current Protocols in Protein Science Wiley/Greene, NY; and manufacturer's literature on use of protein purification products, e.g., Pharmacia, Piscataway, N.J., or Bio-Rad, Richmond, Calif. Combination with recombinant techniques allow fusion to appropriate segments, e.g., to a FLAG sequence or an equivalent which can be fused via a protease-removable sequence. See also, for example, Hochuli (1989) Chemische Industrie 12:69-70; Hochuli (1990) "Purification of Recombinant Proteins with Metal Chelate Absorbent" in Setlow (ed.) Genetic Engineering, Principle and Methods 12:87-98, Plenum Press, NY; and Crowe, et al. (1992) QIAexpress: The High Level Expression & Protein Purification System QUIAGEN, Inc., Chatsworth, Calif.

Detection of the expressed protein is achieved by methods known in the art and include, for example, radioimmunoassays, Western blotting techniques or immunoprecipitation.

The recombinantly produced and expressed enzyme can be recovered and purified from the recombinant cell cultures by numerous methods, for example, high performance liquid chromatography (HPLC) can be employed for final purification steps, as necessary.

Certain proteins expressed in this invention may form insoluble aggregates ("inclusion bodies"). Several protocols are suitable for purification of proteins from. inclusion bodies. For example, purification of inclusion bodies typically involves the extraction, separation and/or purification of inclusion bodies by disruption of the host cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension is typically lysed using 2-3 passages through a French Press. The cell suspension can also be homogenized using a Polytron (Brinkrnan Instruments) or sonicated on ice. Alternate methods of lysing bacteria are apparent to those of skill in the art (see, e.g., Sambrook et al., supra; Ausubel et al., supra).

If necessary, the inclusion bodies can be solubilized, and the lysed cell suspension typically can be centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art.

Alternatively, it is possible to purify the recombinant proteins or peptides from the host periplasm. After lysis of the host cell, when the recombinant protein is exported into the periplasm of the host cell, the periplasmic fraction of the bacteria can be isolated by cold osmotic shock in addition to other methods known to those skilled in the art. To isolate recombinant proteins from the periplasm, for example, the bacterial cells can be centrifuged to form a pellet. The pellet can be resuspended in a buffer containing 20% sucrose. To lyse the cells, the bacteria can be centrifuged and the pellet can be resuspended in ice-cold 5 mM $MgSO_4$ and kept in an ice bath for approximately 10 minutes. The cell suspension can be centrifuged and the supernatant decanted and saved. The recombinant proteins present in the supernatant can be separated from the host proteins by standard separation techniques well known to those of skill in the art.

An initial salt fractionation can separate many of the unwanted host cell proteins (or proteins derived from the cell culture media) from the recombinant protein of interest. One such example can be ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

The molecular weight of a recombinant protein can be used to isolated it from proteins of greater and lesser size using ultrafiltration through membranes of different pore size (for example, Amicon or Millipore membranes). As a first step, the protein mixture can be ultrafiltered through a membrane with a pore size that has a lower molecular weight cut-off than the molecular weight of the protein of interest. The retentate of the ultrafiltration can then be ultrafiltered against a membrane with a molecular cut off greater than the molecular weight of the protein of interest. The recombinant protein will pass through the membrane into the filtrate. The filtrate can then be chromatographed as described below.

Recombinant proteins can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

In practice, heterologous proteins targeted to the periplasm are often found in the broth (see European Patent No. EP 0 288 451), possibly because of damage to or an increase in the fluidity of the outer cell membrane. The rate of this "passive" secretion may be increased by using a variety of mechanisms that permeabilize the outer cell membrane: colicin (Miksch et al. (1997) *Arch. Microbiol.* 167: 143-150); growth rate (Shokri et al. (2002) *App Miocrobiol Biotechnol* 58:386-392); TolIII overexpression (Wan and Baneyx (1998) *Protein Expression Purif.* 14: 13-22); bacteriocin release protein (Hsiung et al. (1989) *Bio/Technology* 7: 267-71), colicin A lysis protein (Lloubes et al. (1993) *Biochimie* 75: 451-8) mutants that leak periplasmic proteins (Furlong and Sundstrom (1989) *Developments in Indus. Microbio.* 30: 141-8); fusion partners (Jeong and Lee (2002) *Appl. Environ. Microbio.* 68: 4979-4985); recovery by osmotic shock (Taguchi et al. (1990) *Biochimica Biophysica Acta* 1049: 278-85). Transport of engineered proteins to the periplasmic space with subsequent localization in the broth has been used to produce properly folded and active proteins in *E. coli* (Wan and Baneyx (1998) *Protein Expression Purif.* 14: 13-22; Simmons et al. (2002) *J. Immun. Meth.* 263: 133-147; Lundell et al. (1990) *J. Indust. Microbio.* 5: 215-27).

Gram-negative bacteria have evolved numerous systems for the export of proteins across their dual membranes (see FIG. 1). These routes of secretion include, e.g.: the ABC (Type I) pathway, the Path/Fla (Type III) pathway, and the Path/Vir (Type IV) pathway for one-step translocation across both the plasma and outer membrane; the Sec (Type II), Tat, MscL, and Holins pathways for translocation across the plasma membrane; and the Sec-plus-fimbrial usher porin (FUP), Sec-plus-autotransporter (AT), Sec-plus-two partner secretion (TPS), Sec-plus-main terminal branch (MTB), and Tat-plus-MTB pathways for two-step translocation across the plasma and outer membranes. Not all bacteria have all of these secretion pathways.

Three protein systems (types I, III and IV) secrete proteins across both membranes in a single energy-coupled step. Four systems (Sec, Tat, MscL and Holins) secrete only across the inner membrane, and four other systems (MTB, FUP, AT and TPS) secrete only across the outer membrane.

Proteins that are transported into the periplasm using the secretion signals or host cells of the invention, can also be actively exported into the extracellular media in a further step. Known mechanisms for active transport are generally through an autotransporter, a two partner secretion system, a main terminal branch system or a fimbrial usher porin.

Proteins that are transported into the periplasm using the secretion signals or host cells of the invention, can also be actively exported into the extracellular media in a further step. Known mechanisms for active transport are generally through an autotransporter, a two partner secretion system, a main terminal branch system or a fimbrial usher porin.

An protein that is transported through an autotransporter (AT) pathway usually contains an N-terminal Sec-type signal peptide, a central passenger domain and a C-terminal 250-300 amino acid residues of α-domain. The α-domains of different autotransporters are highly homologous, whereas the passenger domains vary significantly in sequence and size. Following secretion across the inner membrane by the Sec system and cleavage of the signal peptide, oligomers of the α-domains form an outer membrane porin, through which the passenger domain is secreted (Veiga et al. (2002) *EMBO J.*, 21:2122-2131). The passenger domain is either released to the environment or remains on the cell surface. Most of the autotransporters are related to the virulence of Gram-negative pathogens.

The two-partner secretion (TPS) system is functionally similar to the AT system, though the proteins are not known to share sequence homology. A TPS system is composed of two signal-peptide-containing proteins encoded by neighboring genes. One protein has a passenger domain and the other has an α-domain. Both proteins are secreted to the periplasm by the Sec system and the protein with the passenger domain is further exported through the outer membrane pore formed by the protein with the α-domain (Jacob-Dubuisson et al. (2001) *Mol Microbiol.* 40:306-13.). Most substrate proteins of the TPS systems are large proteins from 1651 to 5640 amino acids. Although they are highly similar in the N-terminal 250 residues, which is the targeting sequence for the transporters, their C-terminal sequences are very divergent.

The main terminal branch (MTB) is a large complex that translocates already folded proteins from the periplasm to the extracellular medium. The complex consists of at least 10 protein constituents, some of which share sequence homology with the type 4 pilus biogenesis system (Pugsley (1993) *Microbiol. Rev.* 57:50-108). Genes encoding a functional MTB system commonly form a cluster in the genome. The targeting signal and the molecular mechanism of protein secretion by the MTB are poorly understood.

The FUP system is responsible for the biogenesis of numerous fimbriae (pili) in Gram-negative proteobacteria and cyanobacteria. The operon encoding the structural proteins of each fimbrium also encodes a fimbrium-specific periplasmic chaperone protein and a fimbrium-specific outer membrane usher protein. All these proteins can be synthesized as precursor proteins with the Sec-type signal peptides. Following translocation across the inner membrane by the Sec system, the pilus subunits are bound to the chaperone proteins, which prevent the self-assembly of pili in the periplasm. Interaction between the chaperone and the usher protein releases the protein subunits, which subsequently interact with each other and are secreted through the usher protein across the outer membrane.

Renaturation and Refolding

Insoluble protein can be renatured or refolded to generate secondary and tertiary protein structure conformation. Protein refolding steps can be used, as necessary, in completing configuration of the recombinant product. Refolding and renaturation can be accomplished using an agent that is known in the art to promote dissociation/association of proteins. For example, the protein can be incubated with dithiothreitol followed by incubation with oxidized glutathione disodium salt followed by incubation with a buffer containing a refolding agent such as urea.

Recombinant protein can also be renatured, for example, by dialyzing it against phosphate-buffered saline (PBS) or 50 mM Na-acetate, pH 6 buffer plus 200 mM NaCl. Alternatively, the protein can be refolded while immobilized on a column, such as the Ni NTA column by using a linear 6M-1M urea gradient in 500 mM NaCl, 20% glycerol, 20 mM Tris/HCl pH 7.4, containing protease inhibitors. The renaturation can be performed over a period of 1.5 hours or more. After renaturation the proteins can be eluted by the addition of 250 mM immidazole. Immidazole can be removed by a final dialyzing step against PBS or 50 mM sodium acetate pH 6 buffer plus 200 mM NaCl. The purified protein can be stored at 4° C. or frozen at −80° C.

Other methods include, for example, those that may be described in M H Lee et al., Protein Expr. Purif, 25 (1): p. 166-73 (2002), W. K. Cho et al., J. Biotechnology, 77 (2-3): p. 169-78 (2000), Ausubel, et al. (1987 and periodic supplements), Deutscher (1990) "Guide to Protein Purification," Methods in Enzymology vol. 182, and other volumes in this series, Coligan, et al. (1996 and periodic Supplements) Current Protocols in Protein Science Wiley/Greene, NY, S. Roe, Protein Purification Techniques: A Practical Approach (Practical Approach Series), Oxford Press (2001); D. Bollag, et al., Protein Methods, Wiley-Lisa, Inc. (1996)

Active Protein or Peptide Analysis

Active proteins can have a specific activity of at least 20%, 30%, or 40%, and preferably at least 50%, 60%, or 70%, and most preferably at least 80%, 90%, or 95% that of the native protein or peptide that the sequence is derived from. Further, the substrate specificity ($k_{cat}/K_m$) is optionally substantially similar to the native protein or peptide. Typically, $k_{cat}/K_m$ will be at least 30%, 40%, or 50%, that of the native protein or peptide; and more preferably at least 60%, 70%, 80%, or 90%. Methods of assaying and quantifying measures of protein and peptide activity and substrate specificity ($k_{cat}/K_m$), are well known to those of skill in the art.

The activity of a recombinant protein or peptide produced in accordance with the present invention by can be measured by any protein specific conventional or standard in vitro or in vivo assay known in the art. The activity of the *Pseudonmonas* produced secreted recombinant protein or peptide can be compared with the activity of the corresponding native protein to determine whether the recombinant protein exhibits substantially similar or equivalent activity to the activity generally observed in the native protein or peptide under the same or similar physiological conditions.

The activity of the recombinant protein can be compared with a previously established native protein or peptide standard activity. Alternatively, the activity of the recombinant protein or peptide can be determined in a simultaneous, or substantially simultaneous, comparative assay with the native protein or peptide. For example, an in vitro assays can be used to determine any detectable interaction between a recombinant protein or peptide and a target, e.g. between an expressed enzyme and substrate, between expressed hormone and hormone receptor, between expressed antibody and antigen, etc. Such detection can include the measurement of colorimetric changes, proliferation changes, cell death, cell repelling, changes in radioactivity, changes in solubility, changes in molecular weight as measured by gel electrophoresis and/or gel exclusion methods, phosphorylation abilities, antibody specificity assays such as ELISA assays, etc. In addition, in vivo assays include, but are not limited to, assays to detect physiological effects of the *Pseudomonas* produced protein or peptide in comparison to physiological effects of the native protein or peptide, e.g. weight gain, change in electrolyte balance, change in blood clotting time, changes in clot dissolution and the induction of antigenic response. Generally, any in vitro or in vivo assay can be used to determine the active nature of the *Pseudomonas* produced recombinant protein or peptide that allows for a comparative analysis to the native protein or peptide so long as such activity is assayable. Alternatively, the proteins or peptides produced in the present invention can be assayed for the ability to stimulate or inhibit interaction between the protein or peptide and a molecule that normally interacts with the protein or peptide, e.g. a substrate or a component of the signal pathway that the native protein normally interacts. Such assays can typically include the steps of combining the protein with a substrate molecule under conditions that allow the protein or peptide to interact with the target molecule, and detect the biochemical consequence of the interaction with the protein and the target molecule.

Assays that can be utilized to determine protein or peptide activity are described, for example, in Ralph, P. J., et al. (1984) J. Immunol. 132:1858 or Saiki et al. (1981) J. Immunol. 127:1044, Steward, W. E. II (1980) The Interferon Systems. Springer-Verlag, Vienna and New York, Broxmeyer, H. E., et al. (1982) Blood 60:595, "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987, A K Patra et al., Protein Expr Purif, 18 (2): p/182-92 (2000), Kodama et al., J. Biochem. 99: 1465-1472 (1986); Stewart et al., Proc. Nat'l Acad. Sci. USA 90: 5209-5213 (1993); (Lombillo et al., J. Cell Biol. 128:107-115 (1995); (Vale et al., Cell 42:39-50 (1985)

Proteins of Interest

The host cell can be designed to express a recombinant protein or peptide. These can be of any species and of any size. However, in certain embodiments, the recombinant protein or peptide is a therapeutically useful protein or peptide. In some embodiments, the protein can be a mammalian protein, for example a human protein, and can be, for example, a growth factor, a cytokine, a chemokine or a blood protein. The recombinant protein or peptide can be processed in a similar manner to the native protein or peptide. In certain embodiments, the protein or peptide does not include a secretion signal in the coding sequence. In certain embodiments, the recombinant protein or peptide is less than 100 kD, less than 50 kD, or less than 30 kD in size. In certain embodiments, the recombinant protein or peptide is a peptide of at least 5, 10, 15, 20, 30, 40, 50 or 100 amino acids.

Extensive sequence information required for molecular genetics and genetic engineering techniques is widely publicly available. Access to complete nucleotide sequences of mammalian, as well as human, genes, cDNA sequences, amino acid sequences and genomes can be obtained from GenBank on the internet at www.ncbi.nlm.nih.gov/Entrez. Additional information can also be obtained from GeneCards, an electronic encyclopedia integrating information about genes and their products and biomedical applications from the Weizmann Institute of Science Genome and Bioinformatics on the internet at bioinformatics.weizmann.ac.il/cards/), nucleotide sequence information can be also obtained from the EMBL Nucleotide Sequence Database (on the internet at www.ebi.ac.uk/embl/) or the DNA Databank or Japan (DDBJ, on the internet at www.ddbi.nig.ac.ii/; additional sites for information on amino acid sequences include Georgetown's protein information resource website (www-nbrf.Reorgetown.edu/pirl) and Swiss-Prot (au.expasy.org/sprot/sprot-top.html).

Examples of proteins that can be expressed in this invention include molecules such as, e.g., renin, a growth hormone, including human growth hormone; bovine growth hormone; growth hormone releasing factor; parathyroid hormone; thyroid stimulating hormone; lipoproteins; α1-antitrypsin; insulin A-chain; insulin B-chain; proinsulin; thrombopoietin; follicle stimulating hormone; calcitonin; luteinizing hormone; glucagon; clotting factors such as factor VIIIC, factor IX, tissue factor, and von Willebrands factor; anti-clotting factors such as Protein C; atrial naturietic factor; lung surfactant; a plasminogen activator, such as urokinase or human urine or tissue-type plasminogen activator (t-PA); bombesin; thrombin; hemopoietic growth factor; tumor necrosis factor-alpha and -beta; enkephalinase; a serum albumin such as human serum albumin; mullerian-inhibiting substance; relaxin A-chain; relaxin B-chain; prorelaxin; mouse gonadotropin-associated peptide; a microbial protein, such as beta-lactamase; Dnase; inhibin; activin; vascular endothelial growth factor (VEGF); receptors for hormones or growth factors; integrin; protein A or D; rheumatoid factors; a neurotrophic factor such as brain-derived neurotrophic factor (BDNF), neurotrophin-3, -4, -5, or -6 (NT-3, NT-4, NT-5, or NT-6), or a nerve growth factor such as NGF-β; cardiotrophins (cardiac hypertrophy factor) such as cardiotrophin-1 (CT-1); platelet-derived growth factor (PDGF); fibroblast growth factor such as aFGF and bFGF; epidermal growth factor (EGF); transforming growth factor (TGF) such as TGF-alpha and TGF-β, including TGF-β1, TGF-β2, TGF-β3, TGF-β4, or TGF-β5; insulin-like growth factor-I and -II (IGF-I and IGF-II); des(1-3)-IGF-I (brain IGF-I), insulin-like growth factor binding proteins; CD proteins such as CD-3, CD-4, CD-8, and CD-19; erythropoietin; osteoinductive factors; immunotoxins; a bone morphogenetic protein (BMP); an interferon such as interferon-alpha, -beta, and -gamma; colony stimulating factors (CSFs), e.g., M-CSF, GM-CSF, and G-CSF; interleukins (ILs), e.g., IL-1 to IL-10; anti-HER-2 antibody; superoxide dismutase; T-cell receptors; surface membrane proteins; decay accelerating factor; viral antigen such as, for example, a portion of the AIDS envelope; transport proteins; homing receptors; addressins; regulatory proteins; antibodies; and fragments of any of the above-listed polypeptides.

In certain embodiments, the protein or peptide can be selected from IL-1, IL-1a, IL-1b, IL-2, IL-3, IL-4, IL-5, IL-6, IL-7, IL-8, IL-9, IL-10, IL-11, IL-12, IL-12elasti, IL-13, IL-15, IL-16, IL-18, IL-18BPa, IL-23, IL-24, VIP, erythropoietin, GM-CSF, G-CSF, M-CSF, platelet derived growth factor (PDGF), MSF, FLT-3 ligand, EGF, fibroblast growth factor (FGF; e.g., αFGF (FGF-1), βFGF (FGF-2), FGF-3, FGF-4, FGF-5, FGF-6, or FGF-7), insulin-like growth factors (e.g., IGF-1, IGF-2); tumor necrosis factors (e.g., TNF, Lymphotoxin), nerve growth factors (e.g., NGF), vascular endothelial growth factor (VEGF); interferons (e.g., IFN-α, IFN-β, IFN-γ); leukemia inhibitory factor (LIF); ciliary neurotrophic factor (CNTF); oncostatin M; stem cell factor (SCF); transforming growth factors (e.g., TGF-α, TGF-β1, TGF-β2, TGF-β3); TNF superfamily (e.g., LIGHT/TNFSF14, STALL-1/TNFSF13B (BLy5, BAFF, THANK), TNFalpha/TNFSF2 and TWEAK/TNFSF12); or chemokines (BCA-1/BLC-1, BRAK/Kec, CXCL16, CXCR3, ENA-78/LIX, Eotaxin-1, Eotaxin-2/MPIF-2, Exodus-2/SLC, Fractalkine/Neurotactin, GROalpha/MGSA, HCC-1, I-TAC, Lymphotactin/ATAC/SCM, MCP-1/MCAF, MCP-3, MCP-4, MDC/STCP-1/ABCD-1, MIP-1□, MIP-1□, MIP-2□/GRO□, MIP-3□/Exodus/LARC, MIP-3/Exodus-3/ELC, MIP-4/PARC/DC-CK1, PF-4, RANTES, SDF1, TARC, or TECK).

In one embodiment of the present invention, the production of recombinant multi-subunit proteins or peptides by a host cell of the species *Pseudomonas* is provided. Multisubunit proteins that can be expressed include homomeric and heteromeric proteins. The multisubunit proteins may include two or more subunits, that may be the same or different. For example, the protein may be a homomeric protein comprising 2, 3, 4, 5, 6, 7, 8, 9, 10, 11, 12 or more subunits. The protein also may be a heteromeric protein including 2, 3, 4, 5, 6, 7, 8, 9, 10, 11, 12, or more subunits. Exemplary multisubunit proteins include: receptors including ion channel receptors; extracellular matrix proteins including chondroitin; collagen; immunomodulators including MHC proteins, full chain antibodies, and antibody fragments; enzymes including RNA polymerases, and DNA polymerases; and membrane proteins.

In one embodiment of the present invention, the production of blood proteins by a host cell is provided. The blood proteins expressed in this embodiment include but are not limited to carrier proteins, such as albumin, including human and bovine albumin, transferrin, recombinant transferrin half-molecules, haptoglobin, fibrinogen and other coagulation factors, complement components, immunoglobulins, enzyme inhibitors, precursors of substances such as angiotensin and bradykinin, insulin, endothelin, and globulin, including alpha, beta, and gamma-globulin, and other types of proteins, peptides, and fragments thereof found primarily in the blood of mammals. The amino acid sequences for numerous blood proteins have been reported (see, S. S. Baldwin (1993) *Comp. Biochem Physiol.* 106b:203-218), including the amino acid sequence for human serum albumin (Lawn, L. M., et al. (1981) *Nucleic Acids Research*, 9:6103-6114.) and human serum transferrin (Yang, F. et al. (1984) *Proc. Natl. Acad. Sci. USA* 81:2752-2756).

In one embodiment of the present invention, the production of recombinant enzymes or co-factors by a host cell of the species *Pseudomonas fluorescens* is provided. The enzymes and co-factors expressed in this embodiment include but are not limited to aldolases, amine oxidases, amino acid oxidases, aspartases, $B_{12}$ dependent enzymes, carboxypeptidases, carboxyesterases, carboxylyases, chemotrypsin, CoA requiring enzymes, cyanohydrin synthetases, cystathione synthases, decarboxylases, dehydrogenases, alcohol dehydrogenases, dehydratases, diaphorases, dioxygenases, enoate reductases, epoxide hydrases, fumerases, galactose oxidases, glucose isomerases, glucose oxidases, glycosyltrasferases, methyltransferases, nitrile hydrases, nucleoside phosphorylases, oxidoreductases, oxynitilases, peptidases, glycosyltrasferases, peroxidases, enzymes fused to a therapeutically active polypeptide, tissue plasminogen activator; urokinase, reptilase, streptokinase; catalase, superoxide dismutase; Dnase, amino acid hydrolases (e.g., asparaginase, amidohydrolases); carboxypeptidases; proteases, trypsin, pepsin, chymotrypsin, papain, bromelain, collagenase; neuraminidase; lactase, maltase, sucrase, and arabinofuranosidases.

In one embodiment of the present invention, the production of recombinant single chain, Fab fragments and/or full chain antibodies or fragments or portions thereof by a host cell of the species *Pseudomonas fluorescens* is provided. A single-chain antibody can include the antigen-binding regions of antibodies on a single stably-folded polypeptide chain. Fab fragments can be a piece of a particular antibody. The Fab fragment can contain the antigen binding site. The Fab fragment can contains 2 chains: a light chain and a heavy chain fragment. These fragments can be linked via a linker or a disulfide bond.

The coding sequence for the recombinant protein or peptide can be a native coding sequence for the target polypeptide, if available, but will more preferably be a coding sequence that has been selected, improved, or optimized for use in the selected expression host cell: for example, by synthesizing the gene to reflect the codon use bias of a *Pseudomonas* species such as *P. fluorescens*. The gene(s) that result will have been constructed within or will be inserted into one or more vector, which will then be transformed into the expression host cell. Nucleic acid or a polynucleotide said to be provided in an "expressible form" means nucleic acid or a polynucleotide that contains at least one gene that can be expressed by the selected bacterial expression host cell.

In certain embodiments, the protein of interest is, or is substantially homologous to, a native protein, such as a native mammalian or human protein. In these embodiments, the protein is not found in a concatameric form, but is linked only to a secretion signal and optionally a tag sequence for purification and/or recognition.

In other embodiments, the protein of interest is a protein that is active at a temperature from about 20 to about 42° C. In one embodiment, the protein is active at physiological temperatures and is inactivated when heated to high or extreme temperatures, such as temperatures over 65° C.

In one embodiment, the protein of interest is a protein that is active at a temperature from about 20 to about 42° C. and/or is inactivated when heated to high or extreme temperatures, such as temperatures over 65° C.; is, or is substantially homologous to, a native protein, such as a native mammalian or human protein and not expressed from nucleic acids in concatameric form; and the promoter is not a native promoter in *P. fluorescens* but is derived from another organism, such as *E. coli*.

In other embodiments, the protein when produced also includes an additional targeting sequence, for example a sequence that targets the protein to the extracellular medium. In one embodiment, the additional targeting sequence is operably linked to the carboxy-terminus of the protein. In another embodiment, the protein includes a secretion signal for an autotransporter, a two partner secretion system, a main terminal branch system or a fimbrial usher porin.

EXAMPLES

Example 1

Characterization of Sec-System Secretion Signal Peptides

*Pseudomonas fluorescens* Sec-system secretion signal peptides were characterized by formation and expression of an *E. coli* alkaline phosphatase (phoA) coding sequence-genomic DNA fusions. The identities of six of the expressed fusions were further characterized.

The cleavage site for the signal sequences for the secreted genes identified as PhoA fusions was deduced by comparison to homologous proteins from other Pseudomonads, by the SPScan program (Menne et al (2000) *Bioinformatics* 16: 741-742). The cleavage site of the putative lipoprotein was deduced by comparison to signal peptidase II motifs; signal peptidase II specifically cleaves the signal sequences of lipoproteins. All six of the signal peptides were analyzed using SignalP (a software program for analysis of putative signal peptides; available from the Center for Biological Sequence Analysis of the Technical University of Denmark, at on the internet at www.cbs.dtu.dk/services/SignalP/.) Also see, H Nielson et al. (1997) *Protein Engineering* 10:1-6. In some cases, a supplementary source was used to further characterize the identity of the signal peptide. In the case of pbp, cleavage information was obtained by MALDI-TOF analysis of a processed fusion protein (see Example 5 below) This information is present in Table 6.

TABLE 6

Identities of Sec-System Secretion Signal Peptides

| Identity | Putative Amino Acid Sequence |
|---|---|
| Putative phosphate binding protein | 2-24 (SEQ ID NO: 15) of SEQ ID NO: (4) |
| Putative porin E1 precursor, OprE | 2-21 (SEQ ID NO: 26) of SEQ ID NO: (6) |
| Putative azurin | 2-20 (SEQ ID NO: 43) of SEQ ID NO: (8) |
| Putative Lys-Arg-Orn binding protein | 2-23 (SEQ ID NO: 68) of SEQ ID NO: (10) |
| Putative Fe(III) binding protein | 2-32 (SEQ ID NO: 79) of SEQ ID NO: (12) |
| Putative periplasmic lipoprotein B precursor | 2-17 (SEQ ID NO: 90) of SEQ ID NO: (14) |

Western Analysis of the phoA Fusion Proteins

To analyze whether fusion proteins were produced, Western analysis with antibody to alkaline phosphatase was carried out on cultures separated by centrifugation into a whole-cell fraction (cytoplasm and periplasm) and a cell-free broth fraction. Of five strains for which the site of insertion was determined, four signal sequences (putative azurin, putative phosphate binding protein, putative periplasmic lipoprotein B, putative Fe(III) binding protein) produced a fusion protein of the expected size, and one (putative oprE protein) produced a protein about 40 kD smaller than predicted, and one (putative Lys-Arg-Orn binding protein) produced a protein about 20 kD smaller than predicted. The Western analysis and PhoA activity analysis indicate that the signal sequences transported the heterologous PhoA protein into the periplasm of *P. fluorescens*.

Example 2

Construction, Expression, and Characterization of pbp-scFv Fusion

The putative 24 amino acid signal sequence of phophate binding protein (i.e. including Met1) was fused to the gal2 scFv gene (gal2) to produce SEQ ID NO: 101 and 102 (see table) and tested for secretion to the periplasm and/or to the culture supernatant. The fusions were constructed as described below.

```
Phosphate binding protein secretion leader-gal2-His tag fusion
Nucleic Acid sequence)(SEQ ID NO: 101)
atg aaa ctg aaa cgt ttg atg gcg gca atg act ttt gtc gct gct ggc gtt gcg acc gcc aac gcg gtg gcc gcc cag gtg cag ctg cag gag tcg ggc cca gga ctg gtg aag cct tcg gag acc ctg tcc ctc acc tgc act gtc tct ggt ggt tcc atc agt agt tat cac tgg agc tgg atc cgg cag ccc cca ggg aag gga ctg gag tgg att ggg tat atc tat tac agt ggg agc acc aac tac aac ccc tcc ctc aag aat cga gtc acc ata tct gta gac acg tcc aag aac cag ttc tcc ctg aac ctg agg tct gtg acc gct gca gac acg gcc gtg tat tac tgt gcg cga gga acg tat ggc cca gcc gga gat gct ttt gat atc tgg ggg caa ggg acc acg gtc acc gtc tcg agt ggt gga ggc ggt tca ggc gga ggt ggc agc ggc ggt ggc gga tcg gac atc cag atg acc cag tct cct tcc acc ctg tct gca tct att gga gac aga gtc acc atc acc tgc cgg gcc agt gag ggt att tat cac tgg ttg gcc tgg tat cag cag aag cca ggg aaa gcc cct aaa ctc ctg atc tat aag gcc tct agt tta gcc agt ggg gcc cca tca agg ttc agc ggc agt gga tct ggg aca gat ttc act ctc acc atc agc agc ctg cag cct gat gat ttt gca act tat tac tgc caa caa tat agt aat tat ccg ctc act ttc ggc gga ggg acc aag ctg gag atc aaa cgt gcg gcc gca cat cac cat cat cac cat taa Amino Acid sequence)(SEQ ID NO: 102)
Met Lys Leu Lys Arg Leu Met Ala Ala Met Thr Phe Val Ala Ala Gly Val Ala Thr Ala Asn Ala Val Ala Ala Gln Val Gln Leu Gln Glu Ser Gly Pro Gly Leu Val Lys Pro Ser Glu Thr Leu Ser Leu Thr Cys Thr Val Ser Gly Gly Ser Ile Ser Ser Tyr His Trp Ser Trp Ile Arg Gln Pro Pro Gly Lys Gly Leu Glu Trp Ile Gly Tyr Ile Tyr Tyr Ser Gly Ser Thr Asn Tyr Asn Pro Ser Leu Lys Asn Arg Val Thr Ile Ser Val Asp Thr Ser Lys Asn Gln Phe Ser Leu Asn Leu Arg Ser Val Thr Ala Ala Asp Thr Ala Val Tyr Tyr Cys Ala Arg Gly Thr Tyr Gly Pro Ala Gly Asp Ala Phe Asp Ile Trp Gly Gln Gly Thr Thr Val Thr Val Ser Ser Gly Gly Gly Gly Ser Gly Gly Gly Gly Ser Gly Gly Gly Gly Ser Asp Ilr Gln Met Thr Gln Ser Pro Ser Thr Leu Ser Ala Ser Ile Gly Asp Arg Val Thr Ile Thr Cys Arg Ala Ser Glu Gly Ile Tyr His Trp Leu Ala Trp Tyr Gln Gln Lys Pro Gly Lys Ala Pro Lys Leu Leu Ile Tyr Lys Ala Ser Ser Leu Ala Ser Gly Ala Pro Ser Arg Phe Ser Gly Ser Gly Ser Gly Thr Asp Phe Thr Leu The Ile Ser Ser Leu Gln Pro Asp Asp Phe Ala Thr Tyr Tyr Cys Gln Gln Tyr Ser Asn Tyr Pro Leu Thr Phe Gly Gly Gly Thr Lys Leu Glu Ile Lys Arg Ala Ala Ala His His His His His His
```

Construction of pbp-scFv vectors: The *P. fluorescens* oprF and phosphate binding protein (pbp) putative signal sequences were fused to portions of the Gal2 coding sequence at the +2 position using splicing by overlap extension (SOE) PCR. PCR was performed using primers sig_pbp_for (gctctagagg aggtaactta tgaaactgaa acg; SEQ ID NO: 103) and pbp_gal2SOE_rev (ctgcacctgg gcggccaccg cgtt; SEQ ID NO: 104) (including a reverse complement of pbp_gal2SOE_for (aacgcggtgg ccgcccaggt gcag; D SEQ ID NO: 105)), using the *P. fluorescens* pbp secretion signal peptide as template. This resulted in production of an oligonucleotide fragment containing the pbp signal peptide coding sequence and a coding sequence for the 5' end of the gal2 single chain antibody (scAb or scFv).

The gal2 ORF was also amplified. PCR was performed using primers pbp_gal2SOE_for (SEQ ID NO: 105) and scFv2rev (acgcgtcgac ttattaatgg tgatgatggt gatgtgcggc cgcacgtttg atc; SEQ ID NO: 106), and using a gal2-encoding polynucleotide as template. This resulted in production of a polynucleotide fragment containing a coding sequence for the 3' end of the pbp signal peptide and the open reading frame (ORF) of gal2.

The predicted −1 amino acid of the signal sequence (the last amino acid prior to the proposed cleavage site) was fused to the +2 amino acid of the gal2 scFv (Ala). This fusion matched with that of the phosphate binding protein signal peptide in that the amino acid immediately following the recombinant signal peptidase cleavage site (+1) is an Ala, just as is the corresponding amino acid residue in the native pbp protein.

The resulting fusion was cloned into the *P. fluorescens* vector pMYC1803 under control of the Ptac promoter to produce plasmid pDOW1123 (pbp:gal2). The plasmid was transformed into *P. fluorescens* strain MB101 carrying plasmid pCN51-lacI (including a lac repressor), resulting in strain DC217. The plasmid was also transformed into *E. coli* strain JM109.

Construction of scFv clones for secretion in *E. coli*: The gal2 ORF was ligated into pET27b(+) such that the pelB signal sequence is fused to the alanine residue at the +2 position of Gal2. The correct clones were transformed into BL21(DE3)Gold (Stratagene) for expression analysis.

Secretion of Gal2 scFv in *P. fluorescens* vs. *E. coli*.: As described above, the pelB secretion signal for *E. coli* expression/secretion, along with two putative *P. fluorescens* secretion signals were fused to the gal2 open reading frame at the +2 position, i.e., the N-terminal methionine of Gal2 was removed in the fusion and replaced with the indicated signal sequence (FIG. 2). Outer membrane porin F (oprF) and phosphate binding protein (pbp) signal sequences were tested for the ability to secrete a heterologous protein to the periplasm and/or to the culture medium. Both the oprF and pbp leader sequence constructs were found to be expressed and processed in *P. fluorescens* at the 20 L scale. Both constructs produced ~9-10 g/L of protein, most of which was found in the insoluble fraction (FIG. 3B). Approximately 50% of the oprF signal sequence was processed, whereas ~100% of the pbp signal was processed (FIGS. 3A and 3B).

Figure 4:
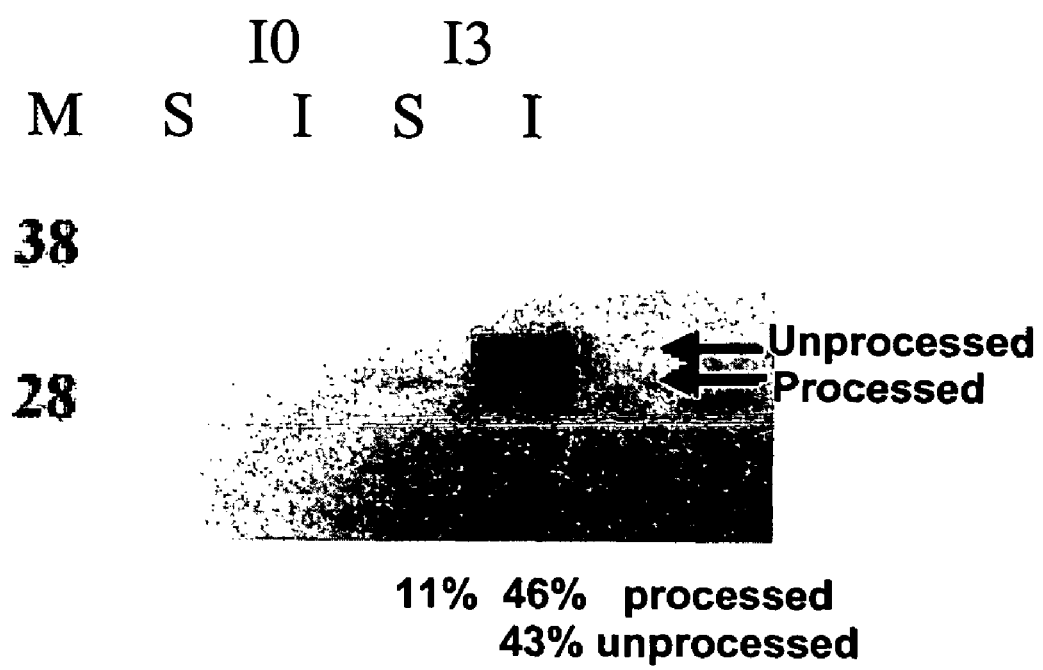
FIG. 4: Expression of pelB:gal2 in *E. coli*. Shown is a picture of a western blot analysis of Gal2 expressed in the pelB:gal2 (pDOW1138). Arrows point to processed and unprocessed protein in the insoluble (I) and soluble (S) fractions. Samples taken at 0 (I0) and 3 hours (I3) post induction were normalized to A575=1; 5 ul were loaded on a 4-12% NuPAGE gel and run in 1×MES buffer.

Moreover, a small amount (<1%) of the processed Gal2 from the pbp:gal2 fusion appears to have been secreted to the culture medium (FIG. 3B). Like the oprF signal sequence, the pelB signal sequence does appear to be processed (FIG. 4). The pelB-gal2 fusion expressed in *E. coli* produced ~1.6 g/L of protein with ~54% processed. Of that, 11% was found in the soluble fraction. Although a greater percentage of the total protein was found in the soluble fraction for the *E. coli* construct, as compared to the *P. fluorescens* pbp:gal2 construct, the overall yield in *P. fluorescens* of processed protein was significantly higher.

TABLE 7

Secreted Gal2 fermentation summary (*compared to BSA standards)

|  | E. coli | P. fluorescens | Pf/Ec |
|---|---|---|---|
| Fermentation time (hr) | 8-9 | 50-70 | 8 |
| Max Gal2 titre (*g/L) | 1.6 (0.8 processed) | 9.3 (25% cv) | 6 (12) |
| Dry biomass (g/L) | 18 | (70) | 4 |
| Gal2/biomass (% w/w) | 8.9 (4.4 processed) | 13 | 1.5 (3) |

Figure 5:
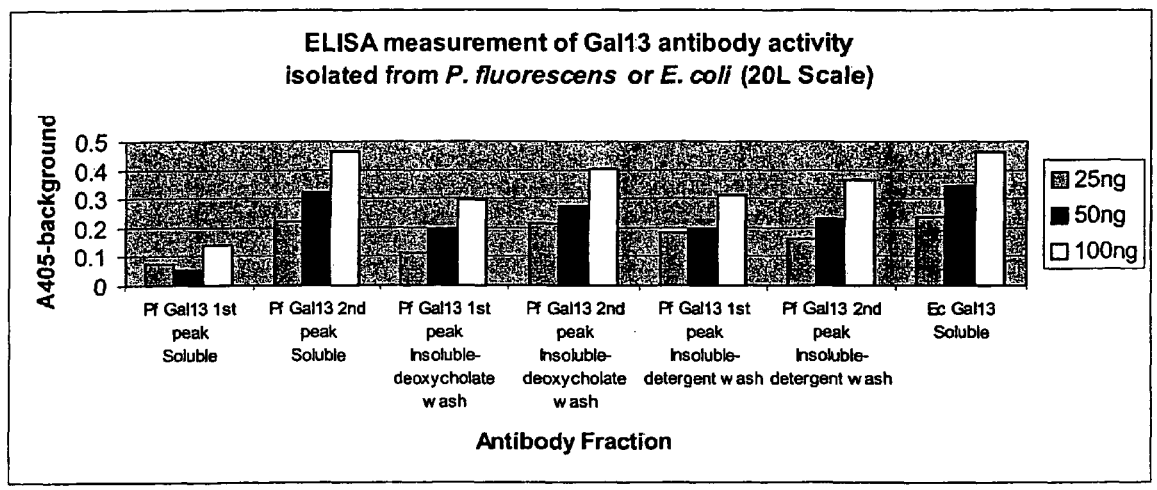
FIG. 5: Activity of purified scFv from *E. coli* and *P. fluorescens*. An ELISA assay (A) used to measure activity of scFv isolated from small scale (B) or large scale (C) fermentations. Activity is expressed as absorbance; the antibody and amount are listed below each bar. An average of three wells is shown.

Analysis of scFv activity: An enzyme linked immunoassay (ELISA) was developed to measure the activity of purified Gal13 and Gal2 anti-β-galactosidase scFv. Varying amounts of purified scFv were added to microplate wells coated with β-galactosidase. Bound antibody was detected using an anti-His tag antibody and an anti-mouse antibody conjugated to alkaline phosphatase (FIG. 5A). A rabbit polyclonal antibody against β-galactosidase was used as a positive control. As illustrated in FIG. 6B Gal2 antibody, purified from small-scale expression experiments, showed significant activity. These results show isolated, renaturable active antibody from inclusion bodies (Gal2).

Example 3

Secretion of Anti-Digoxin scFv in *E. coli* vs *P. fluorescens*

Figure 8:
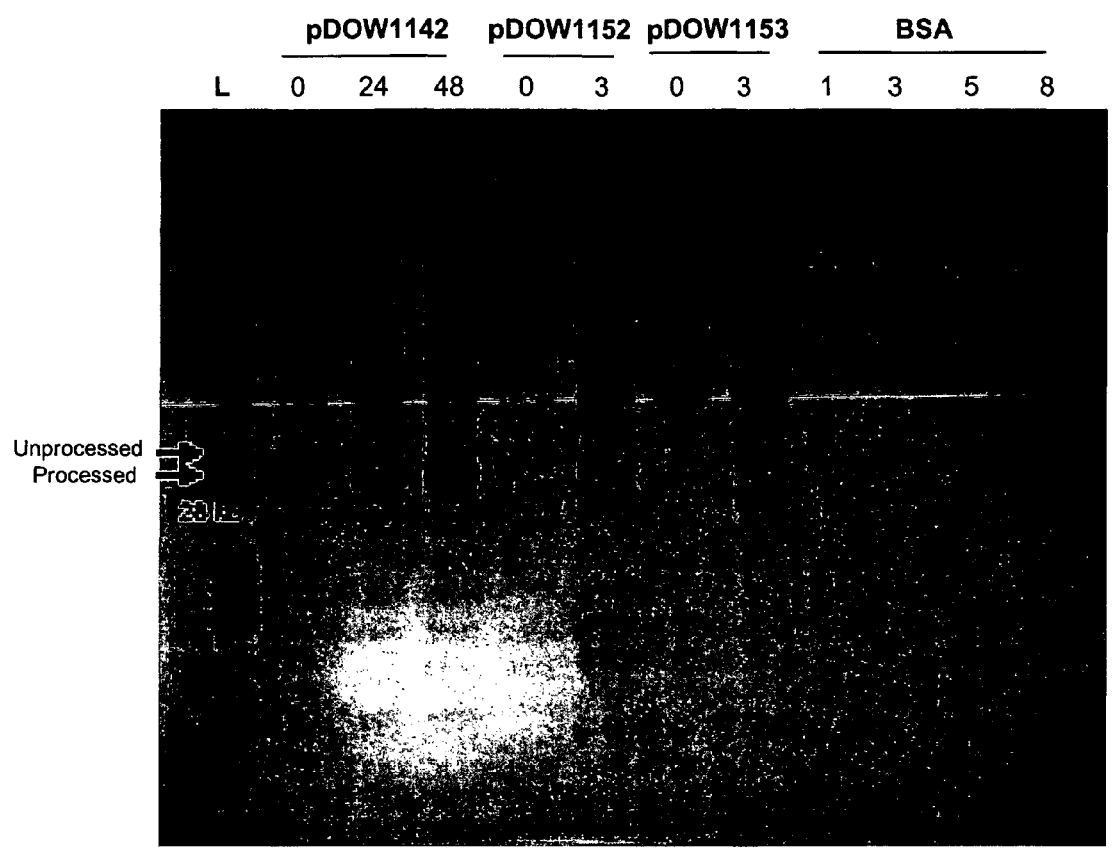
FIG. 8: Comparison of yield between constructs by quantitation of anti-digoxin scFv. 10 uL of each sample (including BSA standards) was loaded onto a 4-12% BT gel and run in 1×MES Buffer. Samples from 0, 3, 24, 48 hours post induction for each construct were loaded. The *P. fluorescens* secreted construct pDOW1142 and the *E. coli* cytoplasmic (pDOW1152) and secreted (pDOW1153) constructs were examined. Arrows indicate the migration of processed and unprocessed secreted scFv. The BSA standard curve is run as follows: 1, 0.1 ug; 3, 0.60 ug; 5, 1.529 ug; 8. 1.85 ug.

Anti-digoxin scFv was cloned into the pET27d vector for secreted expression in *E. coli*. The anti-digoxin scFv was translationally fused to the pelB leader, resulting in pDOW1153. In *P. fluorescens*, the anti-digoxin scFv was translationally fused to the phosphate binding protein secretion signal sequence, resulting in pDOW1142. SDS-PAGE (FIG. 6) and Western analysis (FIG. 7) show that the anti-digoxin scFv expressed in both *P. fluorescens* and *E. coli* is insoluble. The *E. coli* clone produced 60 ug/ml of protein after a 3 hour induction and the pelB secretion leader did not appear to be processed. The *P. fluorescens* clone pDOW1142 produced ~20× more protein than pDOW1153, with 1.23 mg/ml protein expressed as determined by densitometry of an SDS-PAGE when compared to BSA standards (FIG. 8). Expression of anti-digoxin scFv by *P. fluorescens* carrying pDOW1142 was found to be ~15-20 g/L as determined by densitometry at the 20 L scale (data not shown). As observed at the shake flask scale, all protein appeared to be properly processed.

Figure 9:
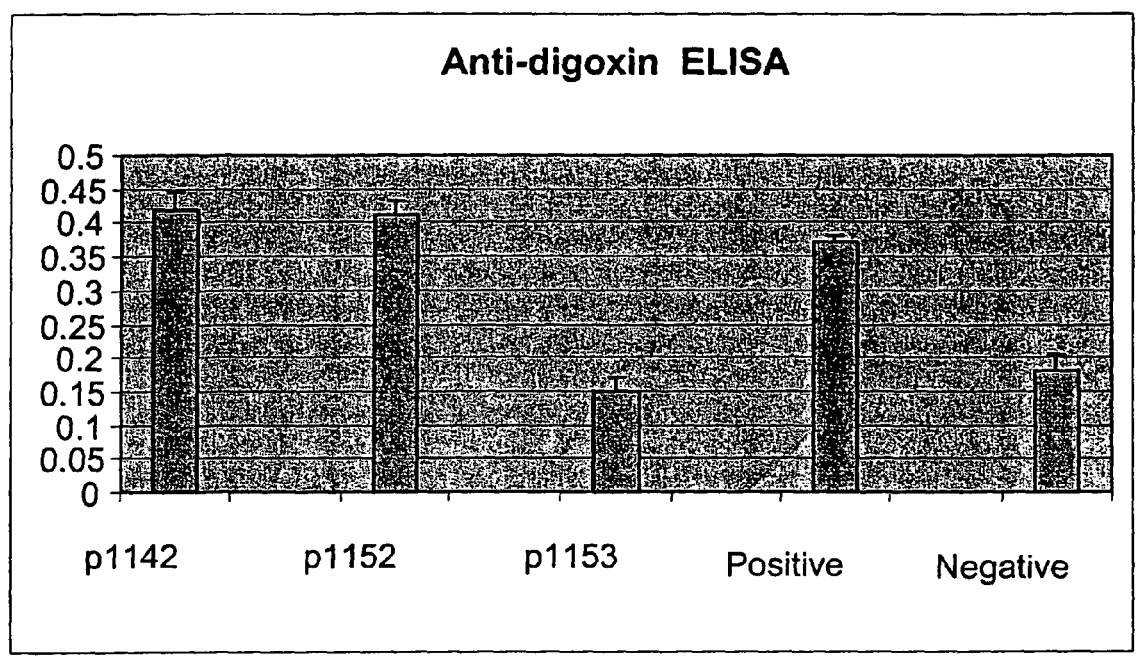
FIG. 9: Activity assay of purified of anti-digoxin scFv. On the X-axis are samples tested: purified scFv from strains containing pDOW1142, pDOW1152 or pDOW1153; polyclonal anti-digoxin antibody (positive); or no protein (negative). On the Y-axis are absorbance values. Error bars represent standard deviation of triplicate samples.
Figure 10:
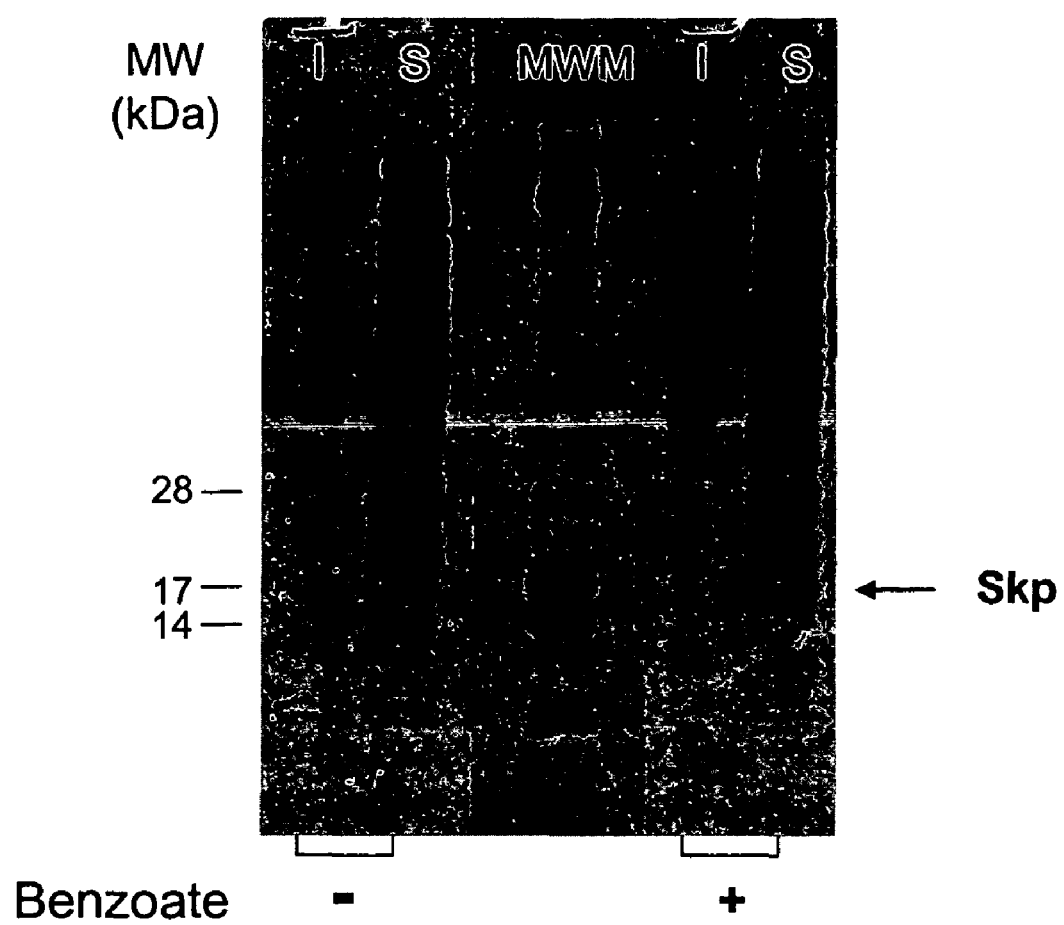
FIG. 10: The Skp protein was induced after 24 hours of growth with 5 mM benzoate. An uninduced flask was used as a control. Cells were harvested 12 hours post induction and the proteins were separated into soluble and insoluble fractions. The proteins were separated on a 4-12% NuPAGE gel (Invitrogen, Carlsbad, Calif.) using MES buffer. Abbreviations are as follows: I, insoluble; S, soluble; MW, molecular weight; MWM, molecular weight marker.

Analysis of purified anti-digoxin scFv activity. Anti-digoxin scFv was purified from both *P. fluorescens* and *E. coli* constructs. Activity was assessed using enzyme-linked immunosorbant assay (ELISA) assay. As shown in FIG. 9, the anti-digoxin scFv isolated from *P. fluorescens* carrying the secreted construct pDOW1142 was found to be active as was the polyclonal antibody control. However, while the *E. coli* cytoplasmic construct pDOW1152 was found to contain active anti-digoxin scFv, the protein purified from *E. coli* carrying the secreted anti-digoxin scFv construct pDOW1153 was found to be inactive and largely unprocessed (FIG. 10).

The results show that *P. fluorescens* produced 19× more protein than the *E. coli* secreted constructs. Moreover, it appeared that the pelB secretion signal used in the *E. coli* construct was not as efficiently processed as was the phosphate binding protein secretion signal in *P. fluorescens*. The protein was almost exclusively insoluble in both *P. fluorescens* and *E. coli*. Nevertheless, the purified *P. fluorescens* secreted protein, along with the purified *E. coli* cytoplasmic protein, were found to be active.

Example 4

MALDI-TOF Analysis for Characterization of pbp:gal2

Matrix-assisted laser desorption/ionization time-of-flight (MALDI-TOF) mass spectrometry analysis was used to characterize the amino acid composition of the secreted mature protein pbp:gal2 to verify that the putative signal peptidase cleavage had occurred at the putative signal peptidase cleavage site for the pbp signal peptide. For this analysis, peptide mass fingerprints were obtained for pbp:gal2 and these data were compared to theoretical peptide mass fingerprints of the deduced amino acid sequences. To generate these peptide mass fingerprints, the protein was digested with endoproteinase Lys-C and the masses of the resulting peptides were determined. N-terminal peptide sequence was determined by post-source-decay (MALDI-PSD). Peptide masses corresponding to unprocessed protein were not observed. The results were as predicted (data not shown).

Example 5

Construction, Expression, and Characterization of a pbp-hGH Fusion

The *P. fluorescens* phosphate binding protein secretion leader was fused to the N-terminus of the mature domain of the human growth hormone (hGH) gene and tested for secretion to the periplasm.

The pbp signal-sequence coding region was PCR amplified from a clone of the *P. fluorescens* pbp signal sequence as template, using sig_pbp_for (SEQ ID NO: 103) and pbp_hgh (gggaatggtt gggaaggcca ccgcgttggc; SEQ ID NO: 107) primers, then gel-purified. This resulted in production of an oligonucleotide fragment containing the pbp signal peptide coding sequence and the coding sequence for the 5' end of the mature domain of hGH.

A cDNA encoding the human growth hormone was PCR-amplified from a human pituitary cDNA library (Clontech, Palo Alto Calif.) using primers ELVIfor (agagaactag taaaaaggag aaatccatgg ctacaggctc ccggacgtcc; SEQ ID NO: 108) and ELVIrev (agagactcga gtcattagaa gccacagctg ccctccac; SEQ ID NO: 109), which were designed to amplify only the mature domain of hGH, and cloned into pMYC1803/SpeI XhoI, forming pDOW2400. The mature hGH gene was amplified from pDOW2400, using primers pbp_hgh_revcomp (gccaacgcgg tggccttccc aaccattccc; SEQ ID NO: 110) and hgh_rev (agagactcga gtcattagaa gccacagctg ccctccacag agcggcac; SEQ ID NO: 111), then purified with Strataprep columns (Stratagene) to remove primers and other reaction components. To make the polynucleotide encoding the pbp-hGH fusion, the two PCR reactions were combined and amplified again with sig_pbp_for (SEQ ID NO: 103) and hgh_rev (SEQ ID NO: 111) in order to link the two pieces. The fragment was ligated to pDOW1269 to form pDOW1323-10, placing pbp-hGH under control of the tac promoter. The ligation mix was transformed into *P. fluorescens*. The DNA and amino acid sequence of this fusion is presented in (SEQ ID NO: 112) and (SEQ ID NO: 113), respectively.

```
Phosphate binding protein secretion leader - human growth hormone fusion
Nucleic acid sequence)(SEQ ID NO: 112)
atg aaa ctg aaa cgt ttg atg gcg gca atg act ttt gtc gct gct ggc gtt gcg acc gcc aac gcg gtg gcc ttc cca acc att ccc tta tcc agg cct ttt gac aac gct atg ctc cgc gcc cat cgt ctg cac cag ctg gcc ttt gac acc tac cag gag ttt gaa gaa gcc tat atc cca aag gaa cag aag tat tca ttc ctg cag aac ccc cag acc tcc ctc tgt ttc tca gag tct att ccg aca ccc tcc aac agg gag gaa aca caa cag aaa tcc aac cta gag ctg ctc cgc atc tcc ctg ctg ctc atc cag tcg tgg ctg gag ccc gtg cag ttc ctc agg agt gtc ttc gcc aac agc ctg gtg tac ggc gcc tct gac agc aac gtc tat gac ctc cta aag gac cta gag gaa ggc atc caa acg ctg atg ggg agg ctg gaa gat ggc agc ccc cgg act ggg cag atc ttc aag cag acc tac agc aag ttc gac aca aac tca cac aac gat gac gca cta ctc aag aac tac ggg ctg ctc tac tgc ttc agg aag gac atg gac aag gtc gag aca ttc ctg cgc atc gtg cag tgc cgc tct gtg gag ggc agc tgt ggc ttc taa Amino acid sequence)(SEQ ID NO: 113)
Met Lys Leu Lys Arg Leu Met Ala Ala Met Thr Phe Val Ala Ala Gly Val Ala Thr Ala Asn Ala Val Ala Phe Pro Thr Ile Pro Leu Ser Arg Pro Phe Asp Asn Ala Met Leu Arg Ala His Arg Leu His Gln Leu Ala Phe Asp Thr Tyr Gln Glu Phe Glu Glu Ala Tyr Ile Pro Lys Glu Gln Lys Tyr Ser Phe Leu Gln Asn Pro Gln Thr Ser Leu Cys Phe Ser Glu Ser Ile Pro Thr Pro Ser Asn Arg Glu Glu Thr Gln Gln Lys Ser Asn
```

Leu Glu Leu Leu Arg Ile Ser Leu Leu Leu Ile Gln Ser Trp Leu Glu Pro Val Gln Phe Leu Arg Ser Val

Phe Ala Asn Ser Leu Val Tyr Gly Ala Ser Asp Ser Asn Val Tyr Asp Leu Leu Lys Asp Leu Glu Glu Gly

Ile Gln Thr Leu Met Gly Arg Leu Glu Asp Gly Ser Pro Arg Thr Gly Gln Ile Phe Lys Gln Thr Tyr Ser

Lys Phe Asp Thr Asn Ser His Asn Asp Asp Ala Leu Leu Lys Asn Tyr Gly Leu Leu Tyr Cys Phe Arg Lys

Asp Met Asp Lys Val Glu Thr Phe Leu Arg Ile Val Gln Cys Arg Ser Val Glu Gly Ser Cys Gly Phe

The resulting strains were tested first at the shake flask scale. Induced bands of the expected size for processed and unprocessed protein (22.2 kDa and 24.5 kDa, respectively) were detected by SDS-PAGE. About half of the protein was processed (indicating localization to the periplasm), and of the processed about half was in the soluble fraction and half in the insoluble fraction (data not shown). Expression studies were scaled up to 20-L bioreactors. Densitometry of the Coomassie-stained SDS-PAGE gels showed that 18% of the total hGH produced was processed and soluble. The strain produced 3.2 g/L of all forms of hGH; processed and soluble hGH was 0.6 g/L.

Example 6

Expression of Skp Chaperone Protein in *P. fluorescens*

The *E. coli* Skp protein with its native leader sequence was expressed in *P. fluorescens* (FIG. 10). After 24 hours of growth, Skp was induced by addition of 5 mM benzoate (the benzoate promoter is described in PCT Publication WO 04/005221). 12 hours post-induction, samples of induced and uninduced proteins were separated into soluble and insoluble fractions by centrifugation at 20,000 g. The proteins were separated on a 4-12% NuPAGE with MES buffer. The *E. coli* Skp protein was observed at a molecular weight of approximately 17 kDa in the induced, soluble sample only (indicated by an arrow in FIG. 10).

The protein was identified as Skp by MALDI post source decay (PSD). Chymotrypsin digests of the excised 17 kDa protein band were prepared. Two chymotrypsin fragments, matching the sizes predicted from theoretical digests of Skp were observed (Table 8). The putative N-terminal peptide with a mass ion at 1378.7 m/z was analyzed further by MALDI-PSD, which revealed the expected N-terminal amino acid sequence of ADKIAIVNMGSLF, (SEQ ID NO: 114) indicating that the leader sequence has been removed as expected, corresponding to the processed site between Ala$^{20}$ and Ala$^{21}$ (FIG. 11).

Example 7

Expression of *P. fluorescens* Signal Sequences in *E. coli*

The signal sequences derived from *P. fluorescens* are functional in *E. coli* allowing the Pbp:Gal2 protein to be processed and secreted to the periplasm.

Figure 12:
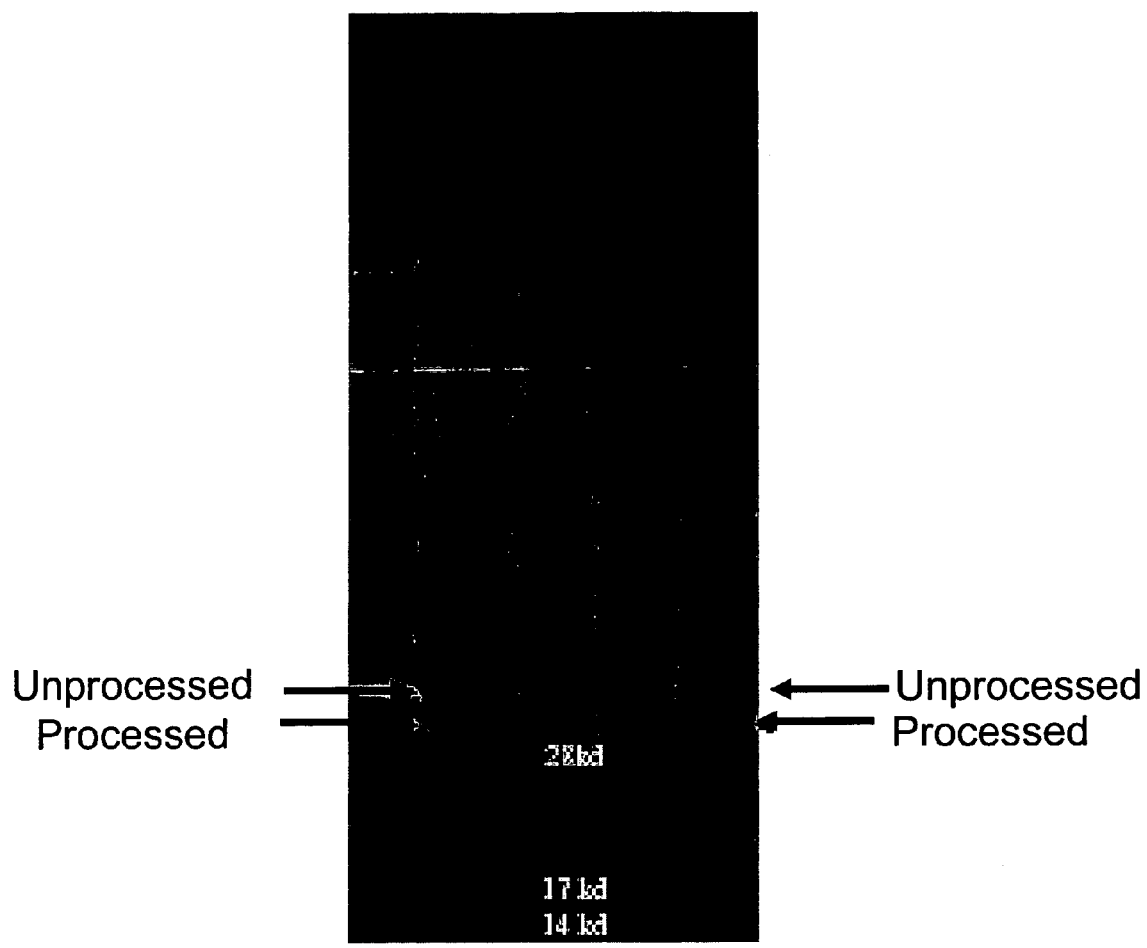
FIG. 12: Image of a SDS-PAGE separation of soluble and insoluble samples comparing JM109 transformed with pDOW1123, grown at 37° C., and induced with 0.01 mM IPTG to the positive control, DC265. Lane 1-soluble DC265, lane 2-insoluble DC265, lane3-SeeBlue Plus 2 ladder, lane 4-soluble JM109/pDOW1123, lane 5-insoluble JM109/pDOW1123. 5 uL of a 20 OD normalized sample was loaded into each well. The 4-12% Bis Tris gel was run at 150 volts in 1×MES buffer for ~50 minutes then stained with Simply Blue Safe Stain.

The *E. coli* strain JM109 (Promega) was transformed with either pDOW1123 (pbp:gal2 fusion) or pDOW1141 (oprF:gal2 fusion). JM109, transformed with pDOW1123, encoding Pbp:gal2, showed expression of the Gal2 protein upon induction with 0.4 mM and 0.01 mM IPTG when grown at 37° C. (FIG. 12). The culture induced with 0.01 mM IPTG exhibited comparable expression to the positive control (DC265,pbp:gal2expressed in *P. fluorescens*).

Figure 13:
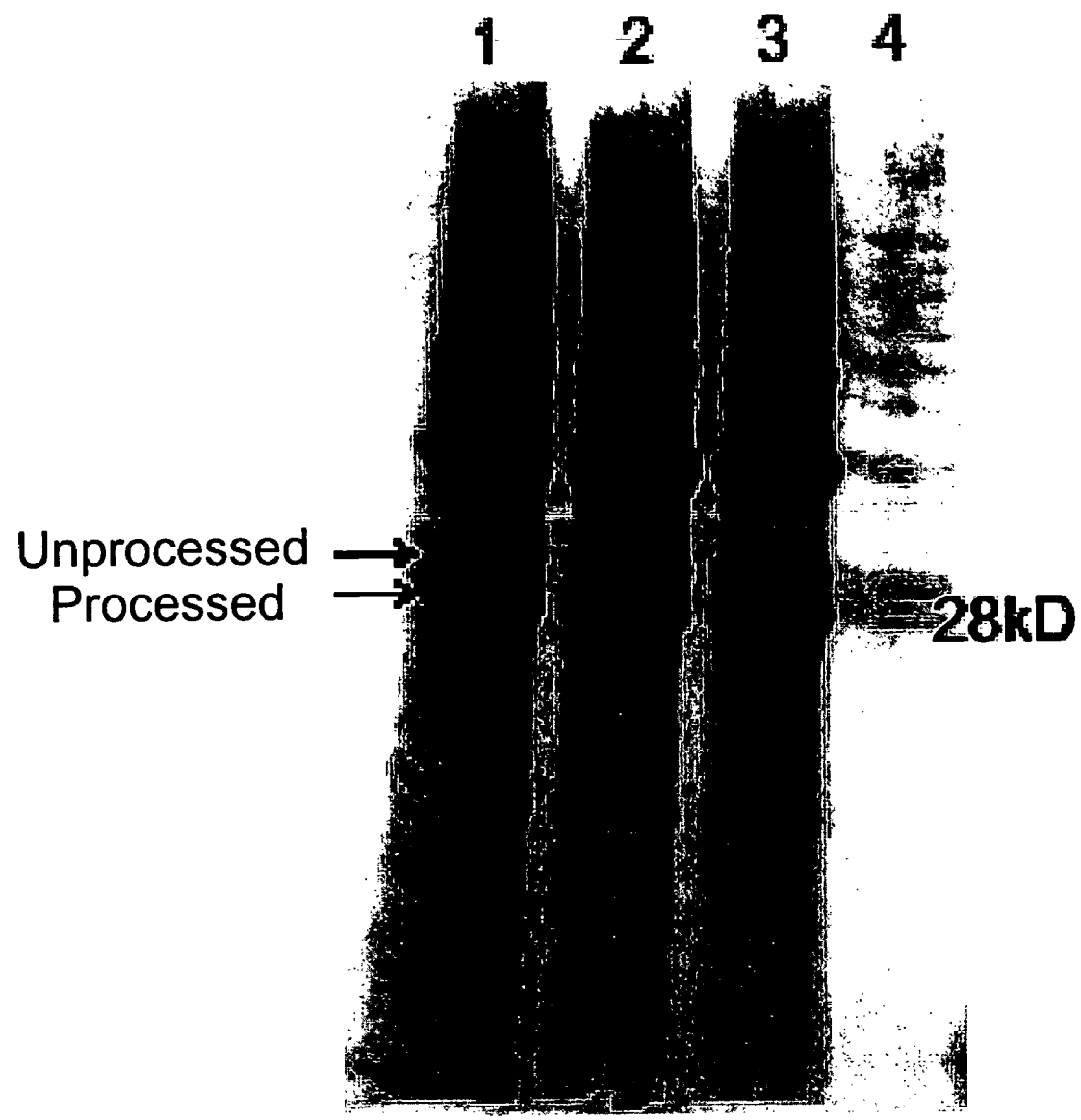
FIG. 13: Image of a SDS-PAGE separation of insoluble samples from the *E. coli* strain JM109 transformed with pDOW1123 and induced with 0.01 mM of IPTG, grown at 37° C. Lanes 1-3, 10 uL of the insoluble sample. Lane 4, 10 uL of 1:20 dilution of the positive control *P. fluorescens* DC265. The 12% Bis-Tris gel was run at 200 volts for ~50 minutes in 1×MES buffer and stained with Novex® Colloidal Blue Stain Kit.
Figure 14:
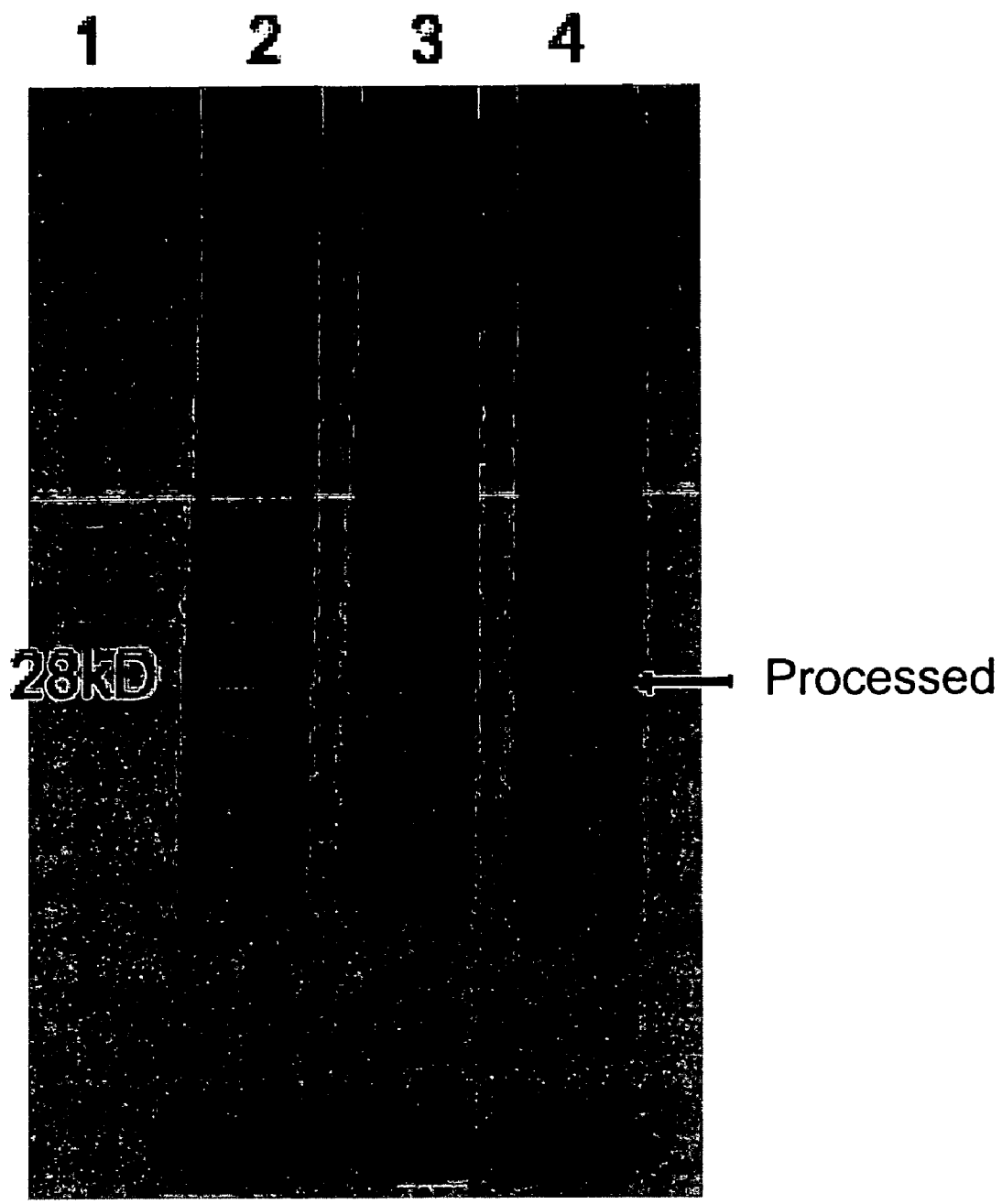
FIG. 14: Image of a SDS-PAGE analysis of the periplasmic samples from the *E. coli* strain JM109 transformed with pDOW1123, induced at 0.01 mM IPTG and grown at 37° C. The 12% Bis-Tris gel was run at 200 V for ~50 minutes in MES buffer and stained with Novex® Colloidal Blue Stain Kit. Lane 1-10 uL of a 1:20 dilution of the DC265 positive control; lanes 2-4 10 uL periplasmic sample.

The two bands seen in the 28 kDa region in FIG. 12 represent Gal2 prior to and post cellular processing (cleavage) of the signal sequence. These two bands were observed in the insoluble fraction by SDS-PAGE, and co-migrated with the processed and unprocessed Gal2 produced by DC245 (FIG. 13). N-terminal sequencing of the respective bands by MALDI-PSD confirmed that the lower band was Gal2 and processed as predicted (FPTIPLSRPF) (SEQ ID NO: 116). The upper band contained sequences of unprocessed Gal2. On an SDS-PAGE gel, the periplasmic sample revealed a band consistent in size to processed Gal2 (FIG. 14).

Figure 15:
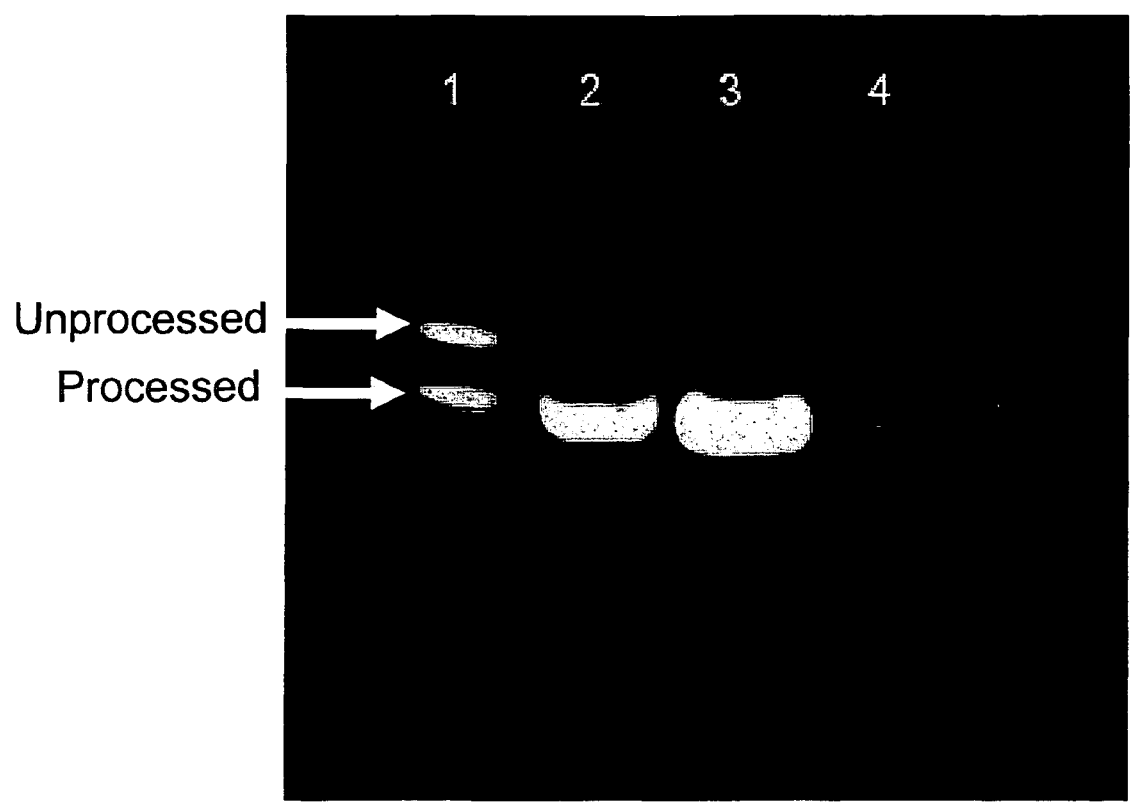
FIG. 15: An image of a western analysis of the soluble, insoluble, and periplasmic fractions of a 0.01 mM IPTG-induced culture of JM109/pDOW1123, grown at 37° C. The samples were run on a 12% Bis Tris gel in MES buffer and transferred to nitrocellulose for 1 hour at 30 volts, then probed with anti-His HRP. Lane 1-10 uL of a 1:30 dilution of the insoluble portion of the positive control. Lane 2-20 uL of the soluble fraction. Lane 3-10 uL of the insoluble fraction. Lane 4-20 uL of the periplasmic preparation.

Western blots were performed on the soluble, insoluble, and periplasmic fractions of the JM109/pDOW1123 sample induced with 0.01 mM IPTG and grown at 37° C. The results showed the processed Gal2 protein was found in all three fractions (FIG. 15).

TABLE 8

Comparison of theoretical and observed chymotrypsin peptide masses for Skp.

| Fragment | Sequence | Theoretical [M + H]$^+$ | Observed [M + H]$^+$ |
|---|---|---|---|
| 1 | ADKIAIVNMGSLF* (SEQ ID NO: 114) | 1378.7 | 1378.9 |
| 2 | QQVAQKTGVSNTLENEF (SEQ ID NO: 115) | 1892.9 | 1893.1 |

*This fragment was further analyzed by MALDI-PSD.

The invention claimed is:

1. An isolated nucleic acid sequence comprising a secretion signal coding sequence for a secretion peptide, wherein the secretion signal coding sequence is operably linked to a nucleotide sequence encoding a recombinant protein or polypeptide of interest, wherein the secretion signal is not native to the recombinant protein or polypeptide of interest, and wherein said secretion signal coding sequence comprises a nucleotide sequence selected from the group consisting of:

a) the phosphate binding protein (pbp) secretion signal set forth in SEQ ID NO: 2;
b) the Outer Membrane Porin E (OprE) secretion signal set forth in SEQ ID NO: 4;
c) the Lys-Arg-Orn binding protein secretion signal set forth in SEQ ID NO: 8;
d) the azurin secretion signal set forth in SEQ ID NO:6
e) the iron (III) binding protein secretion signal set forth in SEQ ID NO: 10;

f) the lipoprotein B secretion signal set forth in SEQ ID NO:12; and, g) a nucleotide sequence encoding an amino acid sequence having at least 90% sequence identity to SEQ ID NO: 1, 3, 7, 5, 9, or 11, wherein said nucleotide sequence encodes a secretion peptide.

2. The nucleic acid of claim 1 wherein the secretion signal coding sequence encodes an amino acid sequence that is at least 90% or at least 95% identical to SEQ ID NO: 1.

3. The nucleic acid of claim 1, wherein said secretion signal coding sequence is adjusted to reflect codon preference of a host organism selected to express the nucleic acid sequence.

4. The nucleic acid of claim 1 wherein the secretion signal coding sequence encodes an amino acid sequence that is at least 90% or at least 95% identical to SEQ ID NO: 3.

5. The nucleic acid of claim 1 wherein the secretion signal coding sequence encodes an amino acid sequence that is at least 90% or at least 95% identical to SEQ ID NO: 5.

6. The nucleic acid of claim 1 wherein the secretion signal coding sequence encodes an amino acid sequence that is at least 90% or at least 95% identical to SEQ ID NO: 7.

7. The nucleic acid of claim 1 wherein the secretion signal coding sequence encodes an amino acid sequence that is at least 90% or at least 95% identical to SEQ ID NO: 9.

8. The nucleic acid of claim 1 wherein the secretion signal coding sequence encodes an amino acid sequence that is at least 90% or at least 95% identical to SEQ ID NO: 11.

9. A recombinant vector comprising a nucleic acid secretion signal sequence coding for a secretion peptide, wherein said secretion signal coding sequence is operably linked to a nucleotide sequence encoding a recombinant protein or polypeptide of interest, wherein the secretion signal is not native to the recombinant protein or polypeptide of interest, and wherein said secretion signal coding sequence comprises a nucleotide sequence selected from the group consisting of:
  a) the pbp secretion signal set forth in SEQ ID NO: 2;
  b) the OprE secretion signal set forth in SEQ ID NO: 4;
  c) the Lys-Arg-Orn binding protein secretion signal set forth in SEQ ID NO: 7;
  d) the azurin secretion signal set forth in SEQ ID NO: 6;
  e) the iron (III) binding protein secretion signal set forth in SEQ ID NO: 10;
  f) the lipoprotein B secretion signal set forth in SEQ ID NO: 12; and,
  g) a nucleotide sequence encoding an amino acid sequence having at least 90% sequence identity to SEQ ID NO: 1, 3, 5, 7, 9 or 11, wherein said nucleotide sequence encodes a secretion peptide.

10. The vector of claim 9 wherein the secretion signal sequence encodes an amino acid sequence having at least 90% sequence identity to SEQ ID NO: 1.

11. The vector of claim 9 comprising a secretion signal sequence that has been adjusted to reflect codon preference of a host organism selected to express the nucleic acid sequence.

12. The vector of claim 9, wherein the secretion signal sequence encodes an amino acid sequence having at least 90% sequence identity to the Outer Membrane Porin E (OprE) secretion signal set forth in SEQ ID NO: 3.

13. The vector of claim 9, wherein the secretion signal sequence encodes an amino acid sequence having at least 90% sequence identity to the Lys-Arg-Orn binding protein secretion signal set forth in SEQ ID NO: 7.

14. The vector of claim 9, wherein the secretion signal sequence encodes an amino acid sequence having at least 90% sequence identity to the azurin secretion signal set forth in SEQ ID NO: 5.

15. The vector of claim 9, wherein the secretion signal sequence encodes an amino acid sequence having at least 90% sequence identity to the iron (III) binding protein secretion signal set forth in SEQ ID NO: 9.

16. The vector of claim 9, wherein the secretion signal sequence encodes an amino acid sequence having at least 90% sequence identity to the lipoprotein B secretion signal set forth in SEQ ID NO: 11.

17. The vector of claim 9 wherein the recombinant protein or polypeptide of interest is native to a host organism selected to express the nucleic acid sequence.

18. The vector of claim 9 wherein the recombinant protein or polypeptide is derived from a protein or polypeptide of interest that is not native to a host organism selected to express the nucleic acid sequence.

19. The vector of claim 9 wherein the recombinant protein or polypeptide of interest is from an organism that is not a Pseudomonad.

20. The vector of claim 9 wherein the recombinant protein or polypeptide of interest is derived from a eukaryotic organism.

21. The vector of claim 9 wherein the recombinant protein or polypeptide of interest is derived from a mammalian organism.

22. The vector of claim 9 further comprising a linkage sequence between the signal peptide sequence and the sequence of the recombinant protein or polypeptide of interest.

23. The vector of claim 22 wherein the linkage sequence is cleavable by a signal peptidase.

24. The vector of claim 9, wherein the vector further comprises a promoter.

25. The vector of claim 24 wherein the promoter is native to a bacterial cell.

26. The vector of claim 24 wherein the promoter is not native to a bacterial cell.

27. The vector of claim 24 wherein the promoter is native to an *E. coli*.

28. The vector of claim 24 wherein the promoter is an inducible promoter.

29. The vector of claim 24 wherein the promoter is a lac promoter or a derivative of a lac promoter.

30. A recombinant cell comprising a nucleic acid secretion signal sequence coding for a secretion peptide, wherein said secretion signal coding sequence is operably linked to a nucleotide sequence encoding a recombinant protein or polypeptide of interest, wherein the secretion signal is not native to the recombinant protein or polypeptide of interest, and wherein said secretion signal coding sequence comprises a nucleotide sequence selected from the group consisting of:
  a) the pbp secretion signal set forth in SEQ ID NO: 2;
  b) the OprE secretion signal set forth in SEQ ID NO: 4;
  c) the Lys-Arg-Orn binding protein secretion signal set forth in SEQ ID NO: 8;
  d) the azurin secretion signal set forth in SEQ ID NO: 6;
  e) the iron (III) binding protein secretion signal set forth in SEQ ID NO: 10;
  f) the lipoprotein B secretion signal set forth in SEQ ID NO: 12; and,
  g) a nucleotide sequence encoding an amino acid sequence, said amino acid sequence having at least 90% sequence identity to SEQ ID NO: 1, 3, 5, 7, 9 or 11, wherein said nucleotide sequence encodes a secretion peptide.

31. The recombinant cell of claim 30 wherein the secretion signal sequence is in an expression vector.

32. The recombinant cell of claim 30 wherein the cell expresses a protein or polypeptide of interest operably linked to a secretion signal peptide encoded by the nucleic acid.

33. The cell of claim 32 wherein the protein or polypeptide of interest is expressed in a periplasmic compartment of the cell.

34. The cell of claim 30 wherein an enzyme in the cell cleaves the signal peptide from the protein or polypeptide of interest.

35. The cell of claim 30 wherein the cell is derived from a bacterial host.

36. The cell of claim 35 wherein the host is a Pseudomonad.

37. The cell of claim 36 wherein the host is a P. fluorescens.

38. The cell of claim 35 wherein the host is an E. coli.

39. An expression system for expression of a recombinant protein or polypeptide of interest comprising:
　a. a host cell; and
　b. a vector comprising a nucleotide sequence encoding a recombinant protein or polypeptide of interest operably linked to a secretion signal coding sequence, wherein the secretion signal coding sequence is not native to the recombinant protein or polypeptide of interest, said secretion signal coding sequence comprising a nucleotide sequence selected from the group consisting of:
　　i) the pbp secretion signal set forth in SEQ ID NO: 2;
　　ii) the OprE secretion signal set forth in SEQ ID NO: 4;
　　iii) the Lys-Arg-Orn binding protein secretion signal set forth in SEQ ID NO: 8;
　　iv) the azurin secretion signal set forth in SEQ ID NO: 6;
　　v) the iron (III) binding protein secretion signal set forth in SEQ ID NO: 10;
　　vi) the lipoprotein B secretion signal set forth in SEQ ID NO: 12; and,
　　vii) a nucleotide sequence encoding an amino acid sequence, said amino acid sequence having at least 90% sequence identity to SEQ ID NO: 1, 3, 5, 7, 9, or 11, wherein said nucleotide sequence encodes a secretion peptide.

40. The expression system of claim 39 wherein the secretion signal coding sequence comprises SEQ ID NO: 2.

41. The expression system of claim 39 wherein the secretion signal coding sequence comprises SEQ ID NO: 4.

42. The expression system of claim 39 wherein the secretion signal coding sequence comprises SEQ ID NO: 6.

43. The expression system of claim 39 wherein the secretion signal coding sequence comprises SEQ ID NO: 8.

44. The expression system of claim 39 wherein the secretion signal coding sequence comprises SEQ ID NO: 10.

45. The expression system of claim 39 wherein the secretion signal coding sequence comprises SEQ ID NO: 12.

46. The expression system of claim 39 wherein the cell expresses a protein or polypeptide of interest operably linked to a secretion signal peptide encoded by the nucleic acid.

47. The expression system of claim 46 wherein the protein or polypeptide is expressed in a periplasmic compartment of the cell.

48. The expression system of claim 46 wherein an enzyme in the cell cleaves the signal peptide from the protein or polypeptide of interest.

49. The expression system of claim 39 wherein the cell is derived from a bacterial host.

50. The expression system of claim 49 wherein the host is a Pseudomonad.

51. The expression system of claim 50 wherein the host is a P. fluorescens.

52. The expression system of claim 49 wherein the host is an E. coli.

53. The expression system of claim 39 further comprising a fermentation medium.

54. The expression system of claim 53 wherein the fermentation medium comprises a chemical inducer.

55. A process for expression of a recombinant protein or polypeptide of interest in a host cell comprising providing a cell, said cell comprising a vector comprising a nucleotide sequence encoding a recombinant protein or polypeptide of interest operably linked to a secretion signal coding sequence, wherein the secretion signal is not native to the recombinant protein or polypeptide of interest, and wherein said secretion signal coding sequence comprises a nucleotide sequence selected from the group consisting of:
　a) the pbp secretion signal set forth in SEQ ID NO: 2;
　b) the OprE secretion signal set forth in SEQ ID NO: 4;
　c) the Lys-Arg-Orn binding protein secretion signal set forth in SEQ ID NO: 8;
　d) the azurin secretion signal set forth in SEQ ID NO: 6;
　e) the iron (III) binding protein secretion signal set forth in SEQ ID NO: 10;
　f) the lipoprotein B secretion signal set forth in SEQ ID NO: 12; and,
　g) a nucleotide sequence encoding an amino acid sequence, said amino acid sequence having at least 90% sequence identity to SEQ ID NO: 1, 3, 5, 7, 9 or 11, wherein said nucleotide sequence encodes a secretion peptide;
and growing the cell under conditions that produce expression of the recombinant protein or polypeptide of interest.

56. The process of claim 55 wherein the secretion signal coding sequence comprises SEQ ID NO: 2.

57. The process of claim 55 wherein the secretion signal coding sequence comprises SEQ ID NO: 4.

58. The process of claim 55 wherein the secretion signal coding sequence comprises SEQ ID NO: 6.

59. The process of claim 55 wherein the secretion signal coding sequence comprises SEQ ID NO: 8.

60. The process of claim 55 wherein the secretion signal coding sequence comprises SEQ ID NO: 10.

61. The process of claim 55 wherein the secretion signal coding sequence comprises SEQ ID NO: 12.

62. The process of claim 55 wherein the cell is grown in a mineral salts medium.

63. The process of claim 55 wherein the cell is grown at a high cell density.

64. The process of claim 63 wherein the cell is grown at a cell density of at least 20 g/L.

65. The process of claim 55 additionally comprising purifying the recombinant protein or polypeptide of interest.

66. The process of claim 55 wherein the recombinant protein or polypeptide of interest is purified by affinity chromatography.

67. The process of claim 55 wherein the operable linkage of the recombinant protein or polypeptide of interest and the secretion signal is cleavable by an enzyme native to the host cell.

68. The process of claim 67 wherein the secretion signal is cleaved from the recombinant protein or polypeptide of interest during expression.

69. The process of claim 55 wherein the recombinant protein or polypeptide of interest is derived from a protein or polypeptide that is native to a host organism.

70. The process of claim 55 wherein the recombinant protein or polypeptide of interest is derived from a protein or polypeptide that is native to a P. fluorescens organism.

71. The process of claim 55 wherein the recombinant protein or polypeptide of interest is derived from a protein or polypeptide that is not native to a host organism.

72. The process of claim 55 wherein the recombinant protein or polypeptide of interest is from an organism that is not a Pseudomonad.

73. The process of claim 55 wherein the recombinant protein or polypeptide of interest is derived from a eukaryotic organism.

74. The process of claim 55 wherein the recombinant protein or polypeptide of interest comprises a sequence that includes at least two cysteine residues.

75. The process of claim 55 wherein at least one disulfide bond is formed in the recombinant protein or polypeptide of interest in the cell.

76. The process of claim 55 further comprising a linkage sequence between the signal peptide sequence and the sequence of the recombinant protein or polypeptide of interest.

77. The process of claim 55 wherein at least 50%, at least 80%, or at least 90% of the recombinant protein or polypeptide of interest comprises a native amino terminus.

78. The process of claim 55 wherein at least 50% or at least 80% of the recombinant protein or polypeptide of interest is active.

79. The process of claim 55 wherein at least 50%, at least 75%, or at least 90% of the recombinant protein or polypeptide of interest is expressed in a periplasmic compartment.

80. The process of claim 55 wherein the cell is a Pseudomonad cell.

81. The process of claim 80 wherein the cell is a *P. fluorescens* cell.

82. The process of claim 55 wherein the cell is an *E. coli* cell.

83. A process for improved expression of a recombinant protein in a *P. fluorescens* host cell comprising providing a *P. fluorescens* host cell comprising a recombinant vector, said recombinant vector comprising a nucleotide acid secretion signal sequence coding for a secretion peptide, wherein said secretion signal coding sequence is operably linked to a nucleotide sequence encoding a recombinant protein or polypeptide of interest, wherein the secretion signal is not native to the recombinant protein or polypeptide of interest, and wherein said secretion signal coding sequence comprises a nucleotide sequence selected from the group consisting of:
   a) the pbp secretion signal set forth in SEQ ID NO: 2;
   b) the OprE secretion signal set forth in SEQ ID NO: 4;
   c) the Lys-Arg-Orn binding protein secretion signal set forth in SEQ ID NO: 8;
   d) the azurin secretion signal set forth in SEQ ID NO: 6;
   e) the iron (III) binding protein secretion signal set forth in SEQ ID NO: 10;
   f) the lipoprotein B secretion signal set forth in SEQ ID NO: 12; and,
   g) a nucleotide sequence encoding an amino acid sequence, said amino acid sequence having at least 90% sequence identity to SEQ ID NO: 1, 3, 5, 7, 9 or 11, wherein said nucleotide sequence encodes a secretion peptide, and;
growing the cell under conditions that produce expression of the recombinant protein or polypeptide of interest.

84. The process of claim 83 wherein the secretion signal coding sequence is from a *P. fluorescense* genome.

85. The process of claim 83 wherein the secretion signal coding sequence is not derived from a *P. fluorescense* genome.

86. The process of claim 83 wherein the secretion signal coding sequence is derived from an *E. coli* genome.

87. The process of claim 83 wherein the host cell is grown in a mineral salts media.

88. The process of claim 83 wherein the host cell is grown at a high cell density.

89. The process of claim 83 wherein the host cell is grown at a cell density of at least 20 g/L.

90. The process of claim 83 additionally comprising purifying the recombinant protein or polypeptide of interest.

91. The process of claim 90 wherein the recombinant protein or polypeptide of interest is purified by affinity chromatography.

92. The process of claim 83 wherein the operable linkage of the recombinant protein or polypeptide of interest and the secretion signal is cleavable by an enzyme native to the host cell.

93. The process of claim 92 wherein the secretion signal is cleaved from the recombinant protein or polypeptide of interest during expression.

* * * * *

UNITED STATES PATENT AND TRADEMARK OFFICE
CERTIFICATE OF CORRECTION

PATENT NO. : 7,985,564 B2
APPLICATION NO. : 10/996007
DATED : July 26, 2011
INVENTOR(S) : Diane M. Retallack et al.

It is certified that error appears in the above-identified patent and that said Letters Patent is hereby corrected as shown below:

On the Title Page:
In the Assignee section (Item 73), please delete "Pfenex, Inc." and replace with --Pfenex Inc.--

In the Specification:
Column 4, line 8, please delete the first "a"

Column 4, line 24, please delete "Pseuomonads" and replace with --Pseudomonads--

Column 10, line 31, please delete "The invention is also the recognition" and replace with --The invention is also based on the recognition--

Column 11, line 35, please delete "protein or a lipoprotein B secretion signal is provided." and replace with --protein, or a lipoprotein B secretion signal, is provided."--

Column 11, line 48, please delete "terminal" and replace with --terminus--

Column 11, line 60, please delete "terminal" and replace with --terminus--

Column 12, line 18, please delete "terminal" and replace with --terminus--

Column 12, line 56, please delete "terminal" and replace with --terminus--

Column 13, line 2, please delete "terminal" and replace with --terminus--

Column 13, line 14, please delete "terminal" and replace with --terminus--

Column 13, line 21, please delete "skp" and replace with --Skp--

Column 14, line 45, please delete "acids" and replace with --acid--

Signed and Sealed this
Twenty-seventh Day of October, 2015

Michelle K. Lee
*Director of the United States Patent and Trademark Office*

CERTIFICATE OF CORRECTION (continued)

U.S. Pat. No. 7,985,564 B2

In the Specification:

Column 14, line 46, please delete "acids" and replace with --acid--

Column 18, line 41, please delete "facilitates" and replace with --facilitate--

Column 21, line 60, please delete "order directly" and replace with --order to directly--

Column 23, line 11, please delete "skp" and replace with --Skp--

Column 23, line 25, please delete "terminal" and replace with --terminus--

Column 27, line 30, please delete "In a embodiment" and replace with --In an embodiment--

Column 34, line 56, please delete ""sah" and replace with --salt--

Column 34, line 57, please delete "Tritriplex" and replace with --Titriplex--

Column 35, line 39, please delete "embodiments" and replace with --embodiment--

Column 38, line 6, please delete "isolated purified" and replace with --isolated and purified--

Column 38, line 18, please delete "fused a ligand" and replace with --fused to a ligand--

Column 38, line 48, please delete "QUIAGEN," and replace with --QIAGEN,--

Column 38, line 59, please delete "from." and replace with --from--

Column 38, line 63, please delete "HCL" and replace with --HCl--

Column 40, line 2, please delete "its"

Column 50, line 26, please delete "FIG. 6B" and replace with --FIG. 5B--

Column 51, line 4, please delete "FIG. 10" and replace with --"FIG. 9"--

UNITED STATES PATENT AND TRADEMARK OFFICE
CERTIFICATE OF CORRECTION

PATENT NO. : 7,985,564 B2
APPLICATION NO. : 10/996007
DATED : July 26, 2011
INVENTOR(S) : Diane M. Retallack, Jane C. Schneider and Thomas Martin Ramseier It is certified that error appears in the above-identified patent and that said Letters Patent is hereby corrected as shown below:

In the Claims

Claim 1:

Column 108, Line 59, "signal set" should read --signal coding sequence set--

Column 108, Line 60, "SEQ ID NO: 2" should read --SEQ ID NO: 3--

Column 108, Line 61, "signal set" should read --signal coding sequence set--

Column 108, Line 62, "SEQ ID NO: 4" should read --SEQ ID NO: 5--

Column 108, Line 63, "signal set" should read --signal coding sequence set--

Column 108, Line 64, "SEQ ID NO: 8" should read --SEQ ID NO: 9--

Column 108, Line 65, "signal set" should read --signal coding sequence set--

Column 108, Line 65, "SEQ ID NO: 6" should read --SEQ ID NO: 7--

Column 108, Line 66, "signal set" should read --signal coding sequence set--

Column 108, Line 67, "SEQ ID NO: 10" should read --SEQ ID NO: 11--

Column 109, Line 1, "signal set" should read --signal coding sequence set--

Column 109, Lines 1-2, "SEQ ID NO:12" should read --SEQ ID NO: 13--

Column 109, Lines 4-5, "SEQ ID NO: 1, 3, 7, 5, 9, or 11" should read --SEQ ID NOs: 4, 6, 10, 8, 12, or 14--

Signed and Sealed this
Eleventh Day of February, 2025

Coke Morgan Stewart
*Acting Director of the United States Patent and Trademark Office*

Claim 2:

Column 109, Line 9, "SEQ ID NO: 1" should read --SEQ ID NO: 4--

Claim 4:

Column 109, Line 15, "SEQ ID NO: 3" should read --SEQ ID NO: 6--

Claim 5:

Column 109, Line 18, "SEQ ID NO: 5" should read --SEQ ID NO: 8--

Claim 6:

Column 109, Line 21, "SEQ ID NO: 7" should read --SEQ ID NO: 10--

Claim 7:

Column 109, Line 25, "SEQ ID NO: 9" should read --SEQ ID NO: 12--

Claim 8:

Column 109, Line 28, "SEQ ID NO: 11" should read --SEQ ID NO: 14--

Claim 9:

Column 109, Line 37, "signal set" should read --signal coding sequence set--

Column 109, Line 37, "SEQ ID NO: 2" should read --SEQ ID NO: 3--

Column 109, Line 38, "signal set" should read --signal coding sequence set--

Column 109, Line 38, "SEQ ID NO: 4" should read --SEQ ID NO: 5--

Column 109, Line 39, "signal set" should read --signal coding sequence set--

Column 109, Line 40, "SEQ ID NO: 7" should read --SEQ ID NO: 9--

Column 109, Line 41, "signal set" should read --signal coding sequence set--

Column 109, Line 41, "SEQ ID NO: 6" should read --SEQ ID NO: 7--

Column 109, Line 42, "signal set" should read --signal coding sequence set--

Column 109, Line 43, "SEQ ID NO: 10" should read --SEQ ID NO: 11--

CERTIFICATE OF CORRECTION (continued)
U.S. Pat. No. 7,985,564 B2

Column 109, Line 44, "signal set" should read --signal coding sequence set--

Column 109, Lines 44-45, "SEQ ID NO: 12" should read --SEQ ID NO: 13--

Column 109, Lines 47-48, "SEQ ID NO: 1, 3, 7, 5, 9, or 11" should read --SEQ ID NOs: 4, 6, 10, 8, 12, or 14--

Claim 10:

Column 109, Line 52, "SEQ ID NO: 1" should read --SEQ ID NO: 4--

Claim 12:

Column 109, Line 59, "SEQ ID NO: 3" should read --SEQ ID NO: 6--

Claim 13:

Column 109, Line 63, "SEQ ID NO: 7" should read --SEQ ID NO: 10--

Claim 14:

Column 109, Line 67, "SEQ ID NO: 5" should read --SEQ ID NO: 8--

Claim 15:

Column 110, Line 4, "SEQ ID NO: 9" should read --SEQ ID NO: 12--

Claim 16:

Column 110, Line 8, "SEQ ID NO: 11" should read --SEQ ID NOs: 14--

Claim 30:

Column 110, Line 53, "signal set" should read --signal coding sequence set--

Column 110, Line 53, "SEQ ID NO: 2" should read --SEQ ID NO: 3--

Column 110, Line 54, "signal set" should read --signal coding sequence set--

Column 110, Line 54, "SEQ ID NO: 4" should read --SEQ ID NO: 5--

Column 110, Line 55, "signal set" should read --signal coding sequence set--

Column 110, Line 56, "SEQ ID NO: 8" should read --SEQ ID NO: 9--

Column 110, Line 57, "signal set" should read --signal coding sequence set--

CERTIFICATE OF CORRECTION (continued)
U.S. Pat. No. 7,985,564 B2

Column 110, Line 57, "SEQ ID NO: 6" should read --SEQ ID NO: 7--

Column 110, Line 58, "signal set" should read --signal coding sequence set--

Column 110, Line 59, "SEQ ID NO: 10" should read --SEQ ID NO: 11--

Column 110, Line 60, "signal set" should read --signal coding sequence set--

Column 110, Lines 60-61, "SEQ ID NO: 12" should read --SEQ ID NO: 13--

Column 110, Line 64, "SEQ ID NO: 1, 3, 7, 5, 9, or 11" should read --SEQ ID NOs: 4, 6, 10, 8, 12, or 14--

Claim 39:

Column 111, Line 27, "signal set" should read --signal coding sequence set--

Column 111, Line 27, "SEQ ID NO: 2" should read --SEQ ID NO: 3--

Column 111, Line 28, "signal set" should read --signal coding sequence set--

Column 111, Line 28, "SEQ ID NO: 4" should read --SEQ ID NO: 5--

Column 111, Line 29, "signal set" should read --signal coding sequence set--

Column 111, Line 30, "SEQ ID NO: 8" should read --SEQ ID NO: 9--

Column 111, Line 31, "signal set" should read --signal coding sequence set--

Column 111, Line 31, "SEQ ID NO: 6" should read --SEQ ID NO: 7--

Column 111, Line 32, "signal set" should read --signal coding sequence set--

Column 111, Line 33, "SEQ ID NO: 10" should read --SEQ ID NO: 11--

Column 111, Line 34, "signal set" should read --signal coding sequence set--

Column 111, Lines 34-35, "SEQ ID NO: 12" should read --SEQ ID NO: 13--

Column 111, Lines 38-39, "SEQ ID NO: 1, 3, 7, 5, 9, or 11" should read --SEQ ID NOs: 4, 6, 10, 8, 12, or 14--

Claim 40:

Column 111, Line 42, "SEQ ID NO: 2" should read --SEQ ID NO: 3--

CERTIFICATE OF CORRECTION (continued)
U.S. Pat. No. 7,985,564 B2

Claim 41:

Column 111, Line 44, "SEQ ID NO: 4" should read --SEQ ID NO: 5--

Claim 42:

Column 111, Line 46, "SEQ ID NO: 6" should read --SEQ ID NO: 7--

Claim 43:

Column 111, Line 48, "SEQ ID NO: 8" should read --SEQ ID NO: 9--

Claim 44:

Column 111, Line 50, "SEQ ID NO: 10" should read --SEQ ID NO: 11--

Claim 45:

Column 111, Line 52, "SEQ ID NO: 12" should read --SEQ ID NO: 13--

Claim 55:

Column 112, Line 17, "signal set" should read --signal coding sequence set--

Column 112, Line 17, "SEQ ID NO: 2" should read --SEQ ID NO: 3--

Column 112, Line 18, "signal set" should read --signal coding sequence set--

Column 112, Line 18, "SEQ ID NO: 4" should read --SEQ ID NO: 5--

Column 112, Line 19, "signal set" should read --signal coding sequence set--

Column 112, Line 20, "SEQ ID NO: 8" should read --SEQ ID NO: 9--

Column 112, Line 21, "signal set" should read --signal coding sequence set--

Column 112, Line 21, "SEQ ID NO: 6" should read --SEQ ID NO: 7--

Column 112, Line 22, "signal set" should read --signal coding sequence set--

Column 112, Line 23, "SEQ ID NO: 10" should read --SEQ ID NO: 11--

Column 112, Line 24, "signal set" should read --signal coding sequence set--

Column 112, Lines 24-25, "SEQ ID NO: 12" should read --SEQ ID NO: 13--

Column 112, Lines 28, "SEQ ID NO: 1, 3, 7, 5, 9, or 11" should read --SEQ ID NOs: 4, 6, 10, 8, 12, or 14--

Claim 56:

Column 112, Line 33, "SEQ ID NO: 2" should read --SEQ ID NO: 3--

Claim 57:

Column 112, Line 35, "SEQ ID NO: 4" should read --SEQ ID NO: 5--

Claim 58:

Column 112, Line 37, "SEQ ID NO: 6" should read --SEQ ID NO: 7--

Claim 59:

Column 112, Line 39, "SEQ ID NO: 8" should read --SEQ ID NO: 9--

Claim 60:

Column 112, Line 41, "SEQ ID NO: 10" should read --SEQ ID NO: 11--

Claim 61:

Column 112, Line 43, "SEQ ID NO: 12" should read --SEQ ID NO: 13--

Claim 83:

Column 114, Line 3, "signal set" should read --signal coding sequence set--

Column 114, Line 3, "SEQ ID NO: 2" should read --SEQ ID NO: 3--

Column 114, Line 4, "signal set" should read --signal coding sequence set--

Column 114, Line 4, "SEQ ID NO: 4" should read --SEQ ID NO: 5--

Column 114, Line 5, "signal set" should read --signal coding sequence set--

Column 114, Line 6, "SEQ ID NO: 8" should read --SEQ ID NO: 9--

Column 114, Line 7, "signal set" should read --signal coding sequence set--

Column 114, Line 7, "SEQ ID NO: 6" should read --SEQ ID NO: 7--

CERTIFICATE OF CORRECTION (continued)
U.S. Pat. No. 7,985,564 B2

Column 114, Line 8, "signal set" should read --signal coding sequence set--

Column 114, Line 9, "SEQ ID NO: 10" should read --SEQ ID NO: 11--

Column 114, Line 10, "signal set" should read --signal coding sequence set--

Column 114, Lines 10-11, "SEQ ID NO: 12" should read --SEQ ID NO: 13--

Column 114, Line 14, "SEQ ID NO: 1, 3, 7, 5, 9, or 11" should read --SEQ ID NOs: 4, 6, 10, 8, 12, or 14--

Claim 84:

Column 114, Line 19, "fluorescense" should read --fluorescens--

Claim 85:

Column 114, Line 21, "fluorescense" should read --fluorescens--

SEQUENCE LISTING

<160> NUMBER OF SEQ ID NOS: 120

<210> SEQ ID NO 1
<211> LENGTH: 20
<212> TYPE: PRT
<213> ORGANISM: Pseudomonas fluorescens

<400> SEQUENCE: 1

```
Asn Thr Leu Gly Leu Ala Ile Gly Ser Leu Ile Ala Ala Thr Ser Phe
1               5                   10                  15

Gly Val Leu Ala
            20
```

<210> SEQ ID NO 2
<211> LENGTH: 22
<212> TYPE: PRT
<213> ORGANISM: Pseudomonas spp.

<400> SEQUENCE: 2

```
Met Arg Pro Ser Ile His Arg Thr Ala Ile Ala Ala Val Leu Ala Thr
1               5                   10                  15

Ala Phe Val Ala Gly Thr
            20
```

<210> SEQ ID NO 3
<211> LENGTH: 72
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(72)

<400> SEQUENCE: 3

```
atg aaa ctg aaa cgt ttg atg gcg gca atg act ttt gtc gct gct ggc    48
Met Lys Leu Lys Arg Leu Met Ala Ala Met Thr Phe Val Ala Ala Gly
1               5                   10                  15 gtt gcg acc gcc aac gcg gtg gcc                                    72
Val Ala Thr Ala Asn Ala Val Ala
            20
```

<210> SEQ ID NO 4
<211> LENGTH: 24
<212> TYPE: PRT
<213> ORGANISM: Artificial Sequence
<220> FEATURE:
<223> OTHER INFORMATION: Synthetic Construct

<400> SEQUENCE: 4

```
Met Lys Leu Lys Arg Leu Met Ala Ala Met Thr Phe Val Ala Ala Gly
1               5                   10                  15

Val Ala Thr Ala Asn Ala Val Ala
            20
```

<210> SEQ ID NO 5
<211> LENGTH: 63
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(63)

```
<400> SEQUENCE: 5 atg aag aag tcc acc ttg gct gtg gct gta acg ttg ggc gca atc gcc       48
Met Lys Lys Ser Thr Leu Ala Val Ala Val Thr Leu Gly Ala Ile Ala
1               5                   10                  15 cag caa gca ggc gct                                                    63
Gln Gln Ala Gly Ala
            20

<210> SEQ ID NO 6
<211> LENGTH: 21
<212> TYPE: PRT
<213> ORGANISM: Artificial Sequence
<220> FEATURE:
<223> OTHER INFORMATION: Synthetic Construct

<400> SEQUENCE: 6

Met Lys Lys Ser Thr Leu Ala Val Ala Val Thr Leu Gly Ala Ile Ala
1               5                   10                  15

Gln Gln Ala Gly Ala
            20

<210> SEQ ID NO 7
<211> LENGTH: 60
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(60)

<400> SEQUENCE: 7 atg ttt gcc aaa ctc gtt gct gtt tcc ctg ctg act ctg gcg agc ggc       48
Met Phe Ala Lys Leu Val Ala Val Ser Leu Leu Thr Leu Ala Ser Gly
1               5                   10                  15 cag ttg ctt gct                                                        60
Gln Leu Leu Ala
            20

<210> SEQ ID NO 8
<211> LENGTH: 20
<212> TYPE: PRT
<213> ORGANISM: Artificial Sequence
<220> FEATURE:
<223> OTHER INFORMATION: Synthetic Construct

<400> SEQUENCE: 8

Met Phe Ala Lys Leu Val Ala Val Ser Leu Leu Thr Leu Ala Ser Gly
1               5                   10                  15

Gln Leu Leu Ala
            20

<210> SEQ ID NO 9
<211> LENGTH: 69
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(69)

<400> SEQUENCE: 9 atg cag aac tat aaa aaa ttc ctt ctg gcc gcg gcc gtc tcg atg gcg       48
Met Gln Asn Tyr Lys Lys Phe Leu Leu Ala Ala Ala Val Ser Met Ala
1               5                   10                  15
```

-continued

```
ttc agc gcc acg gcc atg gca                                              69
Phe Ser Ala Thr Ala Met Ala
            20

<210> SEQ ID NO 10
<211> LENGTH: 23
<212> TYPE: PRT
<213> ORGANISM: Artificial Sequence
<220> FEATURE:
<223> OTHER INFORMATION: Synthetic Construct

<400> SEQUENCE: 10

Met Gln Asn Tyr Lys Lys Phe Leu Leu Ala Ala Ala Val Ser Met Ala
1               5                   10                  15

Phe Ser Ala Thr Ala Met Ala
            20

<210> SEQ ID NO 11
<211> LENGTH: 96
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(96)

<400> SEQUENCE: 11 atg atg atc cgt gac aac cga ctc aag aca tcc ctt ctg cgc ggc ctg     48
Met Met Ile Arg Asp Asn Arg Leu Lys Thr Ser Leu Leu Arg Gly Leu
1               5                   10                  15 acc ctc acc cta ctc agc ctg acc ctg ctc tcg ccc gcg gcc cat tct     96
Thr Leu Thr Leu Leu Ser Leu Thr Leu Leu Ser Pro Ala Ala His Ser
            20                  25                  30

<210> SEQ ID NO 12
<211> LENGTH: 32
<212> TYPE: PRT
<213> ORGANISM: Artificial Sequence
<220> FEATURE:
<223> OTHER INFORMATION: Synthetic Construct

<400> SEQUENCE: 12

Met Met Ile Arg Asp Asn Arg Leu Lys Thr Ser Leu Leu Arg Gly Leu
1               5                   10                  15

Thr Leu Thr Leu Leu Ser Leu Thr Leu Leu Ser Pro Ala Ala His Ser
            20                  25                  30

<210> SEQ ID NO 13
<211> LENGTH: 51
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(51)

<400> SEQUENCE: 13 atg atc aaa cgc aat ctg ctg gtt atg ggc ctt gcc gtg ctg ttg agc     48
Met Ile Lys Arg Asn Leu Leu Val Met Gly Leu Ala Val Leu Leu Ser
1               5                   10                  15 gct                                                                  51
Ala

<210> SEQ ID NO 14
<211> LENGTH: 17
```

```
<212> TYPE: PRT
<213> ORGANISM: Artificial Sequence
<220> FEATURE:
<223> OTHER INFORMATION: Synthetic Construct

<400> SEQUENCE: 14

Met Ile Lys Arg Asn Leu Leu Val Met Gly Leu Ala Val Leu Leu Ser
1               5                   10                  15

Ala

<210> SEQ ID NO 15
<211> LENGTH: 22
<212> TYPE: PRT
<213> ORGANISM: Artificial Sequence
<220> FEATURE:
<223> OTHER INFORMATION: Synthetic

<400> SEQUENCE: 15

Leu Lys Arg Leu Met Ala Ala Met Thr Phe Val Ala Ala Gly Val Ala
1               5                   10                  15

Thr Ala Asn Ala Val Ala
            20

<210> SEQ ID NO 16
<211> LENGTH: 23
<212> TYPE: PRT
<213> ORGANISM: Artificial Sequence
<220> FEATURE:
<223> OTHER INFORMATION: Synthetic

<400> SEQUENCE: 16

Met Lys Leu Lys Arg Leu Met Ala Ala Met Thr Phe Val Ala Ala Gly
1               5                   10                  15

Val Ala Thr Ala Asn Ala Val
            20

<210> SEQ ID NO 17
<211> LENGTH: 22
<212> TYPE: PRT
<213> ORGANISM: Artificial Sequence
<220> FEATURE:
<223> OTHER INFORMATION: Synthetic

<400> SEQUENCE: 17

Met Lys Leu Lys Arg Leu Met Ala Ala Met Thr Phe Val Ala Ala Gly
1               5                   10                  15

Val Ala Thr Ala Asn Ala
            20

<210> SEQ ID NO 18
<211> LENGTH: 21
<212> TYPE: PRT
<213> ORGANISM: Artificial Sequence
<220> FEATURE:
<223> OTHER INFORMATION: Synthetic

<400> SEQUENCE: 18

Met Lys Leu Lys Arg Leu Met Ala Ala Met Thr Phe Val Ala Ala Gly
1               5                   10                  15

Val Ala Thr Ala Asn
            20

<210> SEQ ID NO 19
<211> LENGTH: 20
<212> TYPE: PRT
```

```
<213> ORGANISM: Artificial Sequence
<220> FEATURE:
<223> OTHER INFORMATION: Synthetic

<400> SEQUENCE: 19

Met Lys Leu Lys Arg Leu Met Ala Ala Met Thr Phe Val Ala Ala Gly
1               5                   10                  15

Val Ala Thr Ala
            20

<210> SEQ ID NO 20
<211> LENGTH: 19
<212> TYPE: PRT
<213> ORGANISM: Artificial Sequence
<220> FEATURE:
<223> OTHER INFORMATION: Synthetic

<400> SEQUENCE: 20

Met Lys Leu Lys Arg Leu Met Ala Ala Met Thr Phe Val Ala Ala Gly
1               5                   10                  15

Val Ala Thr

<210> SEQ ID NO 21
<211> LENGTH: 18
<212> TYPE: PRT
<213> ORGANISM: Artificial Sequence
<220> FEATURE:
<223> OTHER INFORMATION: Synthetic

<400> SEQUENCE: 21

Met Lys Leu Lys Arg Leu Met Ala Ala Met Thr Phe Val Ala Ala Gly
1               5                   10                  15

Val Ala

<210> SEQ ID NO 22
<211> LENGTH: 17
<212> TYPE: PRT
<213> ORGANISM: Artificial Sequence
<220> FEATURE:
<223> OTHER INFORMATION: Synthetic

<400> SEQUENCE: 22

Met Lys Leu Lys Arg Leu Met Ala Ala Met Thr Phe Val Ala Ala Gly
1               5                   10                  15

Val

<210> SEQ ID NO 23
<211> LENGTH: 16
<212> TYPE: PRT
<213> ORGANISM: Artificial Sequence
<220> FEATURE:
<223> OTHER INFORMATION: Synthetic

<400> SEQUENCE: 23

Met Lys Leu Lys Arg Leu Met Ala Ala Met Thr Phe Val Ala Ala Gly
1               5                   10                  15

<210> SEQ ID NO 24
<211> LENGTH: 15
<212> TYPE: PRT
<213> ORGANISM: Artificial Sequence
<220> FEATURE:
<223> OTHER INFORMATION: Synthetic

<400> SEQUENCE: 24
```

Met Lys Leu Lys Arg Leu Met Ala Ala Met Thr Phe Val Ala Ala
1               5                   10                  15

<210> SEQ ID NO 25
<211> LENGTH: 14
<212> TYPE: PRT
<213> ORGANISM: Artificial Sequence
<220> FEATURE:
<223> OTHER INFORMATION: Synthetic

<400> SEQUENCE: 25

Met Lys Leu Lys Arg Leu Met Ala Ala Met Thr Phe Val Ala
1               5                   10

<210> SEQ ID NO 26
<211> LENGTH: 19
<212> TYPE: PRT
<213> ORGANISM: Artificial Sequence
<220> FEATURE:
<223> OTHER INFORMATION: Synthetic

<400> SEQUENCE: 26

Lys Ser Thr Leu Ala Val Ala Val Thr Leu Gly Ala Ile Ala Gln Gln
1               5                   10                  15

Ala Gly Ala

<210> SEQ ID NO 27
<211> LENGTH: 20
<212> TYPE: PRT
<213> ORGANISM: Artificial Sequence
<220> FEATURE:
<223> OTHER INFORMATION: Synthetic

<400> SEQUENCE: 27

Met Lys Lys Ser Thr Leu Ala Val Ala Val Thr Leu Gly Ala Ile Ala
1               5                   10                  15

Gln Gln Ala Gly
            20

<210> SEQ ID NO 28
<211> LENGTH: 19
<212> TYPE: PRT
<213> ORGANISM: Artificial Sequence
<220> FEATURE:
<223> OTHER INFORMATION: Synthetic

<400> SEQUENCE: 28

Met Lys Lys Ser Thr Leu Ala Val Ala Val Thr Leu Gly Ala Ile Ala
1               5                   10                  15

Gln Gln Ala

<210> SEQ ID NO 29
<211> LENGTH: 18
<212> TYPE: PRT
<213> ORGANISM: Artificial Sequence
<220> FEATURE:
<223> OTHER INFORMATION: Synthetic

<400> SEQUENCE: 29

Met Lys Lys Ser Thr Leu Ala Val Ala Val Thr Leu Gly Ala Ile Ala
1               5                   10                  15

Gln Gln

<210> SEQ ID NO 30
<211> LENGTH: 17

```
<212> TYPE: PRT
<213> ORGANISM: Artificial Sequence
<220> FEATURE:
<223> OTHER INFORMATION: Synthetic

<400> SEQUENCE: 30

Met Lys Lys Ser Thr Leu Ala Val Ala Val Thr Leu Gly Ala Ile Ala
1               5                   10                  15

Gln

<210> SEQ ID NO 31
<211> LENGTH: 16
<212> TYPE: PRT
<213> ORGANISM: Artificial Sequence
<220> FEATURE:
<223> OTHER INFORMATION: Synthetic

<400> SEQUENCE: 31

Met Lys Lys Ser Thr Leu Ala Val Ala Val Thr Leu Gly Ala Ile Ala
1               5                   10                  15

<210> SEQ ID NO 32
<211> LENGTH: 15
<212> TYPE: PRT
<213> ORGANISM: Artificial Sequence
<220> FEATURE:
<223> OTHER INFORMATION: Synthetic

<400> SEQUENCE: 32

Met Lys Lys Ser Thr Leu Ala Val Ala Val Thr Leu Gly Ala Ile
1               5                   10                  15

<210> SEQ ID NO 33
<211> LENGTH: 14
<212> TYPE: PRT
<213> ORGANISM: Artificial Sequence
<220> FEATURE:
<223> OTHER INFORMATION: Synthetic

<400> SEQUENCE: 33

Met Lys Lys Ser Thr Leu Ala Val Ala Val Thr Leu Gly Ala
1               5                   10

<210> SEQ ID NO 34
<211> LENGTH: 13
<212> TYPE: PRT
<213> ORGANISM: Artificial Sequence
<220> FEATURE:
<223> OTHER INFORMATION: Synthetic

<400> SEQUENCE: 34

Met Lys Lys Ser Thr Leu Ala Val Ala Val Thr Leu Gly
1               5                   10

<210> SEQ ID NO 35
<211> LENGTH: 12
<212> TYPE: PRT
<213> ORGANISM: Artificial Sequence
<220> FEATURE:
<223> OTHER INFORMATION: Synthetic

<400> SEQUENCE: 35

Met Lys Lys Ser Thr Leu Ala Val Ala Val Thr Leu
1               5                   10

<210> SEQ ID NO 36
<211> LENGTH: 11
```

```
<212> TYPE: PRT
<213> ORGANISM: Artificial Sequence
<220> FEATURE:
<223> OTHER INFORMATION: Synthetic

<400> SEQUENCE: 36

Met Lys Lys Ser Thr Leu Ala Val Ala Val Thr
1               5                   10

<210> SEQ ID NO 37
<211> LENGTH: 21
<212> TYPE: PRT
<213> ORGANISM: Artificial Sequence
<220> FEATURE:
<223> OTHER INFORMATION: Synthetic

<400> SEQUENCE: 37

Met Tyr Lys Ser Thr Leu Ala Val Ala Val Thr Leu Gly Ala Ile Ala
1               5                   10                  15

Gln Gln Ala Gly Ala
            20

<210> SEQ ID NO 38
<211> LENGTH: 21
<212> TYPE: PRT
<213> ORGANISM: Artificial Sequence
<220> FEATURE:
<223> OTHER INFORMATION: Synthetic

<400> SEQUENCE: 38

Met Lys Lys Ser Ser Leu Ala Val Ala Val Thr Leu Gly Ala Ile Ala
1               5                   10                  15

Gln Gln Ala Gly Ala
            20

<210> SEQ ID NO 39
<211> LENGTH: 21
<212> TYPE: PRT
<213> ORGANISM: Artificial Sequence
<220> FEATURE:
<223> OTHER INFORMATION: Synthetic

<400> SEQUENCE: 39

Met Lys Lys Ser Thr Leu Ala Leu Ala Val Thr Leu Gly Ala Ile Ala
1               5                   10                  15

Gln Gln Ala Gly Ala
            20

<210> SEQ ID NO 40
<211> LENGTH: 22
<212> TYPE: PRT
<213> ORGANISM: Artificial Sequence
<220> FEATURE:
<223> OTHER INFORMATION: Synthetic

<400> SEQUENCE: 40

Met Lys Lys Ser Thr Leu Ala Val Ala Val Arg Thr Leu Gly Ala Ile
1               5                   10                  15

Ala Gln Gln Ala Gly Ala
            20

<210> SEQ ID NO 41
<211> LENGTH: 21
<212> TYPE: PRT
<213> ORGANISM: Artificial Sequence
<220> FEATURE:
```

<223> OTHER INFORMATION: Synthetic

<400> SEQUENCE: 41

Met Lys Lys Ser Thr Leu Ala Val Ala Val Thr Leu Gly Val Ile Ala
1               5                   10                  15

Gln Gln Ala Gly Ala
            20

<210> SEQ ID NO 42
<211> LENGTH: 21
<212> TYPE: PRT
<213> ORGANISM: Artificial Sequence
<220> FEATURE:
<223> OTHER INFORMATION: Synthetic

<400> SEQUENCE: 42

Met Lys Lys Ser Thr Leu Ala Val Ala Val Thr Leu Gly Ala Leu Ala
1               5                   10                  15

Gln Gln Ala Gly Ala
            20

<210> SEQ ID NO 43
<211> LENGTH: 18
<212> TYPE: PRT
<213> ORGANISM: Artificial Sequence
<220> FEATURE:
<223> OTHER INFORMATION: Synthetic

<400> SEQUENCE: 43

Ala Lys Leu Val Ala Val Ser Leu Leu Thr Leu Ala Ser Gly Gln Leu
1               5                   10                  15

Leu Ala

<210> SEQ ID NO 44
<211> LENGTH: 19
<212> TYPE: PRT
<213> ORGANISM: Artificial Sequence
<220> FEATURE:
<223> OTHER INFORMATION: Synthetic

<400> SEQUENCE: 44

Met Phe Ala Lys Leu Val Ala Val Ser Leu Leu Thr Leu Ala Ser Gly
1               5                   10                  15

Gln Leu Leu

<210> SEQ ID NO 45
<211> LENGTH: 18
<212> TYPE: PRT
<213> ORGANISM: Artificial Sequence
<220> FEATURE:
<223> OTHER INFORMATION: Synthetic

<400> SEQUENCE: 45

Met Phe Ala Lys Leu Val Ala Val Ser Leu Leu Thr Leu Ala Ser Gly
1               5                   10                  15

Gln Leu

<210> SEQ ID NO 46
<211> LENGTH: 17
<212> TYPE: PRT
<213> ORGANISM: Artificial Sequence
<220> FEATURE:
<223> OTHER INFORMATION: Synthetic

<400> SEQUENCE: 46

Met Phe Ala Lys Leu Val Ala Val Ser Leu Leu Thr Leu Ala Ser Gly
1               5                   10                  15

Gln

<210> SEQ ID NO 47
<211> LENGTH: 16
<212> TYPE: PRT
<213> ORGANISM: Artificial Sequence
<220> FEATURE:
<223> OTHER INFORMATION: Synthetic

<400> SEQUENCE: 47

Met Phe Ala Lys Leu Val Ala Val Ser Leu Leu Thr Leu Ala Ser Gly
1               5                   10                  15

<210> SEQ ID NO 48
<211> LENGTH: 15
<212> TYPE: PRT
<213> ORGANISM: Artificial Sequence
<220> FEATURE:
<223> OTHER INFORMATION: Synthetic

<400> SEQUENCE: 48

Met Phe Ala Lys Leu Val Ala Val Ser Leu Leu Thr Leu Ala Ser
1               5                   10                  15

<210> SEQ ID NO 49
<211> LENGTH: 14
<212> TYPE: PRT
<213> ORGANISM: Artificial Sequence
<220> FEATURE:
<223> OTHER INFORMATION: Synthetic

<400> SEQUENCE: 49

Met Phe Ala Lys Leu Val Ala Val Ser Leu Leu Thr Leu Ala
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Synthetic

<400> SEQUENCE: 50

Met Phe Ala Lys Leu Val Ala Val Ser Leu Leu Thr Leu
1               5                   10

<210> SEQ ID NO 51
<211> LENGTH: 12
<212> TYPE: PRT
<213> ORGANISM: Artificial Sequence
<220> FEATURE:
<223> OTHER INFORMATION: Synthetic

<400> SEQUENCE: 51

Met Phe Ala Lys Leu Val Ala Val Ser Leu Leu Thr
1               5                   10

<210> SEQ ID NO 52
<211> LENGTH: 11
<212> TYPE: PRT
<213> ORGANISM: Artificial Sequence
<220> FEATURE:
<223> OTHER INFORMATION: Synthetic

<400> SEQUENCE: 52

Met Phe Ala Lys Leu Val Ala Val Ser Leu Leu
1               5                   10

<210> SEQ ID NO 53
<211> LENGTH: 10
<212> TYPE: PRT
<213> ORGANISM: Artificial Sequence
<220> FEATURE:
<223> OTHER INFORMATION: Synthetic

<400> SEQUENCE: 53

Met Phe Ala Lys Leu Val Ala Val Ser Leu
1               5                   10

<210> SEQ ID NO 54
<211> LENGTH: 20
<212> TYPE: PRT
<213> ORGANISM: Artificial Sequence
<220> FEATURE:
<223> OTHER INFORMATION: Synthetic

<400> SEQUENCE: 54

Met Leu Arg Lys Leu Val Ala Val Ser Leu Leu Thr Leu Ala Ser Gly
1               5                   10                  15

Gln Leu Leu Ala
            20

<210> SEQ ID NO 55
<211> LENGTH: 20
<212> TYPE: PRT
<213> ORGANISM: Artificial Sequence
<220> FEATURE:
<223> OTHER INFORMATION: Synthetic

<400> SEQUENCE: 55

Met Ile Arg Lys Leu Val Ala Val Ser Leu Leu Thr Leu Ala Ser Gly
1               5                   10                  15

Gln Leu Leu Ala
            20

<210> SEQ ID NO 56
<211> LENGTH: 20
<212> TYPE: PRT
<213> ORGANISM: Artificial Sequence
<220> FEATURE:
<223> OTHER INFORMATION: Synthetic

<400> SEQUENCE: 56

Met Phe Ala Lys Ala Val Ala Val Ser Leu Leu Thr Leu Ala Ser Gly
1               5                   10                  15

Gln Leu Leu Ala
            20

<210> SEQ ID NO 57
<211> LENGTH: 20
<212> TYPE: PRT
<213> ORGANISM: Artificial Sequence
<220> FEATURE:
<223> OTHER INFORMATION: Synthetic

<400> SEQUENCE: 57

Met Phe Ala Lys Leu Ala Ala Val Ser Leu Leu Thr Leu Ala Ser Gly
1               5                   10                  15

Gln Leu Leu Ala
            20

```
<210> SEQ ID NO 58
<211> LENGTH: 20
<212> TYPE: PRT
<213> ORGANISM: Artificial Sequence
<220> FEATURE:
<223> OTHER INFORMATION: Synthetic

<400> SEQUENCE: 58

Met Phe Ala Lys Leu Ile Ser Ala Ser Leu Leu Thr Leu Ala Ser Gly
1               5                   10                  15

Gln Leu Leu Ala
            20

<210> SEQ ID NO 59
<211> LENGTH: 20
<212> TYPE: PRT
<213> ORGANISM: Artificial Sequence
<220> FEATURE:
<223> OTHER INFORMATION: Synthetic

<400> SEQUENCE: 59

Met Phe Ala Lys Leu Val Ala Val Ser Leu Ile Thr Leu Ala Ser Gly
1               5                   10                  15

Gln Leu Leu Ala
            20

<210> SEQ ID NO 60
<211> LENGTH: 20
<212> TYPE: PRT
<213> ORGANISM: Artificial Sequence
<220> FEATURE:
<223> OTHER INFORMATION: Synthetic

<400> SEQUENCE: 60

Met Phe Ala Lys Leu Val Ala Val Ser Leu Leu Ser Leu Ala Ser Gly
1               5                   10                  15

Gln Leu Leu Ala
            20

<210> SEQ ID NO 61
<211> LENGTH: 20
<212> TYPE: PRT
<213> ORGANISM: Artificial Sequence
<220> FEATURE:
<223> OTHER INFORMATION: Synthetic

<400> SEQUENCE: 61

Met Phe Ala Lys Leu Val Ala Val Ser Leu Leu Thr Leu Leu Ser Gly
1               5                   10                  15

Gln Leu Leu Ala
            20

<210> SEQ ID NO 62
<211> LENGTH: 20
<212> TYPE: PRT
<213> ORGANISM: Artificial Sequence
<220> FEATURE:
<223> OTHER INFORMATION: Synthetic

<400> SEQUENCE: 62

Met Phe Ala Lys Leu Val Ala Val Ser Leu Leu Thr Leu Phe Ser Gly
1               5                   10                  15

Gln Leu Leu Ala
            20
```

<210> SEQ ID NO 63
<211> LENGTH: 20
<212> TYPE: PRT
<213> ORGANISM: Artificial Sequence
<220> FEATURE:
<223> OTHER INFORMATION: Synthetic

<400> SEQUENCE: 63

Met Phe Ala Lys Leu Val Ala Val Ser Leu Leu Thr Leu Ala Ser Ala
1               5                   10                  15

Gln Leu Leu Ala
            20

<210> SEQ ID NO 64
<211> LENGTH: 20
<212> TYPE: PRT
<213> ORGANISM: Artificial Sequence
<220> FEATURE:
<223> OTHER INFORMATION: Synthetic

<400> SEQUENCE: 64

Met Phe Ala Lys Leu Val Ala Val Ser Leu Leu Thr Leu Ala Ser Gly
1               5                   10                  15

Ser Leu Leu Ala
            20

<210> SEQ ID NO 65
<211> LENGTH: 20
<212> TYPE: PRT
<213> ORGANISM: Artificial Sequence
<220> FEATURE:
<223> OTHER INFORMATION: Synthetic

<400> SEQUENCE: 65

Met Phe Ala Lys Leu Val Ala Val Ser Leu Leu Thr Leu Ala Ser Gly
1               5                   10                  15

Pro Leu Leu Ala
            20

<210> SEQ ID NO 66
<211> LENGTH: 20
<212> TYPE: PRT
<213> ORGANISM: Artificial Sequence
<220> FEATURE:
<223> OTHER INFORMATION: Synthetic

<400> SEQUENCE: 66

Met Phe Ala Lys Leu Val Ala Val Ser Leu Leu Thr Leu Ala Ser Gly
1               5                   10                  15

Gln Val Leu Ala
            20

<210> SEQ ID NO 67
<211> LENGTH: 20
<212> TYPE: PRT
<213> ORGANISM: Artificial Sequence
<220> FEATURE:
<223> OTHER INFORMATION: Synthetic

<400> SEQUENCE: 67

Met Phe Ala Lys Leu Val Ala Val Ser Leu Leu Thr Leu Ala Ser Gly
1               5                   10                  15

Gln Val Phe Ala
            20

```
<210> SEQ ID NO 68
<211> LENGTH: 21
<212> TYPE: PRT
<213> ORGANISM: Artificial Sequence
<220> FEATURE:
<223> OTHER INFORMATION: Synthetic

<400> SEQUENCE: 68

Asn Tyr Lys Lys Phe Leu Leu Ala Ala Ala Val Ser Met Ala Phe Ser
1               5                   10                  15

Ala Thr Ala Met Ala
            20

<210> SEQ ID NO 69
<211> LENGTH: 22
<212> TYPE: PRT
<213> ORGANISM: Artificial Sequence
<220> FEATURE:
<223> OTHER INFORMATION: Synthetic

<400> SEQUENCE: 69

Met Gln Asn Tyr Lys Lys Phe Leu Leu Ala Ala Ala Val Ser Met Ala
1               5                   10                  15

Phe Ser Ala Thr Ala Met
            20

<210> SEQ ID NO 70
<211> LENGTH: 21
<212> TYPE: PRT
<213> ORGANISM: Artificial Sequence
<220> FEATURE:
<223> OTHER INFORMATION: Synthetic

<400> SEQUENCE: 70

Met Gln Asn Tyr Lys Lys Phe Leu Leu Ala Ala Ala Val Ser Met Ala
1               5                   10                  15

Phe Ser Ala Thr Ala
            20

<210> SEQ ID NO 71
<211> LENGTH: 20
<212> TYPE: PRT
<213> ORGANISM: Artificial Sequence
<220> FEATURE:
<223> OTHER INFORMATION: Synthetic

<400> SEQUENCE: 71

Met Gln Asn Tyr Lys Lys Phe Leu Leu Ala Ala Ala Val Ser Met Ala
1               5                   10                  15

Phe Ser Ala Thr
            20

<210> SEQ ID NO 72
<211> LENGTH: 19
<212> TYPE: PRT
<213> ORGANISM: Artificial Sequence
<220> FEATURE:
<223> OTHER INFORMATION: Synthetic

<400> SEQUENCE: 72

Met Gln Asn Tyr Lys Lys Phe Leu Leu Ala Ala Ala Val Ser Met Ala
1               5                   10                  15

Phe Ser Ala
```

<210> SEQ ID NO 73
<211> LENGTH: 18
<212> TYPE: PRT
<213> ORGANISM: Artificial Sequence
<220> FEATURE:
<223> OTHER INFORMATION: Synthetic

<400> SEQUENCE: 73

Met Gln Asn Tyr Lys Lys Phe Leu Leu Ala Ala Ala Val Ser Met Ala
1               5                   10                  15

Phe Ser

<210> SEQ ID NO 74
<211> LENGTH: 17
<212> TYPE: PRT
<213> ORGANISM: Artificial Sequence
<220> FEATURE:
<223> OTHER INFORMATION: Synthetic

<400> SEQUENCE: 74

Met Gln Asn Tyr Lys Lys Phe Leu Leu Ala Ala Ala Val Ser Met Ala
1               5                   10                  15

Phe

<210> SEQ ID NO 75
<211> LENGTH: 16
<212> TYPE: PRT
<213> ORGANISM: Artificial Sequence
<220> FEATURE:
<223> OTHER INFORMATION: Synthetic

<400> SEQUENCE: 75

Met Gln Asn Tyr Lys Lys Phe Leu Leu Ala Ala Ala Val Ser Met Ala
1               5                   10                  15

<210> SEQ ID NO 76
<211> LENGTH: 15
<212> TYPE: PRT
<213> ORGANISM: Artificial Sequence
<220> FEATURE:
<223> OTHER INFORMATION: Synthetic

<400> SEQUENCE: 76

Met Gln Asn Tyr Lys Lys Phe Leu Leu Ala Ala Ala Val Ser Met
1               5                   10                  15

<210> SEQ ID NO 77
<211> LENGTH: 14
<212> TYPE: PRT
<213> ORGANISM: Artificial Sequence
<220> FEATURE:
<223> OTHER INFORMATION: Synthetic

<400> SEQUENCE: 77

Met Gln Asn Tyr Lys Lys Phe Leu Leu Ala Ala Ala Val Ser
1               5                   10

<210> SEQ ID NO 78
<211> LENGTH: 13
<212> TYPE: PRT
<213> ORGANISM: Artificial Sequence
<220> FEATURE:
<223> OTHER INFORMATION: Synthetic

<400> SEQUENCE: 78

Met Gln Asn Tyr Lys Lys Phe Leu Leu Ala Ala Ala Val

```
1               5                   10
```

<210> SEQ ID NO 79
<211> LENGTH: 30
<212> TYPE: PRT
<213> ORGANISM: Artificial Sequence
<220> FEATURE:
<223> OTHER INFORMATION: Synthetic

<400> SEQUENCE: 79

```
Ile Arg Asp Asn Arg Leu Lys Thr Ser Leu Leu Arg Gly Leu Thr Leu
1               5                   10                  15

Thr Leu Leu Ser Leu Thr Leu Leu Ser Pro Ala Ala His Ser
            20                  25                  30
```

<210> SEQ ID NO 80
<211> LENGTH: 31
<212> TYPE: PRT
<213> ORGANISM: Artificial Sequence
<220> FEATURE:
<223> OTHER INFORMATION: Synthetic

<400> SEQUENCE: 80

```
Met Met Ile Arg Asp Asn Arg Leu Lys Thr Ser Leu Leu Arg Gly Leu
1               5                   10                  15

Thr Leu Thr Leu Leu Ser Leu Thr Leu Leu Ser Pro Ala Ala His
            20                  25                  30
```

<210> SEQ ID NO 81
<211> LENGTH: 30
<212> TYPE: PRT
<213> ORGANISM: Artificial Sequence
<220> FEATURE:
<223> OTHER INFORMATION: Synthetic

<400> SEQUENCE: 81

```
Met Met Ile Arg Asp Asn Arg Leu Lys Thr Ser Leu Leu Arg Gly Leu
1               5                   10                  15

Thr Leu Thr Leu Leu Ser Leu Thr Leu Leu Ser Pro Ala Ala
            20                  25                  30
```

<210> SEQ ID NO 82
<211> LENGTH: 29
<212> TYPE: PRT
<213> ORGANISM: Artificial Sequence
<220> FEATURE:
<223> OTHER INFORMATION: Synthetic

<400> SEQUENCE: 82

```
Met Met Ile Arg Asp Asn Arg Leu Lys Thr Ser Leu Leu Arg Gly Leu
1               5                   10                  15

Thr Leu Thr Leu Leu Ser Leu Thr Leu Leu Ser Pro Ala
            20                  25
```

<210> SEQ ID NO 83
<211> LENGTH: 28
<212> TYPE: PRT
<213> ORGANISM: Artificial Sequence
<220> FEATURE:
<223> OTHER INFORMATION: Synthetic

<400> SEQUENCE: 83

```
Met Met Ile Arg Asp Asn Arg Leu Lys Thr Ser Leu Leu Arg Gly Leu
1               5                   10                  15

Thr Leu Thr Leu Leu Ser Leu Thr Leu Leu Ser Pro
```

-continued

<210> SEQ ID NO 84
<211> LENGTH: 27
<212> TYPE: PRT
<213> ORGANISM: Artificial Sequence
<220> FEATURE:
<223> OTHER INFORMATION: Synthetic

<400> SEQUENCE: 84

Met Met Ile Arg Asp Asn Arg Leu Lys Thr Ser Leu Leu Arg Gly Leu
1               5                   10                  15

Thr Leu Thr Leu Leu Ser Leu Thr Leu Leu Ser
            20                  25

<210> SEQ ID NO 85
<211> LENGTH: 26
<212> TYPE: PRT
<213> ORGANISM: Artificial Sequence
<220> FEATURE:
<223> OTHER INFORMATION: Synthetic

<400> SEQUENCE: 85

Met Met Ile Arg Asp Asn Arg Leu Lys Thr Ser Leu Leu Arg Gly Leu
1               5                   10                  15

Thr Leu Thr Leu Leu Ser Leu Thr Leu Leu
            20                  25

<210> SEQ ID NO 86
<211> LENGTH: 25
<212> TYPE: PRT
<213> ORGANISM: Artificial Sequence
<220> FEATURE:
<223> OTHER INFORMATION: Synthetic

<400> SEQUENCE: 86

Met Met Ile Arg Asp Asn Arg Leu Lys Thr Ser Leu Leu Arg Gly Leu
1               5                   10                  15

Thr Leu Thr Leu Leu Ser Leu Thr Leu
            20                  25

<210> SEQ ID NO 87
<211> LENGTH: 24
<212> TYPE: PRT
<213> ORGANISM: Artificial Sequence
<220> FEATURE:
<223> OTHER INFORMATION: Synthetic

<400> SEQUENCE: 87

Met Met Ile Arg Asp Asn Arg Leu Lys Thr Ser Leu Leu Arg Gly Leu
1               5                   10                  15

Thr Leu Thr Leu Leu Ser Leu Thr
            20

<210> SEQ ID NO 88
<211> LENGTH: 23
<212> TYPE: PRT
<213> ORGANISM: Artificial Sequence
<220> FEATURE:
<223> OTHER INFORMATION: Synthetic

<400> SEQUENCE: 88

Met Met Ile Arg Asp Asn Arg Leu Lys Thr Ser Leu Leu Arg Gly Leu
1               5                   10                  15

Thr Leu Thr Leu Leu Ser Leu

<210> SEQ ID NO 89
<211> LENGTH: 22
<212> TYPE: PRT
<213> ORGANISM: Artificial Sequence
<220> FEATURE:
<223> OTHER INFORMATION: Synthetic

<400> SEQUENCE: 89

Met Met Ile Arg Asp Asn Arg Leu Lys Thr Ser Leu Leu Arg Gly Leu
1               5                   10                  15

Thr Leu Thr Leu Leu Ser
            20

<210> SEQ ID NO 90
<211> LENGTH: 15
<212> TYPE: PRT
<213> ORGANISM: Artificial Sequence
<220> FEATURE:
<223> OTHER INFORMATION: Synthetic

<400> SEQUENCE: 90

Lys Arg Asn Leu Leu Val Met Gly Leu Ala Val Leu Leu Ser Ala
1               5                   10                  15

<210> SEQ ID NO 91
<211> LENGTH: 16
<212> TYPE: PRT
<213> ORGANISM: Artificial Sequence
<220> FEATURE:
<223> OTHER INFORMATION: Synthetic

<400> SEQUENCE: 91

Met Ile Lys Arg Asn Leu Leu Val Met Gly Leu Ala Val Leu Leu Ser
1               5                   10                  15

<210> SEQ ID NO 92
<211> LENGTH: 15
<212> TYPE: PRT
<213> ORGANISM: Artificial Sequence
<220> FEATURE:
<223> OTHER INFORMATION: Synthetic

<400> SEQUENCE: 92

Met Ile Lys Arg Asn Leu Leu Val Met Gly Leu Ala Val Leu Leu
1               5                   10                  15

<210> SEQ ID NO 93
<211> LENGTH: 14
<212> TYPE: PRT
<213> ORGANISM: Artificial Sequence
<220> FEATURE:
<223> OTHER INFORMATION: Synthetic

<400> SEQUENCE: 93

Met Ile Lys Arg Asn Leu Leu Val Met Gly Leu Ala Val Leu
1               5                   10

<210> SEQ ID NO 94
<211> LENGTH: 13
<212> TYPE: PRT
<213> ORGANISM: Artificial Sequence
<220> FEATURE:
<223> OTHER INFORMATION: Synthetic

<400> SEQUENCE: 94

```
Met Ile Lys Arg Asn Leu Leu Val Met Gly Leu Ala Val
1               5                   10
```

```
<210> SEQ ID NO 95
<211> LENGTH: 12
<212> TYPE: PRT
<213> ORGANISM: Artificial Sequence
<220> FEATURE:
<223> OTHER INFORMATION: Synthetic

<400> SEQUENCE: 95

Met Ile Lys Arg Asn Leu Leu Val Met Gly Leu Ala
1               5                   10
```

```
<210> SEQ ID NO 96
<211> LENGTH: 11
<212> TYPE: PRT
<213> ORGANISM: Artificial Sequence
<220> FEATURE:
<223> OTHER INFORMATION: Synthetic

<400> SEQUENCE: 96

Met Ile Lys Arg Asn Leu Leu Val Met Gly Leu
1               5                   10
```

```
<210> SEQ ID NO 97
<211> LENGTH: 10
<212> TYPE: PRT
<213> ORGANISM: Artificial Sequence
<220> FEATURE:
<223> OTHER INFORMATION: Synthetic

<400> SEQUENCE: 97

Met Ile Lys Arg Asn Leu Leu Val Met Gly
1               5                   10
```

```
<210> SEQ ID NO 98
<211> LENGTH: 9
<212> TYPE: PRT
<213> ORGANISM: Artificial Sequence
<220> FEATURE:
<223> OTHER INFORMATION: Synthetic

<400> SEQUENCE: 98

Met Ile Lys Arg Asn Leu Leu Val Met
1               5
```

```
<210> SEQ ID NO 99
<211> LENGTH: 8
<212> TYPE: PRT
<213> ORGANISM: Artificial Sequence
<220> FEATURE:
<223> OTHER INFORMATION: Synthetic

<400> SEQUENCE: 99

Met Ile Lys Arg Asn Leu Leu Val
1               5
```

```
<210> SEQ ID NO 100
<211> LENGTH: 7
<212> TYPE: PRT
<213> ORGANISM: Artificial Sequence
<220> FEATURE:
<223> OTHER INFORMATION: Synthetic

<400> SEQUENCE: 100

Met Ile Lys Arg Asn Leu Leu
1               5
```

<210> SEQ ID NO 101
<211> LENGTH: 834
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(834)

<400> SEQUENCE: 101

| | | | | | | | | | | | | | | | | |
|---|---|---|---|---|---|---|---|---|---|---|---|---|---|---|---|---|
| atg | aaa | ctg | aaa | cgt | ttg | atg | gcg | gca | atg | act | ttt | gtc | gct | gct | ggc | 48 |
| Met | Lys | Leu | Lys | Arg | Leu | Met | Ala | Ala | Met | Thr | Phe | Val | Ala | Ala | Gly | |
| 1 | | | | 5 | | | | | 10 | | | | | 15 | | |
| gtt | gcg | acc | gcc | aac | gcg | gtg | gcc | gcc | cag | gtg | cag | ctg | cag | gag | tcg | 96 |
| Val | Ala | Thr | Ala | Asn | Ala | Val | Ala | Ala | Gln | Val | Gln | Leu | Gln | Glu | Ser | |
| | | | 20 | | | | | 25 | | | | | 30 | | | |
| ggc | cca | gga | ctg | gtg | aag | cct | tcg | gag | acc | ctg | tcc | ctc | acc | tgc | act | 144 |
| Gly | Pro | Gly | Leu | Val | Lys | Pro | Ser | Glu | Thr | Leu | Ser | Leu | Thr | Cys | Thr | |
| | | 35 | | | | | 40 | | | | | 45 | | | | |
| gtc | tct | ggt | ggt | tcc | atc | agt | agt | tat | cac | tgg | agc | tgg | atc | cgg | cag | 192 |
| Val | Ser | Gly | Gly | Ser | Ile | Ser | Ser | Tyr | His | Trp | Ser | Trp | Ile | Arg | Gln | |
| 50 | | | | | 55 | | | | | 60 | | | | | | |
| ccc | cca | ggg | aag | gga | ctg | gag | tgg | att | ggg | tat | atc | tat | tac | agt | ggg | 240 |
| Pro | Pro | Gly | Lys | Gly | Leu | Glu | Trp | Ile | Gly | Tyr | Ile | Tyr | Tyr | Ser | Gly | |
| 65 | | | | | 70 | | | | | 75 | | | | | 80 | |
| agc | acc | aac | tac | aac | ccc | tcc | ctc | aag | aat | cga | gtc | acc | ata | tct | gta | 288 |
| Ser | Thr | Asn | Tyr | Asn | Pro | Ser | Leu | Lys | Asn | Arg | Val | Thr | Ile | Ser | Val | |
| | | | | 85 | | | | | 90 | | | | | 95 | | |
| gac | acg | tcc | aag | aac | cag | ttc | tcc | ctg | aac | ctg | agg | tct | gtg | acc | gct | 336 |
| Asp | Thr | Ser | Lys | Asn | Gln | Phe | Ser | Leu | Asn | Leu | Arg | Ser | Val | Thr | Ala | |
| | | | 100 | | | | | 105 | | | | | 110 | | | |
| gca | gac | acg | gcc | gtg | tat | tac | tgt | gcg | cga | gga | acg | tat | ggc | cca | gcc | 384 |
| Ala | Asp | Thr | Ala | Val | Tyr | Tyr | Cys | Ala | Arg | Gly | Thr | Tyr | Gly | Pro | Ala | |
| | | 115 | | | | | 120 | | | | | 125 | | | | |
| gga | gat | gct | ttt | gat | atc | tgg | ggg | caa | ggg | acc | acg | gtc | acc | gtc | tcg | 432 |
| Gly | Asp | Ala | Phe | Asp | Ile | Trp | Gly | Gln | Gly | Thr | Thr | Val | Thr | Val | Ser | |
| 130 | | | | | 135 | | | | | 140 | | | | | | |
| agt | ggt | gga | ggc | ggt | tca | ggc | gga | ggt | ggc | agc | ggc | ggt | ggc | gga | tcg | 480 |
| Ser | Gly | Gly | Gly | Gly | Ser | Gly | Gly | Gly | Gly | Ser | Gly | Gly | Gly | Gly | Ser | |
| 145 | | | | | 150 | | | | | 155 | | | | | 160 | |
| gac | atc | cag | atg | acc | cag | tct | cct | tcc | acc | ctg | tct | gca | tct | att | gga | 528 |
| Asp | Ile | Gln | Met | Thr | Gln | Ser | Pro | Ser | Thr | Leu | Ser | Ala | Ser | Ile | Gly | |
| | | | 165 | | | | | 170 | | | | | 175 | | | |
| gac | aga | gtc | acc | atc | acc | tgc | cgg | gcc | agt | gag | ggt | att | tat | cac | tgg | 576 |
| Asp | Arg | Val | Thr | Ile | Thr | Cys | Arg | Ala | Ser | Glu | Gly | Ile | Tyr | His | Trp | |
| | | 180 | | | | | 185 | | | | | 190 | | | | |
| ttg | gcc | tgg | tat | cag | cag | aag | cca | ggg | aaa | gcc | cct | aaa | ctc | ctg | atc | 624 |
| Leu | Ala | Trp | Tyr | Gln | Gln | Lys | Pro | Gly | Lys | Ala | Pro | Lys | Leu | Leu | Ile | |
| | | 195 | | | | | 200 | | | | | 205 | | | | |
| tat | aag | gcc | tct | agt | tta | gcc | agt | ggg | gcc | cca | tca | agg | ttc | agc | ggc | 672 |
| Tyr | Lys | Ala | Ser | Ser | Leu | Ala | Ser | Gly | Ala | Pro | Ser | Arg | Phe | Ser | Gly | |
| | 210 | | | | | 215 | | | | | 220 | | | | | |
| agt | gga | tct | ggg | aca | gat | ttc | act | ctc | acc | atc | agc | agc | ctg | cag | cct | 720 |
| Ser | Gly | Ser | Gly | Thr | Asp | Phe | Thr | Leu | Thr | Ile | Ser | Ser | Leu | Gln | Pro | |
| 225 | | | | | 230 | | | | | 235 | | | | | 240 | |
| gat | gat | ttt | gca | act | tat | tac | tgc | caa | caa | tat | agt | aat | tat | ccg | ctc | 768 |
| Asp | Asp | Phe | Ala | Thr | Tyr | Tyr | Cys | Gln | Gln | Tyr | Ser | Asn | Tyr | Pro | Leu | |
| | | | | 245 | | | | | 250 | | | | | 255 | | |
| act | ttc | ggc | gga | ggg | acc | aag | ctg | gag | atc | aaa | cgt | gcg | gcc | gca | cat | 816 |
| Thr | Phe | Gly | Gly | Gly | Thr | Lys | Leu | Glu | Ile | Lys | Arg | Ala | Ala | Ala | His | |

```
                            260                 265                 270
cac cat cat cac cat taa                                                              834
His His His His His
        275

<210> SEQ ID NO 102
<211> LENGTH: 277
<212> TYPE: PRT
<213> ORGANISM: Artificial Sequence
<220> FEATURE:
<223> OTHER INFORMATION: Synthetic Construct

<400> SEQUENCE: 102

Met Lys Leu Lys Arg Leu Met Ala Ala Met Thr Phe Val Ala Ala Gly
1               5                   10                  15

Val Ala Thr Ala Asn Ala Val Ala Gln Val Gln Leu Gln Glu Ser
            20                  25                  30

Gly Pro Gly Leu Val Lys Pro Ser Glu Thr Leu Ser Leu Thr Cys Thr
            35                  40                  45

Val Ser Gly Gly Ser Ile Ser Ser Tyr His Trp Ser Trp Ile Arg Gln
        50                  55                  60

Pro Pro Gly Lys Gly Leu Glu Trp Ile Gly Tyr Ile Tyr Tyr Ser Gly
65                  70                  75                  80

Ser Thr Asn Tyr Asn Pro Ser Leu Lys Asn Arg Val Thr Ile Ser Val
                85                  90                  95

Asp Thr Ser Lys Asn Gln Phe Ser Leu Asn Leu Arg Ser Val Thr Ala
            100                 105                 110

Ala Asp Thr Ala Val Tyr Tyr Cys Ala Arg Gly Thr Tyr Gly Pro Ala
        115                 120                 125

Gly Asp Ala Phe Asp Ile Trp Gly Gln Gly Thr Thr Val Thr Val Ser
    130                 135                 140

Ser Gly Gly Gly Gly Ser Gly Gly Gly Gly Ser Gly Gly Gly Gly Ser
145                 150                 155                 160

Asp Ile Gln Met Thr Gln Ser Pro Ser Thr Leu Ser Ala Ser Ile Gly
                165                 170                 175

Asp Arg Val Thr Ile Thr Cys Arg Ala Ser Glu Gly Ile Tyr His Trp
            180                 185                 190

Leu Ala Trp Tyr Gln Gln Lys Pro Gly Lys Ala Pro Lys Leu Leu Ile
        195                 200                 205

Tyr Lys Ala Ser Ser Leu Ala Ser Gly Ala Pro Ser Arg Phe Ser Gly
    210                 215                 220

Ser Gly Ser Gly Thr Asp Phe Thr Leu Thr Ile Ser Ser Leu Gln Pro
225                 230                 235                 240

Asp Asp Phe Ala Thr Tyr Tyr Cys Gln Gln Tyr Ser Asn Tyr Pro Leu
                245                 250                 255

Thr Phe Gly Gly Gly Thr Lys Leu Glu Ile Lys Arg Ala Ala Ala His
            260                 265                 270

His His His His His
        275

<210> SEQ ID NO 103
<211> LENGTH: 33
<212> TYPE: DNA
<213> ORGANISM: Artificial Sequence
<220> FEATURE:
<223> OTHER INFORMATION: Synthetic

<400> SEQUENCE: 103
```

```
gctctagagg aggtaactta tgaaactgaa acg                                    33
```

<210> SEQ ID NO 104
<211> LENGTH: 24
<212> TYPE: DNA
<213> ORGANISM: Artificial Sequence
<220> FEATURE:
<223> OTHER INFORMATION: Synthetic

<400> SEQUENCE: 104

```
ctgcacctgg gcggccaccg cgtt                                             24
```

<210> SEQ ID NO 105
<211> LENGTH: 24
<212> TYPE: DNA
<213> ORGANISM: Artificial Sequence
<220> FEATURE:
<223> OTHER INFORMATION: Synthetic

<400> SEQUENCE: 105

```
aacgcggtgg ccgcccaggt gcag                                             24
```

<210> SEQ ID NO 106
<211> LENGTH: 52
<212> TYPE: DNA
<213> ORGANISM: Artificial Sequence
<220> FEATURE:
<223> OTHER INFORMATION: Synthetic

<400> SEQUENCE: 106

```
acgcgtcgac ttattaatgg tgatgatggt gatgtgcggc cgcacgttga tc              52
```

<210> SEQ ID NO 107
<211> LENGTH: 30
<212> TYPE: DNA
<213> ORGANISM: Artificial Sequence
<220> FEATURE:
<223> OTHER INFORMATION: Synthetic

<400> SEQUENCE: 107

```
gggaatggtt gggaaggcca ccgcgttggc                                       30
```

<210> SEQ ID NO 108
<211> LENGTH: 50
<212> TYPE: DNA
<213> ORGANISM: Artificial Sequence
<220> FEATURE:
<223> OTHER INFORMATION: Synthetic

<400> SEQUENCE: 108

```
agagaactag taaaaaggag aaatccatgg ctacaggctc ccggacgtcc                 50
```

<210> SEQ ID NO 109
<211> LENGTH: 38
<212> TYPE: DNA
<213> ORGANISM: Artificial Sequence
<220> FEATURE:
<223> OTHER INFORMATION: Synthetic

<400> SEQUENCE: 109

```
agagactcga gtcattagaa gccacagctg ccctccac                              38
```

<210> SEQ ID NO 110
<211> LENGTH: 30
<212> TYPE: DNA
<213> ORGANISM: Artificial Sequence
<220> FEATURE:

<223> OTHER INFORMATION: Synthetic

<400> SEQUENCE: 110
gccaacgcgg tggccttccc aaccattccc                                    30

<210> SEQ ID NO 111
<211> LENGTH: 48
<212> TYPE: DNA
<213> ORGANISM: Artificial Sequence
<220> FEATURE:
<223> OTHER INFORMATION: Synthetic

<400> SEQUENCE: 111
agagactcga gtcattagaa gccacagctg ccctccacag agcggcac               48

<210> SEQ ID NO 112
<211> LENGTH: 645
<212> TYPE: DNA
<213> ORGANISM: Artificial Sequence
<220> FEATURE:
<223> OTHER INFORMATION: Synthetic
<220> FEATURE:
<221> NAME/KEY: CDS
<222> LOCATION: (1)..(645)

<400> SEQUENCE: 112

| atg | aaa | ctg | aaa | cgt | ttg | atg | gcg | gca | atg | act | ttt | gtc | gct | gct | ggc | 48 |
|-----|-----|-----|-----|-----|-----|-----|-----|-----|-----|-----|-----|-----|-----|-----|-----|----|
| Met | Lys | Leu | Lys | Arg | Leu | Met | Ala | Ala | Met | Thr | Phe | Val | Ala | Ala | Gly | |
| 1   |     |     |     | 5   |     |     |     |     | 10  |     |     |     |     | 15  |     | |

| gtt | gcg | acc | gcc | aac | gcg | gtg | gcc | ttc | cca | acc | att | ccc | tta | tcc | agg | 96 |
|-----|-----|-----|-----|-----|-----|-----|-----|-----|-----|-----|-----|-----|-----|-----|-----|----|
| Val | Ala | Thr | Ala | Asn | Ala | Val | Ala | Phe | Pro | Thr | Ile | Pro | Leu | Ser | Arg | |
|     |     |     | 20  |     |     |     |     | 25  |     |     |     |     | 30  |     |     | |

| cct | ttt | gac | aac | gct | atg | ctc | cgc | gcc | cat | cgt | ctg | cac | cag | ctg | gcc | 144 |
|-----|-----|-----|-----|-----|-----|-----|-----|-----|-----|-----|-----|-----|-----|-----|-----|-----|
| Pro | Phe | Asp | Asn | Ala | Met | Leu | Arg | Ala | His | Arg | Leu | His | Gln | Leu | Ala | |
|     |     |     | 35  |     |     |     |     | 40  |     |     |     |     | 45  |     |     | |

| ttt | gac | acc | tac | cag | gag | ttt | gaa | gaa | gcc | tat | atc | cca | aag | gaa | cag | 192 |
|-----|-----|-----|-----|-----|-----|-----|-----|-----|-----|-----|-----|-----|-----|-----|-----|-----|
| Phe | Asp | Thr | Tyr | Gln | Glu | Phe | Glu | Glu | Ala | Tyr | Ile | Pro | Lys | Glu | Gln | |
|     | 50  |     |     |     |     | 55  |     |     |     |     | 60  |     |     |     |     | |

| aag | tat | tca | ttc | ctg | cag | aac | ccc | cag | acc | tcc | ctc | tgt | ttc | tca | gag | 240 |
|-----|-----|-----|-----|-----|-----|-----|-----|-----|-----|-----|-----|-----|-----|-----|-----|-----|
| Lys | Tyr | Ser | Phe | Leu | Gln | Asn | Pro | Gln | Thr | Ser | Leu | Cys | Phe | Ser | Glu | |
| 65  |     |     |     |     | 70  |     |     |     |     | 75  |     |     |     |     | 80  | |

| tct | att | ccg | aca | ccc | tcc | aac | agg | gag | gaa | aca | caa | cag | aaa | tcc | aac | 288 |
|-----|-----|-----|-----|-----|-----|-----|-----|-----|-----|-----|-----|-----|-----|-----|-----|-----|
| Ser | Ile | Pro | Thr | Pro | Ser | Asn | Arg | Glu | Glu | Thr | Gln | Gln | Lys | Ser | Asn | |
|     |     |     |     | 85  |     |     |     |     | 90  |     |     |     |     | 95  |     | |

| cta | gag | ctg | ctc | cgc | atc | tcc | ctg | ctg | ctc | atc | cag | tcg | tgg | ctg | gag | 336 |
|-----|-----|-----|-----|-----|-----|-----|-----|-----|-----|-----|-----|-----|-----|-----|-----|-----|
| Leu | Glu | Leu | Leu | Arg | Ile | Ser | Leu | Leu | Leu | Ile | Gln | Ser | Trp | Leu | Glu | |
|     |     |     | 100 |     |     |     |     | 105 |     |     |     |     | 110 |     |     | |

| ccc | gtg | cag | ttc | ctc | agg | agt | gtc | ttc | gcc | aac | agc | ctg | gtg | tac | ggc | 384 |
|-----|-----|-----|-----|-----|-----|-----|-----|-----|-----|-----|-----|-----|-----|-----|-----|-----|
| Pro | Val | Gln | Phe | Leu | Arg | Ser | Val | Phe | Ala | Asn | Ser | Leu | Val | Tyr | Gly | |
|     |     | 115 |     |     |     |     | 120 |     |     |     |     | 125 |     |     |     | |

| gcc | tct | gac | agc | aac | gtc | tat | gac | ctc | cta | aag | gac | cta | gag | gaa | ggc | 432 |
|-----|-----|-----|-----|-----|-----|-----|-----|-----|-----|-----|-----|-----|-----|-----|-----|-----|
| Ala | Ser | Asp | Ser | Asn | Val | Tyr | Asp | Leu | Leu | Lys | Asp | Leu | Glu | Glu | Gly | |
|     |     | 130 |     |     |     |     | 135 |     |     |     |     | 140 |     |     |     | |

| atc | caa | acg | ctg | atg | ggg | agg | ctg | gaa | gat | ggc | agc | ccc | cgg | act | ggg | 480 |
|-----|-----|-----|-----|-----|-----|-----|-----|-----|-----|-----|-----|-----|-----|-----|-----|-----|
| Ile | Gln | Thr | Leu | Met | Gly | Arg | Leu | Glu | Asp | Gly | Ser | Pro | Arg | Thr | Gly | |
| 145 |     |     |     |     | 150 |     |     |     |     | 155 |     |     |     |     | 160 | |

| cag | atc | ttc | aag | cag | acc | tac | agc | aag | ttc | gac | aca | aac | tca | cac | aac | 528 |
|-----|-----|-----|-----|-----|-----|-----|-----|-----|-----|-----|-----|-----|-----|-----|-----|-----|
| Gln | Ile | Phe | Lys | Gln | Thr | Tyr | Ser | Lys | Phe | Asp | Thr | Asn | Ser | His | Asn | |
|     |     |     | 165 |     |     |     |     | 170 |     |     |     |     | 175 |     |     | |

| gat | gac | cta | ctc | aag | aac | tac | ggg | ctg | ctc | tac | tgc | ttc | agg | aag | gac | 576 |
|-----|-----|-----|-----|-----|-----|-----|-----|-----|-----|-----|-----|-----|-----|-----|-----|-----|
| Asp | Asp | Leu | Leu | Lys | Asn | Tyr | Gly | Leu | Leu | Tyr | Cys | Phe | Arg | Lys | Asp | |
|     |     |     | 180 |     |     |     |     | 185 |     |     |     |     | 190 |     |     | |

| atg | gac | aag | gtc | gag | aca | ttc | ctg | cgc | atc | gtg | cag | tgc | cgc | tct | gtg | 624 |

```
Met Asp Lys Val Glu Thr Phe Leu Arg Ile Val Gln Cys Arg Ser Val
        195                 200                 205 gag ggc agc tgt ggc ttc taa                                              645
Glu Gly Ser Cys Gly Phe
    210
```

<210> SEQ ID NO 113
<211> LENGTH: 214
<212> TYPE: PRT
<213> ORGANISM: Artificial Sequence
<220> FEATURE:
<223> OTHER INFORMATION: Synthetic Construct

<400> SEQUENCE: 113

```
Met Lys Leu Lys Arg Leu Met Ala Ala Met Thr Phe Val Ala Ala Gly
1               5                   10                  15

Val Ala Thr Ala Asn Ala Val Ala Phe Pro Thr Ile Pro Leu Ser Arg
            20                  25                  30

Pro Phe Asp Asn Ala Met Leu Arg Ala His Arg Leu His Gln Leu Ala
        35                  40                  45

Phe Asp Thr Tyr Gln Glu Phe Glu Ala Tyr Ile Pro Lys Glu Gln
    50                  55                  60

Lys Tyr Ser Phe Leu Gln Asn Pro Gln Thr Ser Leu Cys Phe Ser Glu
65                  70                  75                  80

Ser Ile Pro Thr Pro Ser Asn Arg Glu Glu Thr Gln Gln Lys Ser Asn
                85                  90                  95

Leu Glu Leu Leu Arg Ile Ser Leu Leu Ile Gln Ser Trp Leu Glu
            100                 105                 110

Pro Val Gln Phe Leu Arg Ser Val Phe Ala Asn Ser Leu Val Tyr Gly
        115                 120                 125

Ala Ser Asp Ser Asn Val Tyr Asp Leu Leu Lys Asp Leu Glu Glu Gly
    130                 135                 140

Ile Gln Thr Leu Met Gly Arg Leu Glu Asp Gly Ser Pro Arg Thr Gly
145                 150                 155                 160

Gln Ile Phe Lys Gln Thr Tyr Ser Lys Phe Asp Thr Asn Ser His Asn
                165                 170                 175

Asp Asp Leu Leu Lys Asn Tyr Gly Leu Leu Tyr Cys Phe Arg Lys Asp
            180                 185                 190

Met Asp Lys Val Glu Thr Phe Leu Arg Ile Val Gln Cys Arg Ser Val
        195                 200                 205

Glu Gly Ser Cys Gly Phe
    210
```

<210> SEQ ID NO 114
<211> LENGTH: 13
<212> TYPE: PRT
<213> ORGANISM: Artificial Sequence
<220> FEATURE:
<223> OTHER INFORMATION: Synthetic

<400> SEQUENCE: 114

```
Ala Asp Lys Ile Ala Ile Val Asn Met Gly Ser Leu Phe
1               5                   10
```

<210> SEQ ID NO 115
<211> LENGTH: 17
<212> TYPE: PRT
<213> ORGANISM: Artificial Sequence
<220> FEATURE:
<223> OTHER INFORMATION: Synthetic

```
<400> SEQUENCE: 115

Gln Gln Val Ala Gln Lys Thr Gly Val Ser Asn Thr Leu Glu Asn Glu
1               5                   10                  15

Phe

<210> SEQ ID NO 116
<211> LENGTH: 10
<212> TYPE: PRT
<213> ORGANISM: Artificial Sequence
<220> FEATURE:
<223> OTHER INFORMATION: Synthetic

<400> SEQUENCE: 116

Phe Pro Thr Ile Pro Leu Ser Arg Pro Phe
1               5                   10

<210> SEQ ID NO 117
<211> LENGTH: 277
<212> TYPE: PRT
<213> ORGANISM: Artificial Sequence
<220> FEATURE:
<223> OTHER INFORMATION: Synthetic

<400> SEQUENCE: 117

Met Lys Leu Lys Asn Thr Leu Gly Leu Ala Ile Gly Ser Leu Ile Ala
1               5                   10                  15

Ala Thr Ser Phe Gly Val Leu Ala Ala Gln Val Gln Leu Gln Glu Ser
                20                  25                  30

Gly Pro Gly Leu Val Lys Pro Ser Glu Thr Leu Ser Leu Thr Cys Thr
            35                  40                  45

Val Ser Gly Gly Ser Ile Ser Ser Tyr His Trp Ser Trp Ile Arg Gln
        50                  55                  60

Pro Pro Gly Lys Gly Leu Glu Trp Ile Gly Tyr Ile Tyr Tyr Ser Gly
65                  70                  75                  80

Ser Thr Asn Tyr Asn Pro Ser Leu Lys Asn Arg Val Thr Ile Ser Val
                85                  90                  95

Asp Thr Ser Lys Asn Gln Phe Ser Leu Asn Leu Arg Ser Val Thr Ala
            100                 105                 110

Ala Asp Thr Ala Val Tyr Tyr Cys Ala Arg Gly Thr Tyr Gly Pro Ala
        115                 120                 125

Gly Asp Ala Phe Asp Ile Trp Gly Gln Gly Thr Thr Val Thr Val Ser
    130                 135                 140

Ser Gly Gly Gly Gly Ser Gly Gly Gly Gly Ser Gly Gly Gly Gly Ser
145                 150                 155                 160

Asp Ile Gln Met Thr Gln Ser Pro Ser Thr Leu Ser Ala Ser Ile Gly
                165                 170                 175

Asp Arg Val Thr Ile Thr Cys Arg Ala Ser Glu Gly Ile Tyr His Trp
            180                 185                 190

Leu Ala Trp Tyr Gln Gln Lys Pro Gly Lys Ala Pro Lys Leu Leu Ile
        195                 200                 205

Tyr Lys Ala Ser Ser Leu Ala Ser Gly Ala Pro Ser Arg Phe Ser Gly
    210                 215                 220

Ser Gly Ser Gly Thr Asp Phe Thr Leu Thr Ile Ser Ser Leu Gln Pro
225                 230                 235                 240

Asp Asp Phe Ala Thr Tyr Tyr Cys Gln Gln Tyr Ser Asn Tyr Pro Leu
                245                 250                 255

Thr Phe Gly Gly Gly Thr Lys Leu Glu Ile Lys Arg Ala Ala Ala His
            260                 265                 270
```

His His His His His
        275

<210> SEQ ID NO 118
<211> LENGTH: 277
<212> TYPE: PRT
<213> ORGANISM: Artificial Sequence
<220> FEATURE:
<223> OTHER INFORMATION: Synthetic

<400> SEQUENCE: 118

Met Lys Leu Lys Arg Leu Met Ala Ala Met Thr Phe Val Ala Ala Gly
1               5                   10                  15

Val Ala Thr Ala Asn Ala Val Ala Ala Gln Val Gln Leu Gln Glu Ser
            20                  25                  30

Gly Pro Gly Leu Val Lys Pro Ser Glu Thr Leu Ser Leu Thr Cys Thr
        35                  40                  45

Val Ser Gly Gly Ser Ile Ser Ser Tyr His Trp Ser Trp Ile Arg Gln
    50                  55                  60

Pro Pro Gly Lys Gly Leu Glu Trp Ile Gly Tyr Ile Tyr Tyr Ser Gly
65                  70                  75                  80

Ser Thr Asn Tyr Asn Pro Ser Leu Lys Asn Arg Val Thr Ile Ser Val
                85                  90                  95

Asp Thr Ser Lys Asn Gln Phe Ser Leu Asn Leu Arg Ser Val Thr Ala
            100                 105                 110

Ala Asp Thr Ala Val Tyr Tyr Cys Ala Arg Gly Thr Tyr Gly Pro Ala
        115                 120                 125

Gly Asp Ala Phe Asp Ile Trp Gly Gln Gly Thr Thr Val Thr Val Ser
    130                 135                 140

Ser Gly Gly Gly Gly Ser Gly Gly Gly Ser Gly Gly Gly Gly Ser
145                 150                 155                 160

Asp Ile Gln Met Thr Gln Ser Pro Ser Thr Leu Ser Ala Ser Ile Gly
                165                 170                 175

Asp Arg Val Thr Ile Thr Cys Arg Ala Ser Glu Gly Ile Tyr His Trp
            180                 185                 190

Leu Ala Trp Tyr Gln Gln Lys Pro Gly Lys Ala Pro Lys Leu Leu Ile
        195                 200                 205

Tyr Lys Ala Ser Ser Leu Ala Ser Gly Ala Pro Ser Arg Phe Ser Gly
    210                 215                 220

Ser Gly Ser Gly Thr Asp Phe Thr Leu Thr Ile Ser Ser Leu Gln Pro
225                 230                 235                 240

Asp Asp Phe Ala Thr Tyr Tyr Cys Gln Gln Tyr Ser Asn Tyr Pro Leu
                245                 250                 255

Thr Phe Gly Gly Gly Thr Lys Leu Glu Ile Lys Arg Ala Ala Ala His
            260                 265                 270

His His His His His
        275

<210> SEQ ID NO 119
<211> LENGTH: 161
<212> TYPE: PRT
<213> ORGANISM: Artificial Sequence
<220> FEATURE:
<223> OTHER INFORMATION: Synthetic

<400> SEQUENCE: 119

Met Lys Lys Trp Leu Leu Ala Ala Gly Leu Gly Leu Ala Leu Ala Thr
1               5                   10                  15

```
Ser Ala Gln Ala Ala Asp Lys Ile Ala Ile Val Asn Met Gly Ser Leu
         20                  25                  30

Phe Gln Gln Val Ala Gln Lys Thr Gly Val Ser Asn Thr Leu Glu Asn
         35                  40                  45

Glu Phe Lys Gly Arg Ala Ser Glu Leu Gln Arg Met Glu Thr Asp Leu
 50                  55                  60

Gln Ala Lys Met Lys Lys Leu Gln Ser Met Lys Ala Gly Ser Asp Arg
 65                  70                  75                  80

Thr Lys Leu Glu Lys Asp Val Met Ala Gln Arg Gln Thr Phe Ala Gln
             85                  90                  95

Lys Ala Gln Ala Phe Glu Gln Asp Arg Ala Arg Arg Ser Asn Glu Glu
             100                 105                 110

Arg Gly Lys Leu Val Thr Arg Ile Gln Thr Ala Val Lys Ser Val Ala
             115                 120                 125

Asn Ser Gln Asp Ile Asp Leu Val Val Asp Ala Asn Ala Val Ala Tyr
 130                 135                 140

Asn Ser Ser Asp Val Lys Asp Ile Thr Ala Asp Val Leu Lys Gln Val
 145                 150                 155                 160

Lys

<210> SEQ ID NO 120
<211> LENGTH: 140
<212> TYPE: PRT
<213> ORGANISM: Artificial Sequence
<220> FEATURE:
<223> OTHER INFORMATION: Synthetic

<400> SEQUENCE: 120

Ala Asp Lys Ile Ala Ile Val Asn Met Gly Ser Leu Phe Gln Gln Val
 1               5                   10                  15

Ala Gln Lys Thr Gly Val Ser Asn Thr Leu Glu Asn Glu Phe Lys Gly
             20                  25                  30

Arg Ala Ser Glu Leu Gln Arg Met Glu Thr Asp Leu Gln Ala Lys Met
             35                  40                  45

Lys Lys Leu Gln Ser Met Lys Ala Gly Ser Asp Arg Thr Lys Leu Glu
 50                  55                  60

Lys Asp Val Met Ala Gln Arg Gln Thr Phe Ala Gln Lys Ala Gln Ala
 65                  70                  75                  80

Phe Glu Gln Asp Arg Ala Arg Arg Ser Asn Glu Glu Arg Gly Lys Leu
             85                  90                  95

Val Thr Arg Ile Gln Thr Ala Val Lys Ser Val Ala Asn Ser Ala Asp
             100                 105                 110

Ile Asp Leu Val Val Asp Ala Asn Ala Val Ala Tyr Asn Ser Ser Asp
             115                 120                 125

Val Lys Asp Ile Thr Ala Asp Val Leu Lys Gln Val
             130                 135                 140
```